(12) United States Patent
Bryan et al.

(10) Patent No.: US 8,278,415 B2
(45) Date of Patent: *Oct. 2, 2012

(54) DIMERIC HIGH AFFINITY EGFR CONSTRUCTS AND USES THEREOF

(75) Inventors: Wang Bryan, Wyomissing, PA (US); Frank Shi, Downingtown, PA (US); Juliane Mills, Wallingford, PA (US)

(73) Assignee: Centocor, Inc., Malvern, PA (US)

( * ) Notice: Subject to any disclaimer, the term of this patent is extended or adjusted under 35 U.S.C. 154(b) by 368 days.

This patent is subject to a terminal disclaimer.

(21) Appl. No.: 12/514,631

(22) PCT Filed: Dec. 20, 2007

(86) PCT No.: PCT/US2007/088376
§ 371 (c)(1), (2), (4) Date: Nov. 17, 2009

(87) PCT Pub. No.: WO2008/079976
PCT Pub. Date: Jul. 3, 2008

(65) Prior Publication Data
US 2010/0098681 A1   Apr. 22, 2010

Related U.S. Application Data

(60) Provisional application No. 60/876,421, filed on Dec. 21, 2006.

(51) Int. Cl.
C07K 14/00 (2006.01)

(52) U.S. Cl. .................................................. 530/350

(58) Field of Classification Search .................. None
See application file for complete search history.

(56) References Cited

U.S. PATENT DOCUMENTS

| | | | |
|---|---|---|---|
| 5,013,556 A | 5/1991 | Woodle et al. | |
| 5,316,771 A | 5/1994 | Barenholz et al. | |
| 5,395,619 A | 3/1995 | Zalipsky et al. | |
| 5,631,018 A | 5/1997 | Zalipsky et al. | |
| 5,945,122 A | 8/1999 | Abra et al. | |
| 6,056,973 A | 5/2000 | Allen et al. | |
| 6,235,883 B1 | 5/2001 | Jakobovits et al. | |
| 6,946,543 B2 | 9/2005 | Ward et al. | |
| 7,449,559 B2 * | 11/2008 | Ward et al. | 530/402 |

FOREIGN PATENT DOCUMENTS

| | | |
|---|---|---|
| WO | WO 96/040120 A1 | 12/1996 |
| WO | WO 2004/002417 A2 | 1/2004 |
| WO | WO 2004/002424 A2 | 1/2004 |
| WO | WO 2005/032460 A2 | 4/2005 |
| WO | WO 2005/081687 A2 | 9/2005 |

OTHER PUBLICATIONS

Traxler, Expert Opin Ther Targets 7: 215-34, 2003.
Ullrich, A and Schelssinger, J. Cell 61: 203-212, 1990.
Burgess, et al., Mol Cell 12:541-552, 2003.
Dawson et al., Mol Cell Biol. 25:7734-7742, 2005.
Elleman et al., Biochemistry 40: 8930-8939, 2001.
Choowongkomon, K et al. J. Biol. Chem., 280(25): 24043-24052, 2005.
Zhou et al., Biochemistry, 32: 8193-8198, 1993.
Mattoon et al., PNAS, vol. 101, No. 4: 923-928, 2004.
Li et al., Cancer Cell, vol. 7:301-311, 2005.
Johns et al., Journal of Biological Chemistry, vol. 279, No. 29: 30375-30384, 2004.
Clayton et al., Journal of Biological Chemistry, vol. 280, No. 34: 30392-30399, 2005.
Ferguson et al., Molecular Cell, vol. 11: 507-517, 2003.
Ogiso et al., Call, vol. 110: 775-787, 2002.
EGF Receptor Inhibition: Attacks on Multiple Fronts, Cancer Cell, vol. 7: 287-288, 2005.

* cited by examiner

*Primary Examiner* — Hong Sang
(74) *Attorney, Agent, or Firm* — Kenneth J. Dow

(57) ABSTRACT

Polypeptides comprising EGFR extracellular domains I-III capable of forming dimeric EGF-binding proteins are provided. The dimeric construct of the invention is useful in applications where high affinity EGF binding is desired and can be used to select agents capable of binding to native EGFR in the presence of EGF.

2 Claims, 17 Drawing Sheets

FIG. 2
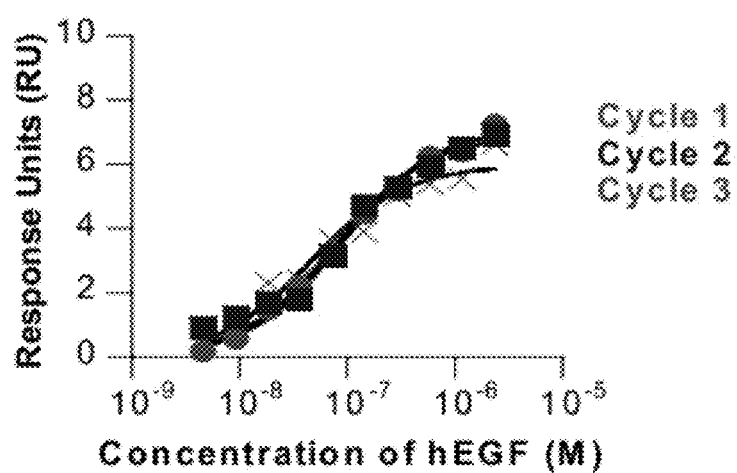
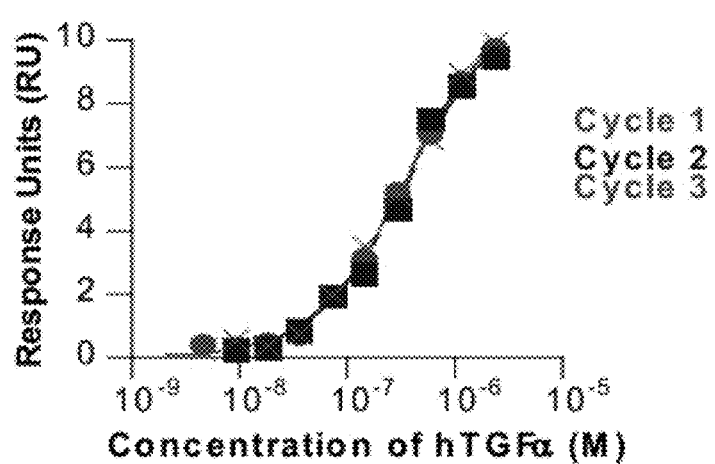

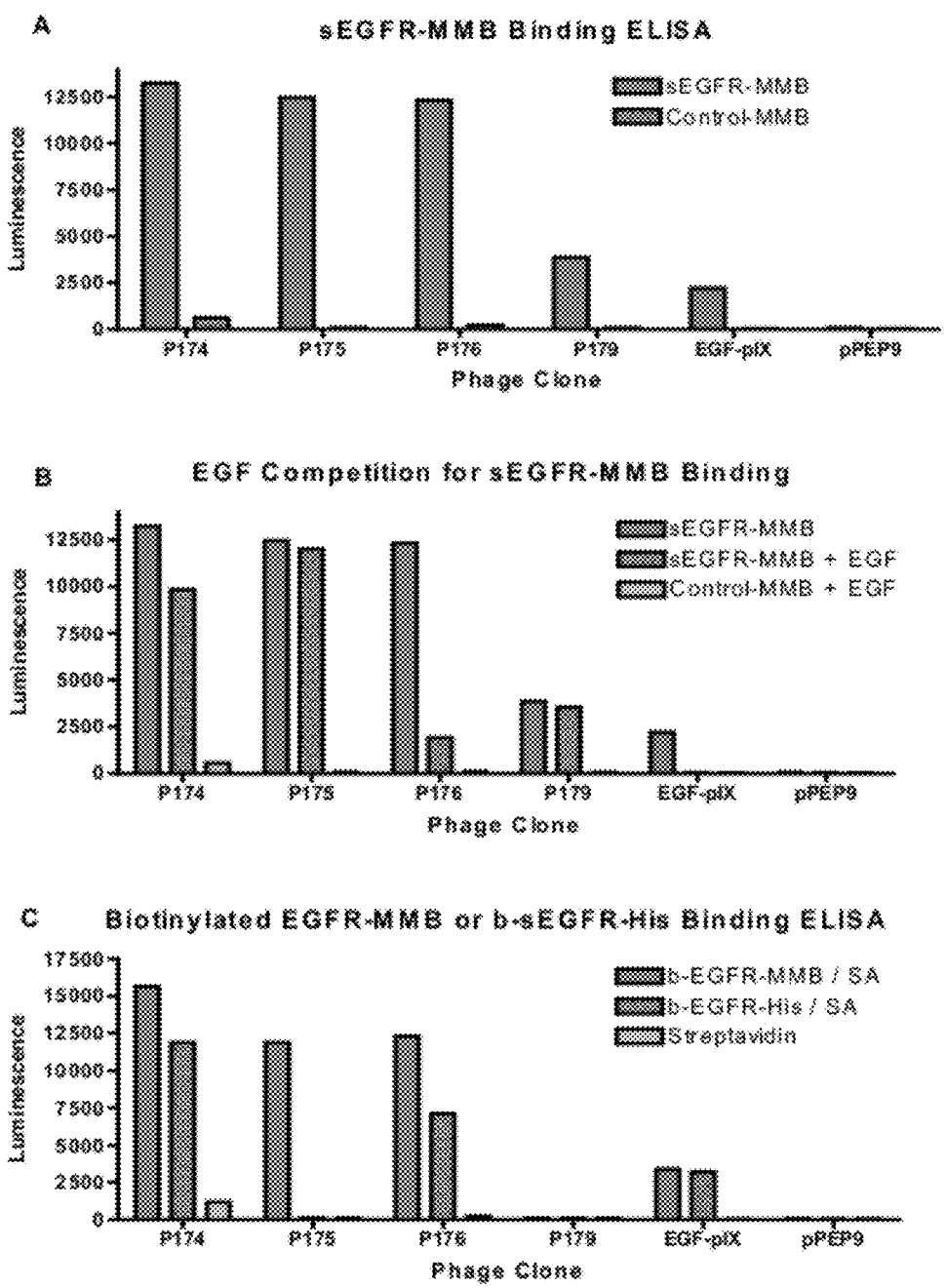

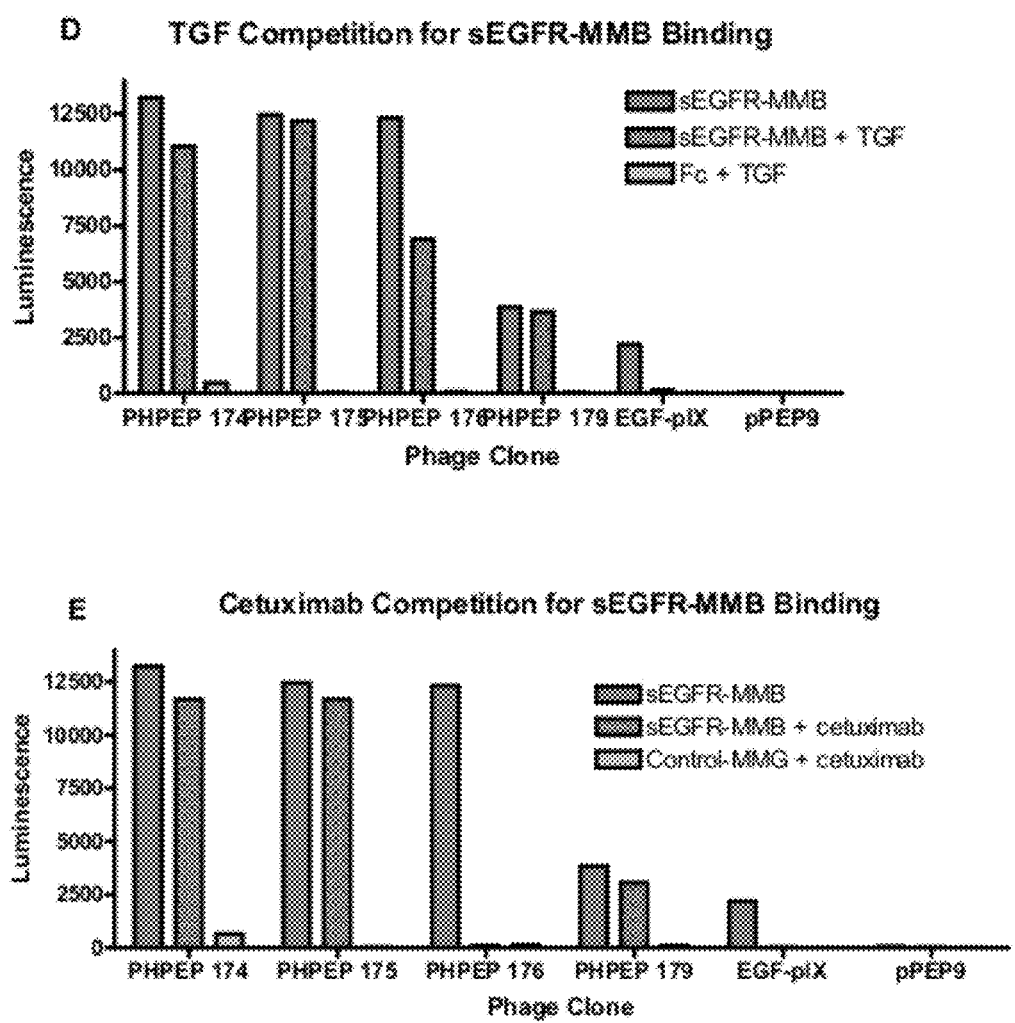
Fig. 7D-E

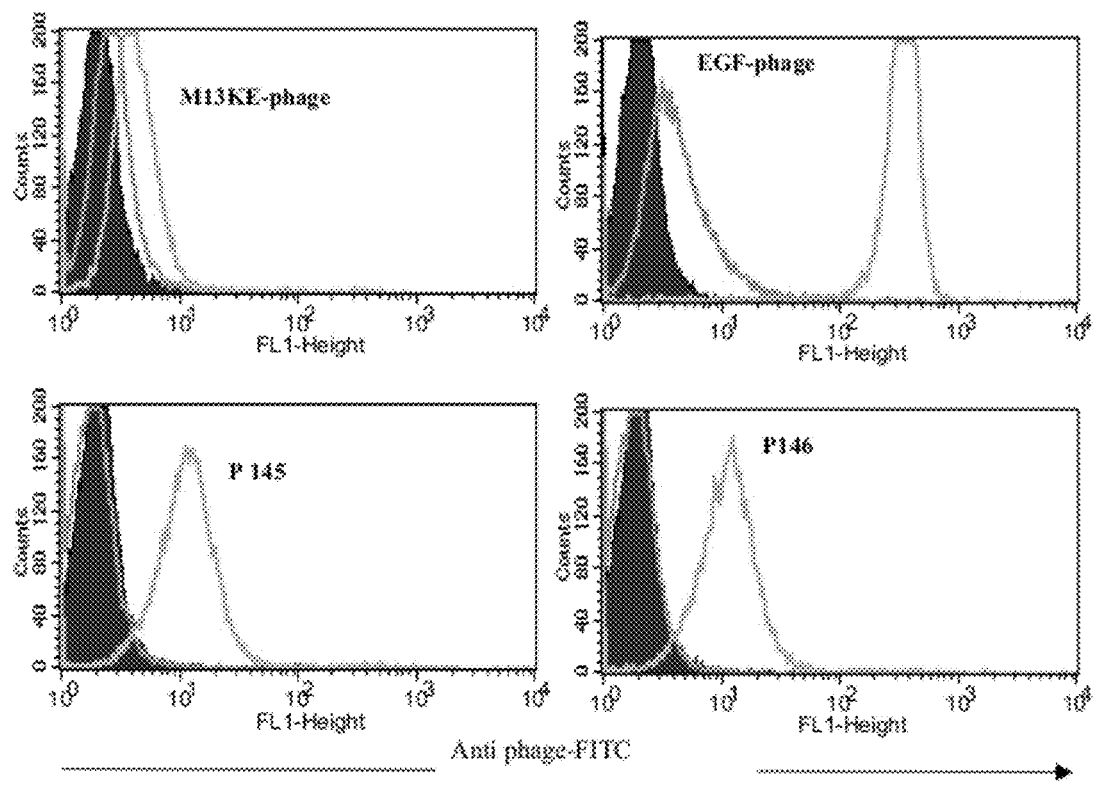

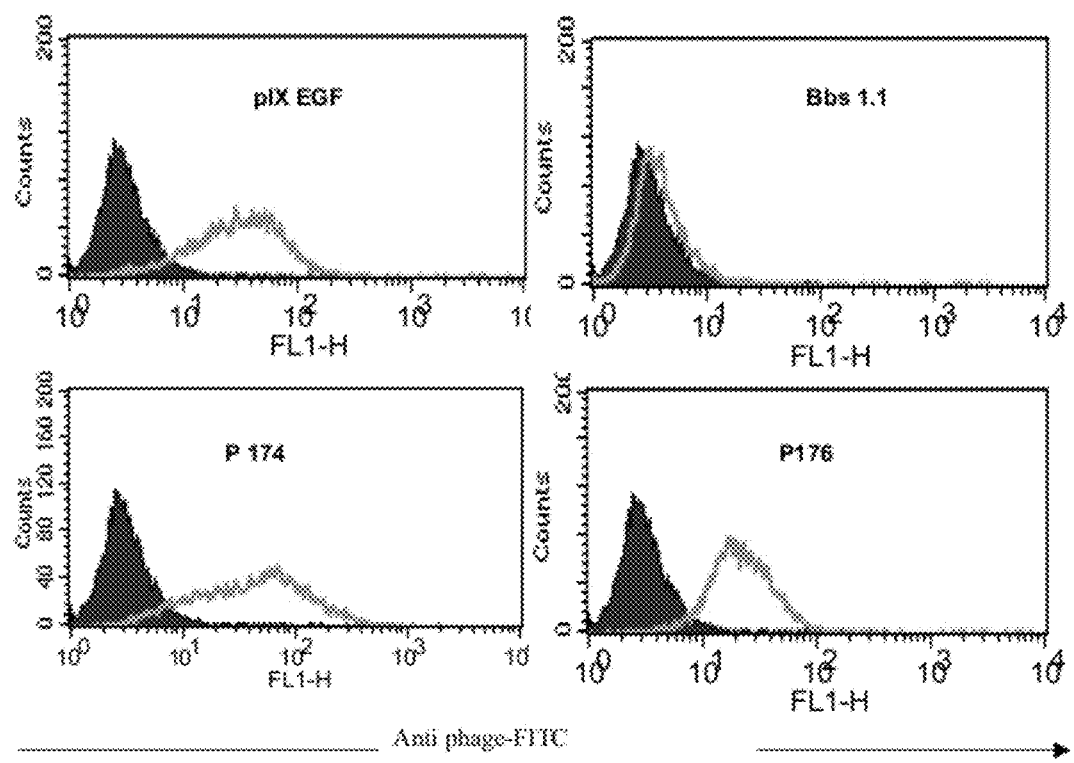

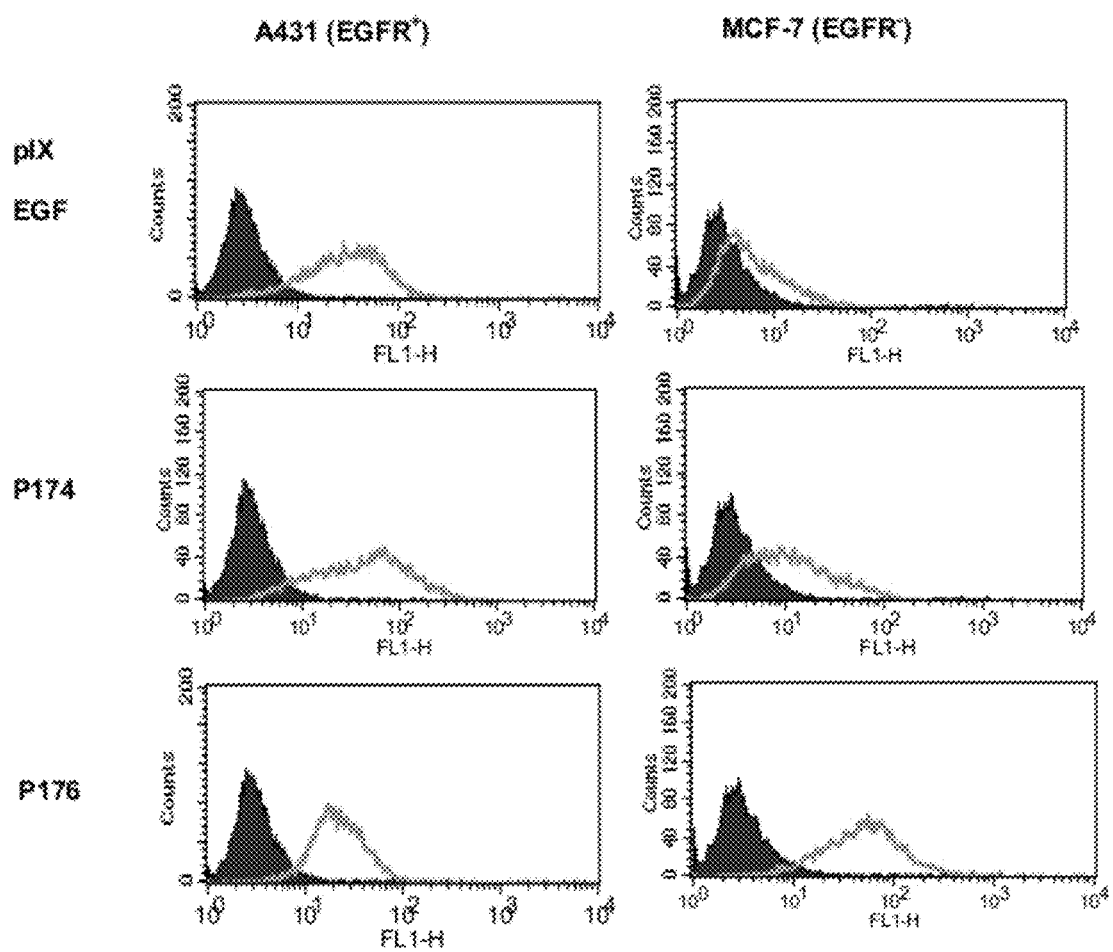

FIG. 10
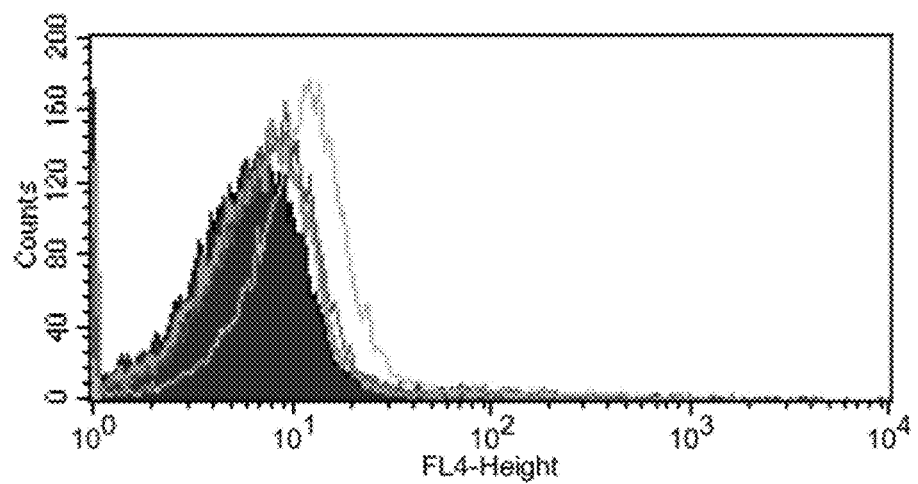
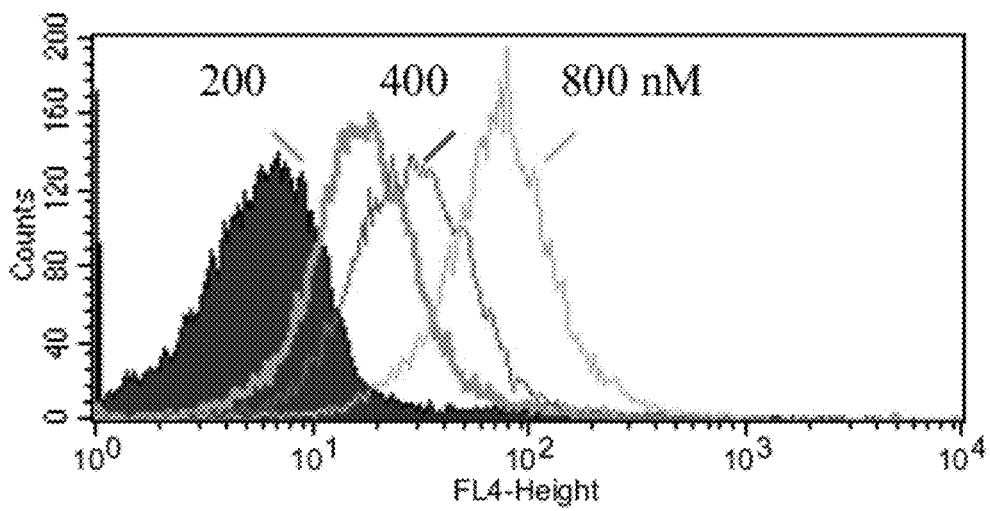

DIMERIC HIGH AFFINITY EGFR CONSTRUCTS AND USES THEREOF

CROSS-REFERENCE TO RELATED APPLICATIONS

This application claims the benefit of International Application Number PCT/US2007/088376, filed 20 Dec. 2007, which claims the benefit of U.S. Provisional Application No. 60/876,421, filed 21 Dec. 2006. The entire contents of each of the aforesaid applications are incorporated herein by reference in their entirety.

BACKGROUND OF THE INVENTION

1. Field of the Invention

The invention relates to compositions which are EGFR targeting peptides and methods of treating, preventing or managing hyperproliferative cell disease associated with cells expressing EGFR, by administering a delivery vehicle composition comprising an EGFR targeting peptide and a bioactive agent.

2. Background

Epidermal growth factor receptor (EGFR) is a cell surface glycoprotein that is a member of the ErbB family of receptors (reviewed in Yarden Sliwkowski, Nat Rev Mol Cell Biol 2: 127-37, 2001). Activation of EGFR leads to signal transduction cascades that promote cell proliferation and cell growth. Activation is initiated by ligands including epidermal growth factor (EGF) and transforming growth factor-α (TGF-α) binding to the extracellular domain of the receptor. Ligand binding induces conformational changes in EGFR that allow the receptor to homodimerize or to heterodimerize with other ErbB family members such as ErbB2 (HER2). Recent structural studies (Garrett et al., Cell 110: 763-73, 2002; Ogiso et al., Cell 110: 775-87, 2002; Ferguson et al., Mol Cell 11: 507-17, 2003; Hubbard, Cancer Cell 7: 287-8, 2005) have elucidated the molecular details of these conformational changes, demonstrating that the protein shifts from a tethered form, which binds ligand with low affinity and in which the dimerization region of the receptor is masked by intramonomer interactions, to an untethered form, which binds ligand with high affinity and in which the dimerization region is exposed and available for interaction with an additional monomer. Dimerization leads to internalization of the receptor and cell signaling stimulating cell proliferation.

Aberrant EGFR signaling has been implicated in tumor growth and progression (reviewed in Baselga et al., 28, 2000). Studies showed that overexpression of EGFR can lead to cell transformation in culture. Subsequently, numerous tumor types including colon, prostate, non-small cell lung, and breast cancer have been found to overexpress EGFR. EGFR overexpression is associated with poor clinical outcome, including non-responsiveness to chemotherapy, poor prognosis, metastasis, and reduced patient survival. Overexpression of EGFR-binding ligands often accompanies EGFR overexpression, suggesting that autocrine signaling through EGFR is important for cancer progression.

Anti-EGFR agents currently in development or on the market include anti-EGFR antibodies and tyrosine kinase inhibitors. Anti-EGFR antibodies, cetuximab (Goldstein et al., Clin Cancer Res 1: 1311-8, 1995; WO9640210) and panitumumab (U.S. Pat. No. 6,235,883) bind to the receptor ectodomain and prevent ligand binding, thereby attenuating dimerization and inhibiting EGFR signaling. In contrast, the kinase inhibitors such as erlotinib and gefinitib (Traxler, Expert Opin Ther Targets 7: 215-34, 2003) bind to the ATP-binding site of the catalytic domain of the receptor and inhibit signaling by blocking intracellular kinase phosphorylation activity. EGFR signal blocking agents have demonstrated clinical activity. However, while many tumors express EGFR, not all tumor growth is dependent on EGFR cascades. Thus, EGFR overexpression can serve as a cancer marker independently of its role in tumor growth.

The latter principle has been the basis for efforts to use EGFR binding antibody conjugates of cytoxins or anti-EGFR antibody fragments to selectively target liposomal drug formulations. While antibody binding fragments have unique specificity and high affinity for their target, they are large, usually heterodimeric structures, best produced by recombinant protein expression systems. Thus, there is a need in the art for easily manipulated, robust EGFR binding moieties with good specificity and affinity amenable to large scale synthetic production.

SUMMARY OF THE INVENTION

In one embodiment, the invention relates to peptides that bind specifically to EGFR. The peptides exhibit one or more properties selected from a) competitive binding with known EGFR ligands, EGF and TGF-α; b) ability to compete with the neutralizing monoclonal antibody cetuximab for binding to EGFR; c) binding to a non-ligand binding domain on EGFR; and d) ability to bind to extracellular domain of EGFR in the presence of EGF.

In one of four embodiments, the peptide of the invention is represented by the consensus sequence comprising:
  i. LCXXΦΦHPLC, where Φ is F or Y (SEQ ID NO: 9) and represented by SEQ ID NOs: 6-8 (CNL5 Library, Table 4);
  ii. SLPXLLC (SEQ ID NO: 22) and represented by SEQ ID NOs: 10-21 (S15 Library, Table 5);
  iii. DC(I/V)XFGXX(L/V)YC (SEQ ID NO: 36) and represented by SEQ ID NOs: 23-35 (S18 Library, Table 6);
  iv. CXLXXDXXL/IL/IC (SEQ ID NO: 42) and represented by SEQ ID NOs: 37-41 (S19 Library, Table 7); or
  v. XXCXXTXFDXWXVCXX (SEQ ID NO: 50) and represented by SEQ ID NOs: 43-49 (S20 Library, Table 8).

In another embodiment, the peptide of the invention comprises any of the peptides SEQ ID Nos: 6-59.

In another embodiment the sequence of the peptide is DPCTWEVWGRECLQ (SEQ ID NO: 55).

The peptides of the invention are used in pharmaceutical compositions to target cytotoxic compounds to inhibit unwanted growth of cells that overexpress EGFR such as neoplastic cells. The EGFR-targeting peptides of the invention can be used individually, that is, where all peptides are of a single composition, or may be used in mixtures where more than one peptide sequence is present in the composition. The peptides may be used in various pharmaceutical preparations as the free peptides or as components of more complex structures such as conjugated directly to an active, such as a cytotoxin, or conjugated to polymeric and/or lipid structures capable multivalent binding and, optionally, further capable of incorporating an active.

In one embodiment, a composition is described, comprising liposomes comprised of (i) vesicle-forming lipids; (ii) a lipopolymer; (iii) a conjugate comprised of a hydrophobic moiety, a hydrophilic polymer, and a peptide as described herein; and (iv) an entrapped drug.

In another embodiment, a formulation is described, comprising liposomes comprised of (i) at least one rigid vesicle-forming lipid; (ii) a lipopolymer comprised of a hydrophobic moiety and polyethylene glycol; (iii) a conjugate comprised of a hydrophobic moiety, polyethylene glycol, and a peptide that exhibits specific affinity of binding for human EGFR having the amino acid sequence of the formula: DPCTW-EVWGRECLQ (SEQ. ID. No. 55), wherein the C residues are engaged in a disulfide bond; and (iv) an entrapped drug having anti-tumor activity.

In another embodiment, a method of preparing a liposomal composition is described, wherein the peptides are inserted into hydrophilic polymer surface coated liposomes loaded with the cytotoxic agent by chemically modifying the peptide for insertion or direct conjugation to pre-formed liposomal structures.

In an alternative embodiment, the peptides may be used to construct a fusion protein having desirable therapeutic characteristics such as extended serum half-life and reduced elimination as compared to the peptide alone. One embodiment of a peptide-fusion protein comprises domains from a human antibody Fc region, e.g. a "mimetibody". The Fc-portion of the fusion protein provides an additional site for chemically modifications such as the conjugation of cytotoxic molecules. Additionally, the Fc portion of a human IgG is able to impart non-antigen binding immunoglobulin functions of antibodies to the construct, such as the ability to activate complement, bind Clq, and enhance target cell killing through antibody directed cell cytoxicity (ADCC) when such properties are desired in the profile of a therapeutic product comprising a peptide of the present invention.

BRIEF DESCRIPTION OF THE SEVERAL VIEWS OF THE DRAWING

FIGS. 2A and B shows binding isotherms for interaction of EGF with sEGFR-His6. Equilibrium binding data for three experiments are shown.

FIGS. 7A-E are column graphs showing the relative binding specificity profiles of selected phage from pIX libraries: binding of representative clones, EGF-displaying phage, and the parent phagemid vector pPEP9 are given.

FIGS. 8A-C are FACS generated histograms showing binding of various phage species to PP145 and PP146 phage to either (A & B) A431 cells, a tumor line overexpressing EGFR or C) a comparison of A431 cell binding and MCF-7 cell binding (MCF-7 are EGFR−). A431 were incubated with PP145, 146, M13KE-phage as a negative control, or pIII EGF-phage as a positive control, and bound phages were detected with a mouse anti-phage-FITC antibody: Solid peak is phage alone; Trace is phage+anti-phage-FITC; other controls are anti-phage-FITC alone which is shown as a trace over or close to the solid phage peak in (A); in (B) and (C), Bbs 1.1 is a negative and pIX EGF-phage represents a positive control.

FIG. 10 shows the FACS results for binding of aviding-biotin complexes of biotin-PEG-P190 at the three concentrations noted to A431 cells in the absence (A) or presence (B) of EGF.

BRIEF DESCRIPTION OF THE SEQUENCE LISTING

Figure 1:
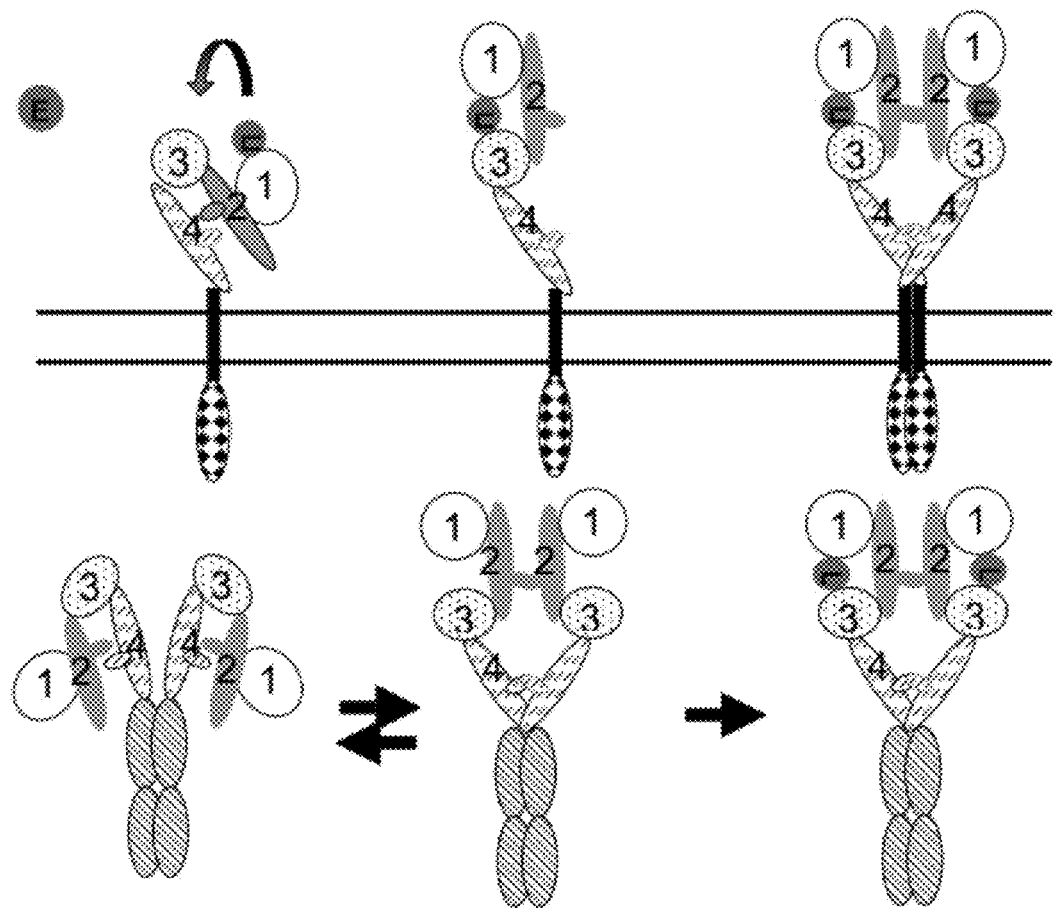
FIG. 1 shows diagrammatically, how the four domains of the extracellular region of EGFR interact with each other and with an activating ligand, EGF. The upper series is the EGFR as it occurs on the cell plasma membrane. The lower series represent the construct, sEGFR-MMB, used in the present invention to select EGFR binding proteins.

| SEQ ID No: | Description | Type | Length | Subdomains & Features |
|---|---|---|---|---|
| 1 | Human extracellular EGFR-His6 (sEGFR-His6) | aa | 627 | 1-164 I L (leucine rich) 165-309 II CR (cysteine-rich_ 310-479 III L-type 480-621 IV CR 622-627 His$_6$ |
| 2 | sEGFR-MMB | aa | 870 | 1-3 hu Ig Var domain-derived 4-624 sEGFR 625-630 Flexible Linker 631-638 human J domain 649-653 human IgG1 hinge 654-870 C2 and C3 domains of human IgG1. |
| 3 | Control-MMB (CNTO 360) | aa | 202 | 1-3 hu Ig Var domain-derived 4-13 human J-derived 14-28 human IgG1 hinge 29-202 C2 and C3 domains of human IgG1 |
| 4 | Cloning primer for sEGFR, fwd | nt | 43 | |
| 4-5 | Cloning primer for sEGFR, reverse | nt | 27 | |

PEPTIDE LIST

| SEQ ID NO: | Library | Name | SEQUENCE |
|---|---|---|---|
| 6 | pIII CNL5 | PP143 | VLCSNFYHPLCHS |
| 7 | pIII CNL5 | PP145 | VLCHRYYHPICYT |
| 8 | pIII CNL5 | PP146 | TLCRSFFHPLCYA |
| 9 | PIII CNL5 consensus | | LCXXΦΦHPLC, where Φ is F or Y |
| 10 | S15 | | YRLFVDESIFFCTRL |
| 11 | S15 | | ELGLPTLLCWPTDTL |
| 12 | S15 | | VSGILPILVCHPAAT |
| 13 | S15 | PP175 | LPDDSLPELICKVRG |
| 14 | S15 | | HVSLQSLPELICVVS |
| 15 | S15 | | NWFSLPTLLCFPLNP |
| 16 | S15 | | STITSLPTLQCWPIL |
| 17 | S15 | | PIDDESLPVLYCVTS |
| 18 | S15 | | PIFSSLPVLYCTSQL |
| 19 | S15 | | GADTLPDLLCWESSL |
| 20 | S15 | | TVFTLPELVCVVAGT |
| 21 | S15 | | LPDLICAVDSGTSGA |
| 22 | S15 CONSENSUS | | SLPXLLC |
| 23 | S18 | | AGCIAFVDVVYCAR |
| 24 | S18 | | AKCIAFGNSVYCLN |
| 25 | S18 | | RDCIIFDKTVYCVI |
| 26 | S18 | | KHCILFEKTVYCAK |
| 27 | S18 | | DSCIQFANLLYCAI |
| 28 | S18 | | TDCIRFGVLWYCLV |
| 29 | S18 | | RACITFGKVVYCEV |
| 30 | S18 | | AYCSFVAGDLVCQV |
| 31 | S18 | PP173 | TDCVIFGLETYCLR |
| 32 | S18 | | SDCVLFGSKLFCSA |
| 33 | S18 | | TDCVRFGETIYCIV |
| 34 | S18 | | YDCVSFGAVAYCPQ |
| 35 | S18 | | RGCVVFGDNIYCIV |
| 36 | S18 CONSENSUS | | DC(I/V)XFGXX(L/V)YC |
| 37 | S19 | PP180 | MICYLVDSGNIICYK |
| 38 | S19 | | YDCMIRADGSLICWC |
| 39 | S19 | PP179 | GPCVLIRDYYLLCLE |
| 40 | S19 | | AFCRLDFNQWLTCLV |
| 41 | S19 | | CDCREAVSASLVCRY |
| 42 | S19 CONSENSUS | | CXLXXDXX(L/I)(L/I)C |
| 43 | S20 | | PTCDSATRRVLTICAD |
| 44 | S20 | | WMCFLEGYGASLMCQC |
| 45 | S20 | | DSCCSFLTDGTVVCSL |
| 46 | S20 | | YICTPSDIDSWYICYL |
| 47 | S20 | | SVCVGTAFPGWMVCGP |
| 48 | S20 | PP176 | KTCVSTTFDLWFVCFA |
| 49 | S20 | | LLCATTSFRDWFVCFT |
| 50 | S20 CONSENSUS | | XXCXXTXFDXWXVCXX |
| 51 | S16 | PP174 | SGCLDALWQCVY |
| 52 | S16 | PP177 | DACTMVFLWCSL |
| 53 | S17 | PP178 | RWCYFWWITICEL |
| 54 | S18 | PHPEP189 | MFCFRWYAGWSCVS |
| 55 | S18 | PHPEP190 | DPCTWEVWGRECLQ |
| 56 | CNL1-11 | PHPEP191 | HFYPTKTPGY |
| 57 | CNL1-11 | PHPEP192 | AASRALWAFNSD |
| 58 | CNL1-11 | PHPEP193 | SYYWGYTVDIRR |
| 59 | CNL1-11 | PHPEP194 | SECFPLAPDWLSCIL |
| 60 | | P190-MMB | Fusion protein construct incorporating P190, a flexible linker, and human IgG derived domains. |

DETAILED DESCRIPTION OF THE INVENTION

Abbreviations

Abs antibodies, polyclonal or monoclonal; DSPE distearoylphosphatidylethanolamine; EGF epidermal growth factor; EGFR epidermal growth factor receptor; FACS fluorescence activated cell sorting; Ig immunoglobulin; Mab monoclonal antibody; PEG polyethylene glycol; TGFalpha transforming growth factor alpha; sEGFR soluble (extracellular domain) of EGFR; MMB MIMETIBODY™; DPBS, Dulbecco's phosphate buffered saline without calcium chloride or magnesium chloride; SEC, size exclusion chromatography; SLS, static light scattering; BSA, bovine serum albumin; MM, molecular mass; MW molecular weight; RI, refractive index, b-biotinylated; SPA succinimidyl proprionate; TBST tris buffered saline with 0.05% Tween.

DEFINITIONS

All amino acids, unless otherwise specified, are taken be the naturally occurring L-isomeric form of the alpha-amino acid. Peptides, unless otherwise specified, are taken to comprise the naturally occurring L-amino acid forms.

As used herein "receptor activation" is characterized by the ability of a receptor to generate an intracellular signaling event or characterized by increased signaling activity relative to receptor that is not activated. Activated receptor tyrosine kinases (RTKs), for example, exhibit elevated levels of tyrosine kinase activity compared to RTKs that are not activated. Activation typically includes oligomerization, e.g., dimerization, trimerization, etc., into higher order receptor complexes. Complexes may comprise a single species of protein, i.e., a homomeric complex. Alternatively, complexes may comprise at least two different protein species, i.e., a heteromeric complex. Events leading to formation of activated cell surface receptor complexes may include ligand binding or caused by, for example, overexpression of normal or mutant forms of receptor on the surface of a cell. Receptor activation is, in many instances, accompanied by other events such as autophosphorylation and induction of a tyrosine kinase cascade, leading ultimately to DNA synthesis and cell division. In addition, receptor activation may be preceded or followed by cellular migration of the receptor or receptor complex, such as by internalization, recycling, or intracellular degradation.

The term "erbB" refers to receptors in the erbB family of receptor tyrosine kinases which assemble into hetero- or homodimers, including, but not limited to, erbB1 (EGFr, epidermal growth factor receptor, HER1), erbB2 (neu, p185, HER2), erbB3 (HER3), and erbB4 (HER4). As used herein, the term "EGFR" is meant human epidermal growth factor receptor, ERBB1, HER1, a member of the receptor tyrosine kinase family involved in the regulation of cellular proliferation and differentiation. Human EGFR is designated E.C. 2.7.10.1 and represented in the NCBI record Accession No. NP_005219 as isoform A being 1210 amino acids in length. The epidermal growth factor receptor gene (c-erb-1), located on human chromosome 7, is homologous to the avian erythroblastosis virus oncogene (v-erbB) that induces malignancies in chickens. The v-erbB gene encodes for a truncated protein product that lacks the extracellular ligand binding domain. The tyrosine kinase domain of the epidermal growth factor receptor has been found to have 97% homology to the v-erbB transforming protein.

The term "Kdis" or "$K_D$," or "Kd' as used herein, is intended to refer to the dissociation rate of a particular ligand-receptor interaction. The "$K_D$", is the ratio of the rate of dissociation ($k_2$), also called the "off-rate ($k_{off}$)", to the rate of association rate ($k_1$) or "on-rate ($k_{on}$)". Thus, $K_D$ equals k2/k1 or $k_{off}/k_{on}$ and is expressed as a molar concentration (M). It follows that the smaller $K_D$, the stronger the affinity of binding. Therefore, a $K_D$ of $10^{-6}$M (or 1 μM) indicates weak binding affinity compared to a $K_D$ of $10^{-9}$ M (or 1 nM). $K_D$ values may be obtained empirically by, for example, measuring the concentration of ligand required to half-saturate the number of targets.

By a peptide that "specifically binds to EGFR" is refers to a peptide wherein the binding affinity, e.g. $K_D$, for EGFR is stronger than for other members of the erbB family of receptor tyrosine kinases, other growth factor receptor tyrosine kinases, and any other family of proteins generally. A ligand or peptide which "specifically binds" a receptor or peptide specific for EGFR means that the affinity is at least twice as great for that receptor than any other receptor or protein, or mathematically, the $K_D$ of the peptide for the receptor for EGFR is at least two-fold lower than the $K_D$ of the peptide for another receptor.

ERBB Receptors

Epidermal growth factor receptors comprise erbB1 (EGFr, epidermal growth factor receptor, HER1), erbB2 (neu, p185, HER2), erbB3 (HER3), and erbB4 (HER4). ErbB receptors consist of an approximately 620-amino acid extracellular region followed by a single transmembrane-spanning region and a cytoplasmic kinase domain. The extracellular regions of ErbB receptors are made up of four domains arranged as a tandem repeat of a two-domain unit consisting of an approximately 190-amino acid L (large or leucine-rich) domain followed by an approximately 120-amino acid CR (cysteine-rich) domain. Thus, domains I and III are L-domains which exhibit helical structure, and domains II and IV are CR-domains with extended repeats of seven small disulfide-containing modules. The first three of these domains share 15 to 20% sequence identity with the first three domains of the type I insulin-like growth factor receptor (IGFR). However, whereas an $NH_2$-terminal three-domain fragment of EGFR binds ligand with high affinity, IGFR does not, indicating that ErbB receptors and IGFR not only interact with different ligands but also use different binding modes.

The form of the EGFR (ERBB1) extracellular domain exhibiting intramolecular interaction between domains II and IV has been termed the "tethered" configuration of the molecule and has reduced affinity for natural ligands. Referring to FIG. 1, top panel, the tethered or internally folded domains of an EGFR receptor are shown on the left; binding the natural ligand, EGF, causes a conformational change leading to "untethering" of the extracellular domain (middle figure); and the ability for the EGFR to homodimerize (right figure). It was observed (Ullrich, A and Schelssinger, J. 1990 Cell 61: 203-212) that EGFR displayed on the cell surface binds ligand with high affinity ($K_D$<0.1 nM) by about 2-5% of receptors or lower affinity ($K_D$ 6-12 nM), however, understanding how the domain structures contribute to conformations with altered affinity or activation status is not completely understood (Burgess, et al. 2003 Mol Cell 12:541-552). Studies using mutational analysis or truncated forms of monomeric sEGFR (extracellular EGFR) have been able to affect an approximate 3- to 26-fold increase in affinity of ligand binding when regions of domain IV are altered. Any of these alterations leads to disruption of the tethered conformation of the receptor (Dawson et al. 2005. Mol Cell Biol. 25:7734-7742). One such construct is EGFR501; spanning domains I, II, and III and the first three small disulfide-containing modules of domain IV (U.S. Pat. No. 6,946,543; Elleman et al. 2001 Biochemistry 40: 8930-8939). When such mutations and deletions were incorporated into the full-length receptor for functional characterization, it was confirmed that the mutations that disrupt the potential for the molecule to form the intramolecular tether, do not cause constitutive activation, dimerization or enhanced EGF ligand sensitivity. On the other hand, the naturally occurring variant of EGFR known as varIII or de2-7 which has a single glycine residue in place of the normal residues 6 to 273 (domain I and most of domain II) and displays constitutive tyrosine kinase activity (Lorimer, I A J. 2002. Curr Cancer Drug Targets 2002 (2):91-102).

Further, the region located between the transmembrane and kinase domains has been designated the "juxtamembrane domain" (JX), and presumed to impart various properties related to receptor trafficking to the receptor. Receptor trafficking functions include basolateral sorting signals, a lysosomal sorting motif, a nuclear localization signal, as well as binding sites for calmodulin, alpha-subunits of heterotrimeric Gs proteins, and phosphoinositide kinases. The JX region also includes post-translational modification sites; Thr654 is a known substrate for PKC, and Thr669 and Ser671 are substrates for MAPK (Choowongkomon™, K et al. J. Biol. Chem., 280(25): 24043-24052, Jun. 24, 2005). EGFR may either be degraded or recycled once internalized into the cell, the fate of the internalized receptor may have to do with the type of ligand bound and the level of receptor expression on the cell surface. Upon ligand binding, EGFR kinase is activated the receptor is internalized through clathrin-coated pits.

It is generally understood that EGFR receptor internalization requires dimerization and activation. Thus, use of the EGFR as a target for intracellular delivery of cytotoxin molecules is reasoned to involve at least a dimeric form of EGFR which may further comprise an untethered or "high affinity" binding conformation of EGFR extracellular domains (FIG. 1).

Therefore, and based on the aforementioned literature, applicants chose to construct a dimeric sEGFR for the purpose of selecting a peptide ligand suitable for use as a drug targeting moiety for EGFR expressing cells, such as tumor cells. The construct includes the entire extracellular domain of human EGFR fused to human immunoglobulin constant regions (the domains constituting the Fc domain, SEQ ID NO: 2) and is shown in graphic forms and various configurations in the lower panel of FIG. 1. The expressed purified construct, sEGFR-MMB, was found to be a homodimer with an unexpectedly high affinity for the natural EGFR ligands EGF and TGFalpha. The observed $K_D$ for EGFR was 0.177 nM and for TGFalpha, 3 nM as compared to the $K_D$ of binding to a monomeric sEGFR form by the same criteria of 65 nM for EGF and 371 nM for TGFalpha representing a 360-fold and 124-fold increase in affinity for these ligands, respectively. As the $K_D$ of sEGFR-MMB for EGF is comparable to the $K_D$ previously reported (Ullrich, 1990 supra) for the high affinity binding population on cell surfaces, the reagent was deemed an appropriate reagent for selection of agents capable of binding EGFR on the cell surface.

Selection of EGFR Targeting Peptides

As described above, EGFR is a plasma membrane protein, having a transmembrane domain and further comprising internal domains capable of being phosphorylated and interacting with signal transduction pathway proteins. Thus, the entire protein does not exist in native form in aqueous solution. It was therefore desirable to create a soluble reagent comprising the extracellular domains of the protein, sEGFR (SEQ ID NO: 1). Residues 1-621 of SEQ ID NO: 1 which are extracellular residues of the mature chain of human EGFR.

Dimeric Constructs and Reagents

Applicants co-pending applications WO04/002417; WO04/002424; WO05/081687; and WO05/032460 describe a structure referred to herein as a MIMETIBODY™ (MMB) structure, each of which references are entirely incorporated herein by reference, and which structures are included in a ligand binding partners with immunglobulin domains of the present invention, and which can include CDR-, CH1-deleted and/or hinge deleted mimetibodies as described in these and similar references and as otherwise known in the art.

In a typical embodiment an Fc-containing fusion protein or MMB comprises formula (I) which is absent the immunoglobulin CH1 domain:

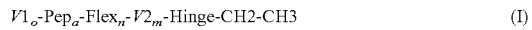

$$V1_o\text{-Pep}_a\text{-Flex}_n\text{-}V2_m\text{-Hinge-CH2-CH3} \quad (I)$$

where Pep represents a bioactive peptide or polypeptide capable of specifically recognizing a target, Flex is an optional flexible linker polypeptide that provides structural flexibility by allowing the mimetibody to have alternative orientations and binding properties, V1 and V2 are bracketing sequences, Hinge is at least a portion of an immunoglobulin hinge region, CH2 is at least a portion of an immunoglobulin CH2 constant region, CH3 is at least a portion of an immunoglobulin CH3 constant region; m, n and o can be zero or can be an integer between 1 and 10, and a can be an integer from 1 to 10. In one embodiment, the CH2 and CH3 domains are derived from a human germline IgG4 sequence so as to minimize effector functions or may comprise variants with no effector function. In another embodiment the CH2 and CH3 may be derived from a human IgG1 sequence, e.g. a sequence according to NCBI Accession No. P01857 residues 152 to 330.

The Pep sequence can optionally include of sequences for the purposes or stabilization or any number of biophysical functions. In a typical embodiment, the bracketing sequences are derived from an antibody variable (V) domain such as a Vh framework and V1 is the sequence QIQ and V2 represents a sequence derived from an immunoglobulin J gene domain and is TLVTVSS (SEQ ID NO:61). In one embodiment of the present invention, Pep is the extracellular domain of human EGFR (sEGFR) and the V1 is QIQ, V2 is the present, the hinge C2 and C3 are derived from a human $IgG_1$ with each of a, m, n and o equal to 1 (SEQ ID NO. 2). Fusion proteins, such as MMBs, which incorporate an Ig hinge domain naturally, upon expression and secretion from a host cell, form homodimeric structures joined by disulfide bonding of the hinge cysteine residues. Thus, the dimeric structure formed from the construct described (SEQ ID NO: 2) and designated sEGFR-MMB, is bivalent for EGF binding, mimicking a homodimeric receptor conformation at the cell surface (FIG. 1 lower panel).

In another embodiment of a MIMETIBODY, Pep in formula I may be an EGFR-binding peptide of the invention and the expressed construct will be homodimer which is bivalent for EGFR-binding.

Other Constructs

Alternative scaffolds, that is other than the folded loops of the typical immunoglobulin variable domain which display the hypervariable (CDR) regions responsible for antibody binding specificity and affinity, can be employed to display the EGFR-peptides of the invention. The use of so-called protein scaffolds for the generation of novel binding proteins via combinatorial engineering has recently emerged as a powerful alternative to natural or recombinant antibodies (P Nygren, A Skerra. 2004 J Immunol Meth 290: 3-28 and H Kaspar Binz, P Amstutz, A Plückthun. 2005. Nature Biotechnol 23: 1257-1268).

Globular proteins or proteins with globular domains suitable for use as scaffolds which have been investigated include fibronectin, ankryin, C-type lectins, cytotoxic T-Lymphocyte Associated protein-4 (CTLA-4), and lipocalins. Fibronectin has several types of ligand binding domains, a preferred domain for use as a scaffold is the type III domain (Fn-III or Fn3). The lipocalin binding site consists of four adjacent loops.

The number of approaches can be classified into three classes: carrier proteins for the display of single variegated loops, scaffolds providing rigid elements of secondary structure, and protein frameworks supporting a group of conformationally variable loops in a fixed spatial arrangement. The construction of these artificial binding proteins is ideally suited to monomeric and small polypeptides such as the EGFR-binding peptides of the invention.

Peptide Libraries

Phage, ribosome, yeast, and bacterial display libraries are tools for querying large numbers of proteins or peptides. Ribosome display is a method of translating mRNAs into their cognate proteins while keeping the protein attached to the RNA. The nucleic acid coding sequence is recovered by RT-PCR (Mattheakis, L. C. et al. 1994. Proc. Natl. Acad. Sci. USA 91, 9022). Yeast display is based on the construction of fusion proteins of the membrane-associated alpha-agglutinin yeast adhesion receptor, aga1 and aga2, a part of the mating type system (Broder, et al. 1997. Nature Biotechnology, 15:553-7). Bacterial display is based on fusion of the target to exported bacterial proteins that associate with the cell membrane or cell wall (Chen and Georgiou 2002. Biotechnol Bioeng, 79:496-503). The methods, which allow for selection of the whole organism (cell or phage) or protein-ribosome complex, have the advantage that the DNA encoding the polypeptide is isolated at the same time as the binding sequence.

Phage display has become particularly widely used since Smith and coworkers (Smith, 1985 Science, 228:1315-1317 and Parmley and Smith, 1985 Gene, 73:305-318) demonstrated that small protein fragments (10-50 amino acids) can be "displayed" efficiently on the surface of filamentous phage by inserting short gene fragments into gene III of the fd phage ("fusion phage"). These fusion phage have proved useful for displaying short mutated peptide sequences for identifying peptides that may react with antibodies (Scott et al., 1990 Science 249:386-390 and Cwirla et al., 1990 Proc. Natl. Acad. U.S.A. 87:6378-6382) or a foreign protein (Devlin et al., 1990 Science, 249:404-406). Filamentous bacteriophage fd, and similarly M13, consists of a circular, single-stranded DNA molecule surrounded by a cylinder of coat proteins. There are about 2700 molecules of the major coat protein pVIII that envelope the phage. At one end of the particle, there are five copies each of pIII and pVI that are involved in host-cell binding and in the termination of the assembly process. The other end contains five copies each of pVII and pIX that are hydrophobic peptides of 33 and 32 amino acids, respectively, required for the initiation of assembly and for maintenance of virion stability. Strategies for peptide fusion libraries of the various coat proteins have been explored, including the pIX coat protein (see U.S. Pat. No. 6,472,147 and Gao, et al. 2002 Bioorg. Med. Chem. 10: 4057-4065 both incorporated entirely by reference).

Generally, the peptides which bind to selected targets are identified by screening libraries which encode a random or controlled collection of amino acid sequences. Peptides encoded by the libraries are expressed as fusion proteins of bacteriophage coat proteins, and bacteriophage are then screened against the targets of interest. Peptides having a wide variety of uses, such as therapeutic or diagnostic reagents, may thus be identified without any prior information on the structure of the expected ligand or target receptor.

While phage libraries simplify the retrieval of genetic material associated with functional attributes, e.g. binding, multistep panning strategies are required to isolate the best candidate from the library. The use of phage displayed peptide libraries was used in exemplified methods of the present invention and with unique reagents expressly created for the directed panning. In a particular embodiment, libraries of randomized circular peptides i.e. those comprising gapped cysteine residue pairs were screened for binders to EGFR.

Synthesis of EGFR Targeting Peptides

The EGFR targeting peptides of the invention and constructs comprising the peptides are amenable to manufacture by chemical synthesis or by recombinant protein expression using a host cell (a cell artificially engineered to comprise nucleic acids encoding the sequence of the peptide and which will transcribe and translate, and, optionally, secrete the peptide into the cell growth medium). For recombinant production process, a nucleic acid coding for the amino acid sequence of the peptide would typically be synthesized by conventional methods and integrated into an expression vector. Such methods are particularly preferred for manufacture of the polypeptide compositions comprising the peptides fused to additional polypeptide sequences or other proteins or protein fragments or domains. The host cell can optionally be at least one selected from E. Coli, COS-1, COS-7, HEK293, BHK21, CHO, BSC-1, Hep G2, 653, SP2/0, 293, HeLa, myeloma, lymphoma, yeast, insect or plant cells, or any derivative, immortalized or transformed cell thereof. Also provided is a method for producing at least one peptide, comprising translating the peptide encoding nucleic acid under conditions in vitro, in vivo or in situ, such that the peptide is expressed in detectable or recoverable amounts. The techniques well known in the art, see, e.g., Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989).

Chemical synthesis of peptides is routinely performed methods well known to those skilled in the art for either solid phase or solution phase peptide synthesis. For solid phase peptide synthesis, so called tBoc (tert-Butyl oxy carbonyl) and Fmoc (Fluorenyl-methoxy-carbonyl) chemistry, referring to the N-terminal protecting groups, on polyamide or polystyrene resin have become the conventional methods (Merrifield, R B. 1963 and Sheppard, R C. 1971, respectively). Unlike ribosomal protein synthesis, solid-phase peptide synthesis proceeds in a C-terminal to N-terminal fashion. The N-termini of amino acid monomers is protected by these two groups and added onto a deprotected amino acid chain. Deprotection requires strong acid such as trifluoroacetic acid for tBoc and base such as piperidine for Fmoc. Stepwise elongation, in which the amino acids are connected step-by-step in turn, is ideal for small peptides containing between 2 and 100 amino acid residues.

Liquid phase methods (often referred to as solution phase methods) of synthesis carry out all reactions in a homogeneous phase. Successive amino acids are coupled in solution until the desired peptide material is formed. During synthesis, successive intermediate peptides are purified by precipitation and/or washes. Peptides and amino acids from which peptides are synthesized tend to have reactive side groups as well as reactive terminal ends. When synthesizing a peptide, it is important that the amino group on one peptide react with the carboxyl group on another peptide. Undesired reactions at side groups or at the wrong terminal end of a reactant produces undesirable by-products, sometimes in significant quantities. These can seriously impair yield or even ruin the product being synthesized from a practical perspective. To minimize side reactions, it is conventional practice to appropriately mask reactive side groups and terminal ends of reactants to help ensure that the desired reaction occurs.

The major advantage of solution peptide synthesis is the availability of a multitude of coupling methods, a wide variety of protecting groups, opportunities for intermediate purification and the potential for linear scale up. In planning solution synthesis the strategy considerations include: (1) selection of main chain and side chain protective groups; (2) choice of activation method; (3) deprotection methods; (4) selection of segments in efforts to minimize racemization during segment condensation; and (5) solubility considerations. Conventional solution peptide synthesis is cumbersome and time consuming, but it allows purification of fully protected intermediates. This is an advantage over solid phase peptide synthesis (SPPS), in which case the final product has to be isolated from a mixture of similar fragments.

The most commonly employed methods for peptide bond formation in solution include: the carbodiimide method (DCC, DIC), symmetric or mixed anhydrides, active esters (OPfp, Odhbt, OSu), phosphonium salts (BOP, PyBOP, AOP, PyAOP) and uronium/guanidinium-mediated salt build around processes using HOBt and HAOt (HBTU, HATU, HBPyU, etc).

For the final deprotection, several options for deprotection reaction processes are shown below and include (a) catalytic hydrogenolysis using molecular hydrogen and palladium ($H_2$/Pd) or catalytic transfer hydrogenolysis; (b) reduction with metallic sodium in liquid ammonia and (c) or reaction with strong acids using halogenated acids or hydrohalogenic acids, e.g. hydrobromic acid in acetic acid (HBr/AcOH) or liquid HF, $BBr_3$/DCM, TFA/thioanisole and sulfonic acids.

Compositions Comprising EGFR Targeting Peptides

The EGFR-targeting peptides of the invention can be used individually, that is, where all peptides are of a single composition, or may be used in mixtures where more than one peptide sequence is present in the composition. The peptides may be used in various pharmaceutical preparations as the free peptides or as components of more complex structures such as conjugated directly to an active, such as a cytotoxin, or conjugated to polymeric and/or lipid structures capable of multivalent binding and, optionally, further capable of incorporating an active.

In one embodiment, the peptides of the invention can be incorporated into a fusion protein as described herein above as a MMB, and which, when expressed and secreted from a host cell form dimeric, bivalent structures having the characteristics imparted by the human immunoglobulin constant domains. Such proteins generally have been found to have long circulation plasma half-lives (Capon et al. 1989 Nature 337:525-530). Further, the proteins can be further linked to other polypeptides or molecules by association or covalent linkage, such as, but not limited to, a Cys-Cys disulfide bond or derivatization of one or more amino acid side chains. Particularly useful in this regard are the epsilon amino groups of lysines.

Toxin Conjugates

Cytotoxins, metabolic poisons, such as agents that disrupt or stabilize microtubule formation, or those that cause blocks and breaks in the DNA, although not specific for tumor cells have long been used as antineoplastic therapy. Using the peptides of the invention to deliver such an agent to the actively proliferating tumor cell would be advantageous. Therefore, the attachment of the toxin to the peptide in a peptide-toxin conjugate represents a general formula comprising the peptides of the invention. Highly potent toxin may be delivered to EGFR expressing cells, and particularly those cells on which EGF ligand is bound. The cytotoxin may be selected from the group consisting of maytansinoids, calicheamicins, epothilones, discodermolide, eleuthrobins, dolastatins, cryptophycins, camptothecins, rhizoxin (CAS reg. no. 90996546), or taxane derivatives and such other compounds that exhibit half maximal inhibition (IC50 or GI50) of on tumor cell growth at $10^{-9}$ M or less.

Conjugates of the peptides of the invention and toxic compound can be formed using any techniques presently known or later developed. When the linkage to the toxin causes the biological activity of the toxin to be masked as in a proform, a cleavable linkage may be desirable. For example, the cytotoxic compound can be modified to yield a free amino group and then linked to the antibody molecule via an acid-labile linker, or a photolabile linker. The toxic compound can be condensed with one or more amino acids and subsequently linked to an antibody molecule to produce a peptidase-labile linker. Alternatively, the toxic compound can be treated to yield a primary hydroxyl group, which can be succinylated and linked to an antibody molecule to produce a conjugate that can be cleaved by intracellular esterases to liberate free drug.

Linkers comprising intracellularly cleavable bonds include acid-labile linkages such as cis-aconityl linkages, esters, acid-sensitive hydrazone linkages, lysosomally degradable peptide linkers, hydrolase cleavable linkers, peptidase or protease specific linkers, and disulfide (sulfhydryl) linkers (see Dyba, M., et al. 2004 Curr Pharm Design 10:2311-2334 for a review). By being capable of more rapid or selective cleavage under intracellular conditions versus the conditions predominating in, for example, the circulation, the linker imparts further specificity and safety to the overall pharmacodynamics of the conjugate. Disulfide linkages are particularly preferred because of the favorable reduction potential within the cellular compartments as well as inducible redox enzyme activation (Saito, G. et al. Adv. Drug Delivery Rev 2003 55:199-215). In one embodiment of the invention, the bond is between a sulfur atom present in the peptide, e.g. in an appended or fused region comprising a cysteine residue, and another sulfur atom present in the toxic compound. In another embodiment, the linking moiety consists of one or more atoms or chemical groups.

In order to create the disulfide linkage between a peptide of the invention and the cytotoxin, preferably, the toxic compound is treated to create a free or protected thiol group, and then one or many disulfide or thiol containing toxic compounds are covalently linked to the peptide or a fusion protein comprising the peptide via disulfide bond(s). The disulfide bond need not be formed directly with a free thiol of the peptide but can be formed by derivatization of any reactive group introduce a site for disulfide exchange, for example, as by coupling a bifunctional linker to free amine group in, e.g. a polypeptide, which is fused or linked to the EGFR-targeting peptide of the invention prior to or after processing to affect the conjugation of the toxin. For example, polypeptides comprising a free cysteine can be modified with crosslinking reagents such as N-succinimidyl 3-(2-pyridyldithio)propionate (SPDP), 4-succinimidyl-oxycarbonyl-a-methyl a-(2-pyridyldithio)-toluene (SMPT), N-succinimidyl-3-(2-pyridyldithio)-butyrate (SDPB), N-succinimidyl-4-(2-pyridyldithio)pentanoate (SPP), N-succinimidyl-5-(2-pyridyldithio)pentanoate, 2-iminothiolane (IT), or acetylsuccinic anhydride by known methods.

Modification of Peptides

The chemical modification of proteins in order to gain longer in vivo circulation time has typically relied upon methods of addition of one or more PEG moieties of several thousand Daltons. Other hydrophilic polymers may also be used and examples are given below. A variety of methods are available for linking PEG and other substituents to proteins. Very often the epsilon-amine of the lysine side chain or the single alpha amino group at the N-terminus are used as the site of modification due the reactive nature of a primary amine (Zalipsky and Lee. 1992. In: Poly(ethylene glycol) Chemistry: Biotechnical and Biomedical Applications, J. M. Harris, ed. Plenum, New York, N.Y., pp. 347-370). Amine-reactive groups include electrophilic groups such as tosylate, mesylate, halo (chloro, bromo, iodo), N-hydroxysuccinimidyl esters (NHS), substituted phenyl esters, acyl halides, and the like.

As discussed above, when linkage of an active or a modifying group to the peptide is desirable, use of a free thiol group in the peptide or attached to the EGFR-binding peptide is an option. Useful thiol reactive reagents include: maleimide, iodoacetyl, acrylolyl, pyridyl disulfides, 5-thiol-2-nitrobenzoic acid thiol (TNB-thiol), and the like.

Urethane (carbamate) attachment of PEG to a protein is another convenient way to form PEG-protein conjugates and carbamate linkages are more resistant to hydrolysis as compared to amide linkages. There are a few known PEG reagents that are used to make urethane linked PEG-proteins, such as slow-reacting imidazolyl formate, trichlorophenyl carbonate, and nitrophenyl carbonates (NPC) derivatives. A more reactive reagent, mPEG-succinimidyl carbonate (mPEG-SC), can also be utilized.

Target Ligand Compositions

In addition to their use in more complex chemically or bioengineered structures, the peptides of the invention or structures or constructs comprising them, may be further formulated for delivery to a subject in need of treatment therewith. For example, the formulation of compounds typically encompasses the use of aqueous liquids optionally buffered or pH adjusted so as to be non-caustic to living tissues and cells. Such methods are generally taught in In: Remington: The Science and Practice of Pharmacy. 20th ed. Baltimore, Md.: Lippincott Williams & Wilkins; 2000. Polypeptide biopharmaceutical preparations often employ co-solvents for stabilization of the three-dimensional structure of the proteins. Such additives include but are not limited to sucrose, trehelose, glycerol, amino acids, inorganic salts, betaine and other components that function in a similar manner as reviewed by Lee, J. C. 2000 Curr Op Biotech 11:81-84.

In a recent report, targeted phage can be used to direct an immune response to a tumor site (Eriksson, et al. 2006 "Tumor specific phage particles promote tumor regression in a mouse melanoma" Cancer Immunol Immunother Pub online September 12). Thus, the phage displaying peptide can function as a therapeutic itself and be administered without cleaving the peptide from the surface of the phage.

The peptides of the invention may also be formulated in complex structures such as liposomes or dendrimers for the purpose of treating a subject.

One of the problems associated with peptide therapeutics is rapid clearance via kidney filtration. One solution to this problem is to increase the size via dendrimers or dendrimer-like structures. Dendrimers are small bifurcating cores. Examples of backbones include lysine as in multiple antigen presenting peptide systems (MAPS), phosphate, silicon, polyamidoamine, syalic acid, and melamine. Dendrimers may be used to present multiple copies of the peptide on the same structure. Multivalent structures display enhanced avidity of binding due to the apparent lower off-rates when binding to a multivalent target, such as as a cell displaying multiple copies of EGFR, which may help overcome the weak affinity common to peptide based binders. The dendrimer is then used to deliver a cytotoxic agent. Alternatively, the multivalent binding side of the dendrimer could be fused to toxins so that multiple toxin molecules are delivered for every peptide. In yet another version, dendrimers with multiple peptides are combined with dendrimers with multiple toxins through reactive groups on the primary groups. For recent reviews see, e.g. Mullaicharam and Hadjichistidis, et. al. 2005 Dendrimers-based drug delivery. Indian Pharmacist (New Delhi, India) 4(42):15-18 and Hadjichristidis, et al. 2005. Synthesis of block copolymers. Adv Polymer Sci. 189 (Block Copolymers I:1-124)

Liposomes as well as other micellar lipid vesicles are included in the methods of the invention for incorporation of the targeting ligand in order to act as drug delivery vehicles. Liposomes are spherical vesicles comprised of concentrically ordered lipid bilayers that encapsulate an aqueous phase. Liposomes serve as a delivery vehicle for therapeutic agents contained in the aqueous phase or in the lipid bilayers. Delivery of drugs in liposome-entrapped form can provide a variety of advantages, depending on the drug, including, for example, a decreased drug toxicity, altered pharmacokinetics, or improved drug solubility. Liposomes when formulated to include a surface coating of hydrophilic polymer chains, so-called Stealth® or long-circulating liposomes, offer the further advantage of a long blood circulation lifetime, due in part to reduced removal of the liposomes by the mononuclear phagocyte system. Often an extended lifetime is necessary in order for the liposomes to reach their desired target region or cell from the site of injection.

Targeted liposomes have targeting ligands, such as the peptides described herein, or affinity moieties attached to the surface of the liposomes. When administered systemically targeted liposomes deliver the entrapped therapeutic agent to a target tissue, region or, cell. Because targeted liposomes are directed to a specific region or cell, healthy tissue is not exposed to the therapeutic agent. Such targeting ligands can be attached directly to the liposomes' surfaces by covalent coupling of the targeting ligand to the polar head group residues of liposomal lipid components (see, for example, U.S. Pat. No. 5,013,556). This approach, however, is suitable primarily for liposomes that lack surface-bound polymer chains, as the polymer chains interfere with interaction between the targeting ligand and its intended target (Klibanov, A. L., et al., *Biochim. Biophys. Acta,* 1062:142-148 (1991); Hansen, C. B., et al., *Biochim. Biophys. Acta,* 1239:133-144 (1995)).

Alternatively, the targeting ligands can be attached to the free ends of the polymer chains forming the surface coat on the liposomes (Allen. T. M., et al., *Biochim. Biophys. Acta,* 1237:99-108 (1995); Blume, G. et al., *Biochim. Biophys. Acta,* 1149:180-184 (1993)). In this approach, the targeting ligand is exposed and readily available for interaction with the intended target.

In one aspect, a liposome composition is provided comprised of liposomes that include as a targeting ligand a peptide as described herein having binding specificity for EGFR. The EGFR targeting ligand is incorporated into the liposomes in the form of a lipid-polymer-peptide conjugate, also referred to herein as a lipid-polymer-ligand conjugate. As will be described below, the peptide has specific affinity for the external domain of the EGRF receptor and targets the liposomes to cells that express EGFR. The following sections describe the liposome components, including the liposome lipids and therapeutic agents, preparation of liposomes bearing an EGFR targeting ligand, and methods of using the liposomal composition for treatment of disorders.

Lipids suitable for use in the composition of the present invention include those comprised of vesicle-forming lipids. Unless otherwise noted, the term "vesicle-forming lipid" refers to any lipid capable of forming part of a stable micelle or liposome composition and typically including one or two hydrophobic, hydrocarbon chains or a steroid group and may contain a chemically reactive group, such as an amine, acid, ester, aldehyde or alcohol, at its polar head group. Such a vesicle-forming lipid is one which (a) can form spontaneously into unilamellar or bilayer vesicles in water, as exemplified by the diglycerides and phospholipids, with its hydrophobic moiety in contact with the interior, hydrophobic region of the bilayer membrane, and its head group moiety oriented toward the exterior polar surface of the membrane, or (b) is stably incorporated into lipid structures, such as cholesterol and its various analogs, including unilammellar, bilayered, or rafts.

The vesicle-forming lipids of this type typically have two hydrocarbon chains, usually acyl chains, and a head group, either polar or non-polar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two hydrocarbon chains are typically between about 14-22 carbon atoms in length, and have varying degrees of unsaturation. The above-described lipids and phospholipids whose acyl chains have varying degrees of saturation can be obtained commercially or prepared according to published methods. Other suitable lipids include glycolipids, cerebrosides and sterols, such as cholesterol.

Cationic lipids are also suitable for use in the liposomes of the invention, where the cationic lipid can be included as a minor component of the lipid composition or as a major or sole component. Such cationic lipids typically have a lipophilic ligand, such as a sterol, an acyl or diacyl chain, and where the lipid has an overall net positive charge. Typically, the head group of the lipid carries the positive charge. Exemplary cationic lipids include 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy) propyl]-N,N,N-trimethylammonium chloride (DOTMA); 3 [N—(N',N'-dimethylaminoethane)carbamoly] cholesterol (DC-Chol); and dimethyldioctadecylammonium (DDAB).

The cationic vesicle-forming lipid may also be a neutral lipid, such as dioleoylphosphatidyl ethanolamine (DOPE) or an amphipathic lipid, such as a phospholipid, derivatized with a cationic lipid, such as polylysine or other polyamine lipids. For example, the neutral lipid (DOPE) can be derivatized with polylysine to form a cationic lipid.

In another embodiment, the vesicle-forming lipid is selected to achieve a specified degree of fluidity or rigidity, to control the stability of the liposome in serum, to control the conditions effective for insertion of the targeting conjugate, as will be described, and to control the rate of release of the entrapped agent in the liposome.

Liposomes having a more rigid lipid bilayer, or a liquid crystalline bilayer, are achieved by incorporation of a relatively rigid lipid, e.g., a lipid having a relatively high phase transition temperature, e.g., up to 60° C. Rigid, i.e., saturated, lipids contribute to greater membrane rigidity in the lipid bilayer. Other lipid components, such as cholesterol, are also known to contribute to membrane rigidity in lipid bilayer structures.

On the other hand, lipid fluidity is achieved by incorporation of a relatively fluid lipid, typically one having a lipid phase with a relatively low liquid to liquid-crystalline phase transition temperature, e.g., at or below room temperature.

The liposomes also include a vesicle-forming lipid covalently attached to a hydrophilic polymer, also referred to herein as a "lipopolymer". As has been described, for example in U.S. Pat. No. 5,013,556, including such a polymer-derivatized lipid in the liposome composition forms a surface coating of hydrophilic polymer chains around the liposome. The surface coating of hydrophilic polymer chains is effective to increase the in vivo blood circulation lifetime of the liposomes when compared to liposomes lacking such a coating.

Vesicle-forming lipids suitable for derivatization with a hydrophilic polymer include any of those lipids listed above, and, in particular phospholipids, such as distearoyl phosphatidylethanolamine (DSPE).

Hydrophilic polymers suitable for derivatization with a vesicle-forming lipid include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and hydrophilic peptide sequences. The polymers may be employed as homopolymers or as block or random copolymers.

An exemplary hydrophilic polymer chain is polyethyleneglycol (PEG), preferably as a PEG chain having a molecular weight between 500-10,000 daltons, more preferably between 750-10,000 daltons, still more preferably between 750-5000 daltons. Methoxy or ethoxy-capped analogues of PEG are also preferred hydrophilic polymers, commercially available in a variety of polymer sizes, e.g., 120-20,000 Daltons.

Preparation of vesicle-forming lipids derivatized with hydrophilic polymers has been described, for example in U.S. Pat. No. 5,395,619. Preparation of liposomes including such derivatized lipids has also been described, where typically between 1-20 mole percent of such a derivatized lipid is included in the liposome formulation (see, for example, U.S. Pat. No. 5,013,556).

As described above, the peptides described herein are covalently attached to the free distal end of a hydrophilic polymer chain, which is attached at its proximal end to a vesicle-forming lipid. There are a wide variety of techniques for attaching a selected hydrophilic polymer to a selected lipid and activating the free, unattached end of the polymer for reaction with a selected ligand, and in particular, the hydrophilic polymer polyethyleneglycol (PEG) has been widely studied (Allen, T. M., et al., Biochemicia et Biophysica Acta, 1237:99-108 (1995); Zalipsky, S., Bioconjugate Chem., 4(4):296-299 (1993); Zalipsky, S., et al. FEBS Lett., 353:71-74 (1994); Zalipsky, S. et al., Bioconjugate Chemistry, 6(6):705-708 (1995); Zalipsky, S., in STEALTH LIPOSOMES (D. Lasic and F. Martin, Eds.) Chapter 9, CRC Press, Boca Raton, Fla. (1995)).

Generally, the PEG chains are functionalized to contain reactive groups suitable for coupling with, for example, sulfhydryls, amino groups, and aldehydes or ketones (typically derived from mild oxidation of carbohydrate portions of an antibody) present in a wide variety of ligands. Examples of such PEG-terminal reactive groups include maleimide (for reaction with sulfhydryl groups), N-hydroxysuccinimide (NHS) or NHS-carbonate ester (for reaction with primary amines), hydrazide or hydrazine (for reaction with aldehydes or ketones), iodoacetyl (preferentially reactive with sulfhydryl groups) and dithiopyridine (thiol-reactive). Synthetic reaction schemes for activating PEG with such groups are set forth in U.S. Pat. Nos. 5,631,018, 5,527,528, 5,395,619, 6,326,353, and the relevant sections describing synthetic reaction procedures are expressly incorporated herein by reference.

It will be appreciated that any of the hydrophilic polymers recited above in combination with any of the vesicle-forming lipids recited above can be employed as modifying agents to prepare the lipid-polymer-ligand targeting conjugate and suitable reaction sequences for any selected polymer can be determined by those of skill in the art.

The methods of preparation and drug loading procedures for liposomes and the others are well-known in the art and various approaches have been described for preparing liposomes having a targeting ligand attached to the distal end of liposome-attached polymer chains. One approach involves preparation of lipid vesicles which include an end-functionalized lipid-polymer derivative; that is, a lipid-polymer conjugate where the free polymer end is reactive or "activated" (see, for example, U.S. Pat. Nos. 6,326,353 and 6,132,763). Such an activated conjugate is included in the liposome composition and the activated polymer ends are reacted with a targeting ligand after liposome formation. In another approach, the lipid-polymer-ligand conjugate is included in the lipid composition at the time of liposome formation (see, for example, U.S. Pat. Nos. 6,224,903, 5,620,689). In yet another approach, a micellar solution of the lipid-polymer-ligand conjugate is incubated with a suspension of liposomes and the lipid-polymer-ligand conjugate is inserted into the pre-formed liposomes (see, for example, U.S. Pat. Nos. 6,056,973, 6,316,024).

Liposomes carrying an entrapped agent and bearing surface-bound targeting ligands, i.e., targeted, therapeutic liposomes, are prepared by any of these approaches. A preferred method of preparation is the insertion method, where preformed liposomes are incubated with the targeting conjugate to achieve insertion of the targeting conjugate into the liposomal bilayers. In this approach, liposomes are prepared by a variety of techniques, such as those detailed in Szoka, F., Jr., et al., *Ann. Rev. Biophys. Bioeng.*, 9:467 (1980), and specific examples of liposomes prepared in support of the present invention will be described below. Typically, the liposomes are multilamellar vesicles (MLVs), which can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

The liposomes can include a vesicle-forming lipid derivatized with a hydrophilic polymer to form a surface coating of hydrophilic polymer chains on the liposomes surface. Addition of a lipid-polymer conjugate is optional, since after the insertion step, described below, the liposomes will include lipid-polymer-targeting ligand. Additional polymer chains added to the lipid mixture at the time of liposome formation and in the form of a lipid-polymer conjugate result in polymer chains extending from both the inner and outer surfaces of the liposomal lipid bilayers. Addition of a lipid-polymer conjugate at the time of liposome formation is typically achieved by including between 1-20 mole percent of the polymer-derivatized lipid with the remaining liposome forming components, e.g., vesicle-forming lipids. Exemplary methods of preparing polymer-derivatized lipids and of forming polymer-coated liposomes have been described in U.S. Pat. Nos. 5,013,556, 5,631,018 and 5,395,619, which are incorporated herein by reference. It will be appreciated that the hydrophilic polymer may be stably coupled to the lipid, or coupled through an unstable linkage, which allows the coated liposomes to shed the coating of polymer chains as they circulate in the bloodstream or in response to a stimulus.

The liposomes also include a therapeutic or diagnostic agent, and exemplary agents are provided below. The selected agent is incorporated into liposomes by standard methods, including (i) passive entrapment of a water-soluble compound by hydrating a lipid film with an aqueous solution of the agent, (ii) passive entrapment of a lipophilic compound by hydrating a lipid film containing the agent, and (iii) loading an ionizable drug against an inside/outside liposome pH gradient. Other methods, such as reverse-phase evaporation, are also suitable.

After liposome formation, the liposomes can be sized to obtain a population of liposomes having a substantially homogeneous size range, typically between about 0.01 to 0.5 microns, more preferably between 0.03-0.40 microns. One effective sizing method for REVS and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin, F. J., in SPECIALIZED DRUG DELIVERY SYSTEMS—MANUFACTURING AND PRODUCTION TECHNOLOGY, P. Tyle, Ed., Marcel Dekker, New York, pp. 267-316 (1990)).

After formation of the liposomes, a targeting ligand is incorporated to achieve a cell-targeted, therapeutic liposome. The targeting ligand is incorporated by incubating the pre-formed liposomes with the lipid-polymer-ligand conjugate, prepared as described above. The pre-formed liposomes and the conjugate are incubated under conditions effective to association with the conjugate and the liposomes, which may include interaction of the conjugate with the outer liposome bilayer or insertion of the conjugate into the liposome bilayer. More specifically, the two components are incubated together under conditions which achieve association of the conjugate with the liposomes in such a way that the targeting ligand is oriented outwardly from the liposome surface, and therefore available for interaction with its cognate receptor. It will be appreciated that the conditions effective to achieve such association or insertion are determined based on several variables, including, the desired rate of insertion, where a higher incubation temperature may achieve a faster rate of insertion, the temperature to which the ligand can be safely heated without affecting its activity, and to a lesser degree the phase transition temperature of the lipids and the lipid composition. It will also be appreciated that insertion can be varied by the presence of solvents, such as amphipathic solvents including polyethyleneglycol and ethanol, or detergents.

The targeting conjugate, in the form of a lipid-polymer-ligand conjugate, will typically form a solution of micelles when the conjugate is mixed with an aqueous solvent. The micellar solution of the conjugates is mixed with a suspension of pre-formed liposomes for incubation and association of the conjugate with the liposomes or insertion of the conjugate into the liposomal lipid bilayers. The incubation is effective to achieve association or insertion of the lipid-polymer-antibody conjugate with the outer bilayer leaflet of the liposomes, to form an immunoliposome.

After preparation, the immunoliposomes preferably have a size of less than about 150 nm, preferably of between about 85-120 nm, and more preferably of between 90-110 nm, as measured, for example, by dynamic light scattering at 30° or 90°.

In one embodiment of the method described herein, the targeted, therapeutic liposome composition of the invention is prepared using pre-formed liposomes and a targeting complex, which are incubated together under conditions effective to achieve insertion of the conjugate into the liposome bilayer. More specifically, the two components are incubated together under conditions which achieve insertion of the conjugate in such a way that the targeting ligand is oriented outwardly from the liposome surface, and therefore available for interaction with its cognate receptor.

Vesicle-forming lipids having phase transition temperatures from approximately 2° C.-80° C. are suitable for use in the pre-formed liposome component of the present composition. By way of example, the lipid distearyl phosphatidylcholine (DSPC) has a phase transition temperature of 62° C. and the lipid hydrogenated soy phosphatidylcholine (HSPC) has a phase transition temperature of 58° C. Phase transition temperatures of many lipids are tabulated in a variety of sources, such as Avanti Polar Lipids catalogue and Lipid Thermotropic Phase Transition Database (LIPIDAT, NIST Standard Reference Database 34).

In one embodiment of the invention, a vesicle-forming lipid having a phase transition temperature between about 30-70° C. is employed. In another embodiment, the lipid used in forming the liposomes is one having a phase transition temperature within a range of 20° C., 10° C. or most typically, 5° C. of the temperature to which the ligand in the targeting ligand avidin-lipid complex can be heated without affecting its binding activity.

It will be appreciated that the conditions effective to achieve insertion of the targeting complex into the liposome are determined based on several variables, including, the desired rate of insertion, where a higher incubation temperature may achieve a faster rate of insertion, the temperature to which the ligand can be safely heated without affecting its activity, and to a lesser degree the phase transition temperature of the lipids and the lipid composition. It will also be appreciated that insertion can be varied by the presence of solvents, such as amphipathic solvents including polyethyleneglycol and ethanol, or detergents.

In another embodiment, the liposomes are composed of distearoylphosphatidylcholine (DSPC): cholesterol (52:45 molar ratio), and contain additionally 3 mol % PEG(2000)-DSPE compared to total lipid. The liposomes are prepared by freeze-thaw cycles and extrusion as described (Huwyler, et al. (1996) Proc Natl Acad Sci 93: 14164-14169). Essentially, lipids are first dissolved in chloroform or chloroform/methanol 2:1 vol/vol. A lipid film is prepared by vacuum evaporation using a Rotavapor (Bi chi, Switzerland). Dried lipid films are hydrated at 40° C. in 0.01 M PBS or 65o in 0.3 M citrate (pH4.0), such that a final lipid concentration of 10 mM is achieved. Lipids are subjected to five freeze-thaw cycles, followed by extrusion (5 times) at 20° C. through a 100 nm pore-size polycarbonate membrane employing an extruder (Avanti Polar Lipids, Alabaster, Ala.). Extrusion is repeated 9 times using a 50 nm polycarbonate membrane. This procedure produces PEG-derived liposomes with mean vesicle diameters of 150 nm. As has been previously demonstrated (Schnyder, et al. (2004) Biochem J. 377:61-67), biotinylated loaded liposomes may be prepared by substituting a portion of the PEG-DSPE with linker lipid (biotin-PEG-DSPE) and adding carboxy-fluoroscein at the hydration step.

For the purposes of treating subjects having neoplastic disorders, the entrapped therapeutic agent is, in one embodiment, a cytotoxic drug. Cytotoxic agents are particularly useful as the entrapped agent in liposomes targeted for neoplastic disease indications. The drug may be an anthracycline antibiotic selected from but not limited to doxorubicin, daunorubicin, epirubicin and idarubicin and analogs thereof. The cytotoxic drug can be a nucleotide analog selected from but not limited to gemcitabine, capecitabine, and ribavirin. The cytotoxic agent may also be a platinum compound selected from but not limited to cisplatin, carboplatin, ormaplatin, and oxaliplatin. The cytotoxic agent may be a topoisomerase 1 inhibitor selected from but not limited to the group consisting of topotecan, irinotecan, SN-38, 9-aminocamptothecin and 9-nitrocamptothecin. The cytotoxic agent may be a vinca alkaloid selected from but not limited to the group consisting of vincristine, vinblastine, vinleurosine, vinrodisine, vinorelbine and vindesine. The cytotoxic agent may be a taxane derivative selected from but not limited to the group consisting of taxol (paclitaxel), and docetaxal, and taxotere.

In another embodiment, the entrapped agent is a nucleic acid. Some examples of nucleic acids which can be delivered using the EGFR-targeting peptides of the invention include but are not limited to an RNA interfering or RNA silencing oligonucleotide, an antisense oligonucleotide, ribozyme, or a plasmid containing a therapeutic gene which when internalized by the target cells achieves expression of the therapeutic gene to produce a therapeutic gene product.

Use of Targeting Ligand Compositions

The EGFR-targeting peptides of the invention may be administered in simple or complexed forms, formulations, or as components of other compositions as described herein to a subject in need thereof to prevent, treat, manage or ameliorate a cancer or one or more symptoms thereof. The EGFR-targeting peptides of the invention may also be administered in combination with one or more other therapies, preferably therapies useful for the prevention, management or treatment of cancer (including, but not limited to the prophylactic or therapeutic agents listed hereinbelow) to a subject in need thereof to prevent, treat, manage or ameliorate a cancer or one or more symptoms thereof. In a specific embodiment, the invention provides a method of preventing, treating, managing or ameliorating cancer or one or more symptoms thereof, said method comprising administering to a subject in need thereof a dose of a prophylactically or therapeutically effective amount of a formulation comprising the EGFR-targeting peptides of the invention. In another embodiment, the invention provides a method of preventing, treating or ameliorating cancer or one or more symptoms thereof, said method comprising administering to a subject in need thereof a dose of a prophylactically or therapeutically effective amount of EGFR-targeting peptides of the invention in conjunction with a prophylactically or therapeutically effective one or more therapies (e.g., surgery, radiation therapy, or administration of other therapeutic agents). The EGFR-targeting peptide of the invention may be used as a first, second, third or fourth line cancer treatment. The invention provides methods for treating or ameliorating one or more symptoms of a cancer in a subject. Further, the invention provides methods for preventing the recurrence of cancer in patients that have been treated and have no disease activity by administering an EGFR-targeting peptide of the invention.

Cancers that can be treated by the methods encompassed by the invention include, but are not limited to, neoplasms, tumors, metastases, or any disease or disorder characterized by uncontrolled cell growth. The cancer may be a primary or metastatic cancer. The cancerous cells may or may not express EGFR. In a preferred embodiment, the cancer that is being managed, treated or ameliorated in accordance with the methods of the invention is a cancer expressing EGFR and has metastasized to the another site or organ within the body of the patient or has the potential to metastasize. Specific examples of cancers that can be treated by the methods encompassed by the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's lymphoma; myelomas such as multiple myeloma, nonsecretory myeloma, osteosclerotic myeloma, plasma cell leukemia, solitary plasmacytoma and extramedullary plasmacytoma; Waldenstrom's macroglobulinemia; bone cancer and connective tissue sarcomas such as bone sarcoma, myeloma bone disease, osteosarcoma, chondrosarcoma, Ewing's sarcoma, Paget's disease of bone, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, nonglial tumor, acoustic neurinoma, craniopharyngioma, medulloblastoma, meningioma, pineocytoma, pineoblastoma, primary brain lymphoma; breast cancer including adenocarcinoma and intraductal carcinoma, and papillary breast cancer; adrenal cancer including pheochromocytoma and adrenocortical carcinoma; thyroid cancer; pancreatic cancer; pituitary cancers; eye cancers not limited to ocular melanoma, choroidal melanoma, cilliary body melanoma, and retinoblastoma; vaginal cancers; vulvar cancer; cervical cancers; uterine cancers not limited to endometrial carcinoma and uterine sarcoma; ovarian cancers; esophageal and other head and neck cancers such as but not limited to, squamous cancer, adenocarcinoma, mucoepidermoid carcinoma, adenosquamous carcinoma, sarcoma, melanoma, plasmacytoma, verrucous carcinoma, and oat cell (small cell) carcinoma; stomach cancers; colon cancers; rectal cancers; liver cancers such as hepatocellular carcinoma and hepatoblastoma, gallbladder cancers; cholangiocarcinomas; lung cancers such as non-small cell lung cancer, squamous cell carcinoma (epidermoid carcinoma), adenocarcinoma, large-cell carcinoma and small-cell lung cancer; testicular cancers, choriocarcinoma (yolk-sac tumor), prostate cancers; penal cancers; oral cancers not limited to squamous cell carcinoma; basal cancers; salivary gland cancers; renal cell cancer and other kidney cancers; and bladder cancers not limited to transitional cell carcinoma (for a review of such disorders, see DeVita, V. T., Hellman, S., & Rosenberg, S. A. Cancer: Principles and practice of oncology. Philadelphia: J. B. Lippincott Company; 6th Edition, 2001). Pre-malignant conditions may also be treated by the methods and compositions of the invention. Such cancers may include, but not be limited to, follicular lymphomas, carcinomas with p53 mutations, hormone dependent tumors of the breast, prostate and ovary, and pre-cancerous lesions such as familial adenomatous polyposis, and myelodysplastic syndromes.

In a preferred embodiment, the cancer that is being prevented, managed, treated or ameliorated in accordance with the method of the invention is selected from prostate cancer, breast cancer, bone cancer, melanoma, lung cancer and ovarian cancer. In another embodiment, the cancer that is being prevented, managed, treated or ameliorated in accordance with the methods of the invention is selected from metastatic tumors including, but not limited to, tumors that have or may metastasize to the bone (non-limiting examples are prostate, breast and lung cancers that have metastasized or have the potential to metastasize to the bone), tumors that have or may metastasize to the lung, tumors that have or may metastasize to the brain, and tumors that have or may metastasize to other organs or tissues of a subject.

Anti-Cancer Therapies

Any agent or therapy (e.g., chemotherapies, radiation therapies, hormonal therapies, and/or biological therapies or immunotherapies) which is known to be useful, or which has been used or is currently being used for the prevention, treatment, management or amelioration of cancer or one or more symptoms thereof can be used in combination with an EGFR-targeting peptide of the invention in accordance with the invention described herein. Therapeutic or prophylactic agents include, but are not limited to, peptides, polypeptides, proteins, fusion proteins, nucleic acid molecules, small molecules, mimetic agents, synthetic drugs, inorganic molecules, and organic molecules. Examples of the classes of such agents (i.e., anti-cancer agents) include, but are not limited to, cytotoxins, angiogenesis inhibitors, and immunomodulatory agents and agents used to provide relief from pain or to offset the deleterious effects of one or more therapeutic agents (e.g. bisphosphonate use to reduce the hypercalcemic effects of glucocorticoids). Bisphosphonates include, but are not limited to, alendronate, clodronate, etidronate, ibandronate, pamidronate, risedronate, tiludronate, and zoledronate.

Biologic immunomodulatory agents include: interleukin II (including recombinant interleukin II, or rIL2), interferon alpha-2a; interferon alpha-2b; interferon alpha-m; interferon alpha-n3; interferon beta-I a; interferon gamma-I b; anti-T cell receptor antibodies such as anti-CD3 antibodies (e.g. Nuvion (Protein Design Labs), OKT3 (Johnson & Johnson), or anti-CD20 antibodies (e.g. Rituxan (IDEC)), anti-CD52 antibodies (e.g. CAMPATH 1H (Ilex)), anti-CD11a antibodies (e.g. Xanelim (Genentech)); anti-cytokine or anti-cytokine receptor antibodies and antagonists such as anti-IL-2 receptor antibodies (Zenapax (Protein Design Labs)), anti-IL-6 receptor antibodies (e.g. MRA (Chugai)), and anti-IL-12 antibodies (CNTO1275 (Centocor)), anti-TNFalpha antibodies (REMICADE (Centocor)) or TNF receptor antagonist (ENBREL (Immunex)), anti-IL-6 antibodies (BE8 (Diaclone) and CNTO328 (Centocor)), and antibodies that immunospecifically bind to tumor-associated antigens (e.g., trastuzimab (Genentech).

Angiogenesis inhibitors (i.e., anti-angiogenic agents) may work by inhibiting endothelial cell proliferation or blocking activators of the angiogenic process. Agents considered to be anti-angiogenic include, but are not limited to angiostatin (plasminogen fragment); antiangiogenic antithrombin III; angiozyme, bevacizumab (Avastin™), genistein, and thalidomide.

Specific examples of anti-cancer agents which can be used in accordance with the methods of the invention include, but not limited to: 5-fluoruracil; acivicin; aldesleukin; altretamine; aminoglutethimide; amsacrine; anagrelide; anastrozole; anthramycin; arsenic trioxide; asparaginase; azacitidine; azetepa; azotomycin; batimastat; bicalutamide; bleomycin sulfate; bortezomib; brequinar sodium; bropirimine; busulfan; carboplatin; capecitabine; carmustine; carubicin hydrochloride; carzelesin; cedefingol; chlorambucil; chlormethine; cirolemycin; cisplatin; cladribine; clofarabine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; enloplatin; enpromate; epipropidine; epirubicin hydrochloride; erbulozole; erlotinib; esorubicin hydrochloride; estramustine; estramustine phosphate sodium; etanidazole; etoposide; etoposide phosphate; fazarabine; fenretinide; floxuridine; fludarabine phosphate; fluorouracil; fluorocitabine; fosquidone; fostriecin sodium; gefitinib; gemcitabine; hydroxyurea; idarubicin hydrochloride; ifosfamide; ilmofosine; imatinib; iproplatin; irinotecan hydrochloride; lanreotide acetate; letrozole; leuprolide acetate; liarozole hydrochloride; lometrexol sodium; lomustine; losoxantrone hydrochloride; masoprocol; mechlorethamine hydrochloride; megestrol acetate; melengestrol acetate; melphalan; menogaril; mercaptopurine; methotrexate; methotrexate sodium; metoprine; meturedepa; mitomycin; mitosper; mitotane; mitoxantrone hydrochloride; mycophenolic acid; nocodazole; ormaplatin; paclitaxel; pegaspargase; pemetrexed, pentostatin; porfromycin; prednimustine; procarbazine hydrochloride; puromycin; raltitrexed, rogletimide; safingol hydrochloride; semustine; simtrazene; sparfosate sodium; sparsomycin; spiromustine; spiroplatin; streptonigrin; streptozocin; sulofenur; talisomycin; taxol (paclitaxel), taxotere, tegafur; teloxantrone hydrochloride; temoporfin; temozolomide; teniposide; teroxirone; testolactone; thiamiprine; thioguanine; thiotepa; tiazofurin; tirapazamine; topotecan; tretinoin; trimetrexate; trimetrexate glucuronate; triptorelin; uracil mustard; uramustine, uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

The invention also encompasses administration of an EGFR-targeting peptide of the invention in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radiaoactive source is placed inside the body close to cancer cells or a tumor mass.

Uses of EGFR-Targeting Peptides in Non-Neoplastic Disease

With the threat of bioterrorism, smallpox has recently reemerged as a medical and public safety concern. Vaccinations against smallpox, which was eradicated in 1977, ceased in the 1980s and as a result, a large segment of the population is susceptible to this disease. Thus, additional methods to contain future outbreaks of smallpox are needed. EGFR inhibitors may prove useful in this regard. Poxviruses such as variola virus, the causative agent of smallpox, exploit the ErbB signaling network via virus-encoded, EGF-like growth factors. These growth factors, which are carried in the genomes of all orthopoxviruses (24, Kim et al., J Biol Chem 279: 25838-48, 2004), are essential for viral pathogenesis and host cell proliferation at the site of infection (25, McFadden et al., Transplant Proc 28: 2085-8, 1996). In vitro and in vivo studies of neutralizing anti-growth factor antibodies (24, Kim et al., J Biol Chem 279: 25838-48, 2004) and EGFR kinase inhibitors ((26, Yang et al., J Clin Invest 115: 379-87, 2005) have demonstrated the importance of both the interaction between viral growth factors and EGFR, and of subsequent EGFR signaling, for viral infection. These results point to the potential of EGFR inhibitors as antiviral agents.

Methods and Routes of Administration

The methods of formulating and delivering and dosing the EGFR-targeting peptides of the invention to treat subjects suffering from diseases in which EGFR-expressing cells are prominent and problematic will depend on the nature of the disease and the tissue(s) affected, and the nature of the EGFR-targeting peptide composition.

For example, it is anticipated that targeted liposomal structures will be used at doses which are comparable to untargeted liposomes such as the STEALTH liposome DOXIL. Recommended safe and effective dosages, routes of administration and recommended usage are known in the art and have been described in such literature as the Physician's Desk Reference (60th ed., 2006) now available through the internet by subscription from PDR® Electronic Library™ Online: © 2002-2006. Thomson MICROMEDEX. All rights reserved. The PDR® Electronic Library consists of: PDR®, PDR® for Nonprescription Drugs and Dietary Supplements®, PDR® for Ophthalmic Medicines™, PDR® Multi-Drug Interactions, PDR® Addenda and PDR® Herbals. Each of these databases is © 2002-2006. Thomson PDR.). The dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. The dosage can be a one-time or a periodic dosage given at a selected interval of hours, days, or weeks.

Any route of administration is suitable, with intravenous and other parenteral modes being preferred.

As indicated above, liposomal compositions include a therapeutic or diagnostic agent in entrapped form. Entrapped is intended to include encapsulation of an agent in the aqueous core and aqueous spaces of liposomes as well as entrapment of an agent in the lipid bilayer(s) of the liposomes. Agents contemplated for use in the composition of the invention are widely varied, and examples of agents suitable for therapeutic and diagnostic applications are given below. In one embodiment, a combined treatment regimen is contemplated, where the immunoliposome composition described above is administered in combination with a second agent. The second agent can be any therapeutic agent mentioned herein, including other drug compounds as well as biological agents, such as peptides, antibodies, and the like. The second agent can be administered simultaneously with or sequential to administration of the immunoliposomes, by the same or a different route of administration.

Articles of Manufacture

The invention includes an article of manufacture containing materials useful for the treatment of the disorders described above comprising an EGFR-targeting peptide, a container and a label or package insert on or associated with the container. The article of manufacture preferably contains at least one vial comprising a solution of at least one EGFR-targeting peptide with the prescribed buffers and/or preservatives, wherein said packaging material comprises a label that indicates that the material can be held over a period of time. The invention may comprise an article of manufacture, comprising packaging material, a first vial comprising a dry powder form, e.g. lyophilized form, of at least one EGFR-targeting peptide composition, and a second vial comprising an aqueous diluent of prescribed buffer or preservative, wherein said packaging material comprises a label that instructs a practitioner or patient how to reconstitute the at least one EGFR-targeting peptide composition in the aqueous diluent to form a solution.

Suitable containers include, for example, bottles, vials, or syringes. The containers may be formed from a variety of materials such as glass or plastic. The container may have a sterile access port (for example the container may be an intravenous solution bag or a vial having a stopper pierceable by a hypodermic injection needle).

At least one active agent in the composition is an EGFR-targeting peptide composition. The label or package insert indicates that the composition is used for treating the condition of choice, such as cancer. The package insert herein may indicate that the EGFR-targeting peptide composition is used to treat a subset of cancer patients, such as those diagnosed with colorectal cancer, breast cancer, prostate cancer, or a particular stage of a particular cancer as when the primary tumor has metastasized to other organs and tissues or patients with cancer that does not respond, or respond poorly, to treatment with the standard of care as outlined herein for specific diseases and diagnoses.

While having described the invention in general terms, the embodiments of the invention will be further disclosed in the following examples.

Example 1

Phage Peptide Libraries

Seventeen libraries were constructed (Table 1), carrying peptides of varying length and some including two fixed cysteines in order to promote the display of disulfide-constrained cyclic peptides. The pIII libraries were constructed in a phage vector and contained an ala-gly dipeptide at the amino terminus (to promote even processing by the signal peptidase) and a gly-gly spacer between the peptide and mature pIII. The pIX libraries were constructed in a phagemid vector, with the randomized peptide flanked by a gly-gly-gly tripeptide at the N-terminus and glycine-rich linker at the C-terminus. Library diversities ranged from $10^8$ to $10^9$ independent clones.

pIII Phage Peptide Libraries.

Phage peptide libraries were constructed in phage vectors derived from M13mp19 (New England Biolabs). These vectors contain a stuffer fragment carrying a suppressible amber nonsense codon between the gene III leader and mature gene III. Vector phage were cultured in XL-1 Blue host cells (Stratagene), which can suppress the amber codon, and single-stranded DNA was isolated from these phage and used as template for a mutagenesis reaction. Phosphorylated, mutagenic oligos containing a central degenerate region, flanked by constant regions designed to anneal to the vector at sites surrounding the amber codon, were synthesized, hybridized with the single-stranded template DNA, extended with T7 DNA polymerase, and the resulting nicked, heteroduplex DNA was sealed with T4 DNA ligase. The products of this ligation reaction were transformed into the non-suppressing host MC1061-F' (MC1061, available from the ATCC) carrying the F factor from XL-1 Blue by electroporation, and the recombinant library phage were cultured in 2xYT medium for 4.5 hr at 37° C. Library phage were harvested from the culture supernatant by precipitation with 6% polyethylene glycol-8000 in 0.5 M sodium chloride. The final phage pellet was resuspended in PBS and stored frozen at −80° C. DNA sequencing confirmed the degeneracy of the randomized positions and the structure of the library insert.

pIX Phagemid Peptide Libraries.

The phagemid libraries S15-S20 were constructed in pPEP9-Bbs1.1, a vector derived from pPEP9 (K. Janda, Scripps Research Institute) that contains a lac promoter and operator, the leader sequence from pectate lyase (pel) B, a stuffer fragment containing dual, outwardly-directed restriction sites for the type IIS restriction enzyme BbsI, and the coding sequence for pIX as previously described in U.S. Pat. No. 6,472,147. To generate the insert for the libraries, phosphorylated, degenerate synthetic oligonucleotides were annealed to short, constant oligos that provided the appropriate restriction overhangs as depicted. The inserts were ligated into BbsI-digested, gel-purified vector, and the ligations were electro-transformed into XL-1 Blue. The phagemids were rescued with VCS-M13 helper phage and phage isolated by precipitation with 6% polyethylene glycol-8000 in 0.5 M sodium chloride. The final phage pellet was resuspended in PBS and stored frozen at −80° C. DNA sequencing confirmed the degeneracy of the randomized positions and the structure of the library insert.

TABLE 1

| Library | Structure of Displayed Peptide | |
|---|---|---|
| CNL1 | [pIII LEADER . . . SHS] - AG -$X_2CX_6$ C-$X_2$- GG - [TVESC . . . mature pIII] | (SEQ ID NO: 62) |
| CNL2 | [pIII LEADER . . . SHS] - AG -$X_8$- GG - [TVESC . . . mature pIII] | (SEQ ID NO: 63) |
| CNL3 | [pIII LEADER . . . SHS] - AG -$X_{14}$- GG - [TVESC . . . mature pIII] | (SEQ ID NO: 64) |
| CNL4 | [pIII LEADER . . . SHS] - AG -$X_6$ (F/L/Y/C/W/*) $X_6$ - GG - [TVESC . . . mature pIII] | (SEQ ID NO: 65) |
| CNL5 | [pIII LEADER . . . SHS] - AG -$X_2$ C $X_7$ C $X_2$- GG - [TVESC . . . mature pIII] | (SEQ ID NO: 66) |
| CNL6a | [pIII LEADER . . . SHS] - AG -$X_2$ C $X_8$ C $X_2$- GG - [TVESC . . . mature pIII] | (SEQ ID NO: 67) |
| CNL7 | [pIII LEADER . . . SHS] - AG -$X_2$ C $X_9$ C $X_2$- GG - [TVESC . . . mature pIII] | (SEQ ID NO: 68) |
| CNL8a | [pIII LEADER . . . SHS] - AG -$X_2$ C $X_{10}$ C $X_2$- GG - [TVESC . . . mature pIII] | (SEQ ID NO: 69) |
| CNL9 | [pIII LEADER . . . SHS] - AG -$X_{10}$- GG - [TVESC . . . mature pIII] | (SEQ ID NO: 70) |
| CNL10 | [pIII LEADER . . . SHS] - AG -$X_{12}$- GG - [TVESC . . . mature pIII] | (SEQ ID NO: 71) |
| CNL11 | [pIII LEADER . . . SHS] - AG -$X_{14}$- GG - [TVESC . . . mature pIII] | (SEQ ID NO: 72) |
| S15 | [pel B signal . . . AMA] - GGG - $X_{15}$ - GGGSGGSGG - MSVL . . . pIX | (SEQ ID NO: 73) |
| S16 | [pel B signal . . . AMA] - GGG-$X_2$-C-$X_6$-C-$X_2$-GGGSGGSGG-MSVL . . . pIX | (SEQ ID NO: 74) |
| S17 | [pel B signal . . . AMA] - GGG-$X_2$-C-$X_7$-C-$X_2$-GGGSGGSGG-MSVL . . . pIX | (SEQ ID NO: 75) |
| S18 | [pel B signal . . . AMA] - GGG-$X_2$-C-$X_8$-C-$X_2$-GGGSGGSGG-MSVL . . . pIX | (SEQ ID NO: 76) |
| S19 | [pel B signal . . . AMA] - GGG-$X_2$-C-$X_9$-C-$X_2$-GGGSGGSGG-MSVL . . . pIX | (SEQ ID NO: 77) |
| S20 | [pel B signal . . . AMA] - GGG-$X_2$-C-$X_{10}$-C-$X_2$-GGGSGGSGG-MSVL . . . pIX | (SEQ ID NO: 78) |

Example 2

Phage Panning Reagents

In order to select phage capable of high affinity association with cell surface expressed EGFR of the form with a potential to internalize with bound ligand, specific reagents were constructed. A dimeric form of the soluble ectodomain of EGFR (sEGFR-MMB) was used as the panning target for affinity-based selection (FIG. 1, SEQ ID NO: 2).

The extracellular domain of EGFR (sEGFR) comprises four domains which are pairs of large (L) binding domains and CR (cysteine-rich) and in series (L1-CR1-L2-CR2). L1 is also domain I, CR1 domain II, L2 domain III, and CR2 domain IV (See Burgess, et al. 2003. Mol. Cell. 12:541-552 for a review). A conformation described as the "tethered" relates to the association of domain II and domain IV the CR (cysteine-rich) domains, thought to mask or otherwise block the ligand binding domain III. A small, estimated at 5%, fraction of the EGFR are in the untethered form on the cell surface at any one time. However, ligand binding also leads to distention of the extracellular portion to cause "untethering", that is, the unfolding of the protein such that domain IV no longer masks domain II, and promotes dimerization in which portions of domain II of two sEGFR associate, which further evokes signal transduction processes (Burgess, supra; Dawson, et al. 2005 Mol Cell Biol. 25:7734-7742).

Therefore, a bivalent sEGFR structure wherein the domain II regions are free to come into contact was reasoned to exemplify a possible configuration of the untethered, dimerized receptor (FIG. 1, lower panel). Further, because high-affinity ligand binding of native EGFR is linked to untethering and dimerization of the receptor, the construct designated sEGFR-MMB (SEQ ID NO: 2) was used to represent a stabilized, untethered, high-affinity binding state of the receptor. Presumably, this conformationally stable molecule is found more abundantly represented on the tumor cell surface and rarely found on normal cells not prone to EGFR upregulation or overexpression.

sEGFR-MMB Reagent Preparation.

The cDNA encoding the soluble EGFR ectodomain was cloned from a total RNA preparation of the mammalian tumor cell line MDA-MB 231 by reverse-transcriptase PCR using a Forward primer of SEQ ID NO: 4 and reverse primer of SEQ ID NO: 5 linked to restriction site sequences as noted below.

```
Forward primer-5' BstZ17I
                                          (SEQ ID NO: 4)
5'-aag tat aca ggc cca gat cca gct gga gga aaa
gaa agt ttg c-3'

Reverse primer-3' BglII
                                          (SEQ ID NO: 5)
5'-aaa gat ctg gac ggg atc tta ggc cca-3'
```

The cDNA was subcloned into an expression vector with a CMV promoter driving transcription of intron A from CMV and the coding region for the signal sequence and the mimetibody scaffold. The sEGFR-MMB expression vector was verified by sequencing and transfected into Human Embryonic Kidney cells (293E). The protein was isolated from the culture supernatant and purified by protein A affinity chromatography and size-exclusion chromatography. The final protein product was verified by SDS-PAGE. On a nonreducing gel, the protein appeared as a single band of approximately 200 kDa based on the molecular standards and a single band migrating at approximately 100 kDa under reducing conditions confirming that the product was a disulfide linked homodimer.

To verify the suitability of the sEGFR-MMB protein for phage panning, a mock selection experiment was performed. Phage displaying EGF was diluted into a $10^9$-fold excess of native phage that do not display any peptide, and this phage mixture was panned in three successive rounds of affinity selection and amplification. The yield of phage from the pool increased dramatically in the third round of selection (Table 2), indicating the enrichment of high affinity phage. PCR screening of the eluted phage confirmed that EGF phage was successfully enriched in this mock panning experiment (not shown).

TABLE 2

Yield of phage from three rounds of mock selection of EGF phage spiked into excess no peptide phage.

| Round | Yield = [eluted phage]/[input phage] |
|-------|--------------------------------------|
| 1     | $9.0 \times 10^{-7}$                 |
| 2     | $6.5 \times 10^{-7}$                 |
| 3     | $2.5 \times 10^{-3}$                 |

In addition, a monomeric form of sEGFR bearing a hexahistidynal tag at the C-terminus, sEGFRhis6 (SEQ ID NO: 1), was also constructed, and transiently expressed in HEK293E mammalian cells as a secreted protein. The sEGFR-His$_6$ protein was purified from the cell culture supernatant by immobilized metal affinity chromatography. The purified protein had an observed molecular weight of about 80-90 kD by SDS-PAGE and an expected molecular weight of 70 kD, suggesting the protein was extensively glycosylated. The mass was confirmed by the MALDI mass spectrometry study (data not shown) and is consistent with published reports of a similar protein construct (Domagala et al., Growth Factors 18: 11-29, 2000).

Characterization of Affinity.

Figure 3:
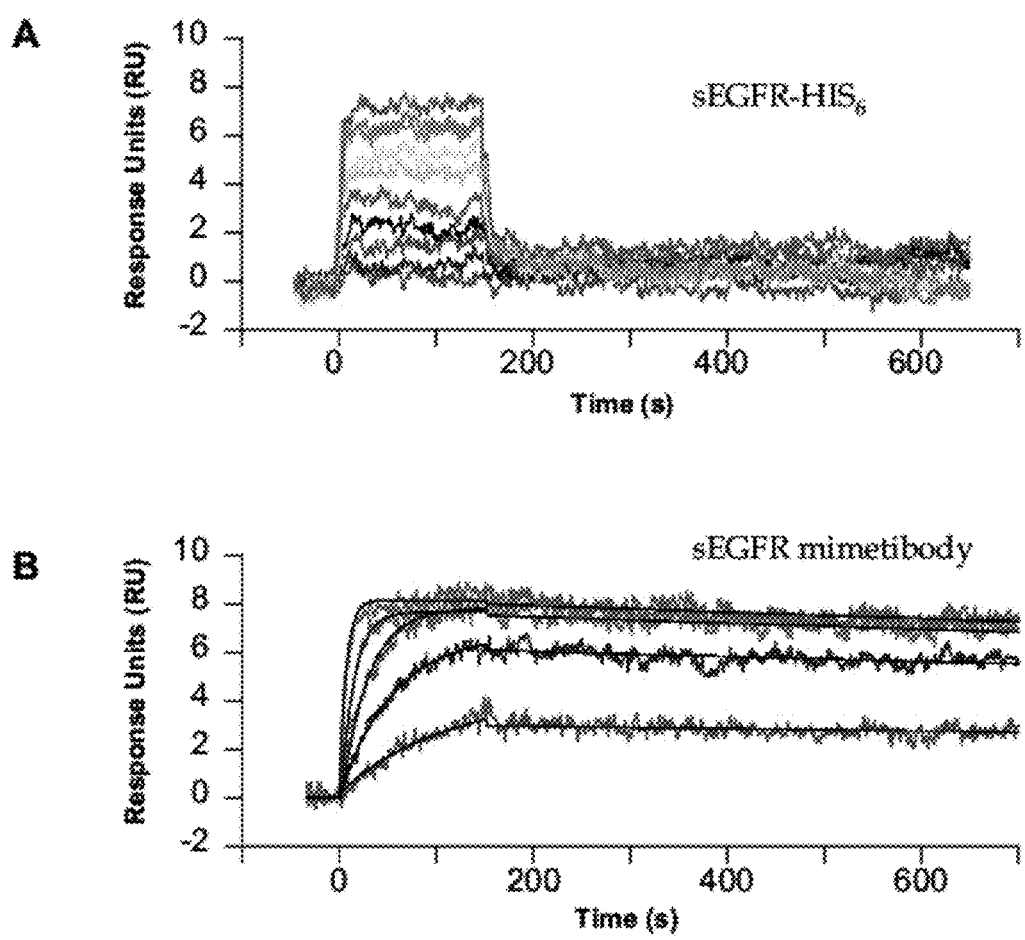
FIGS. 3A and B show representative BIAcore sensorgrams obtained for the interaction of EGF with sEGFR-His6 (A) and sEGFR-MMB (B) where the black lines correspond to the fit of the data.
Figure 4:
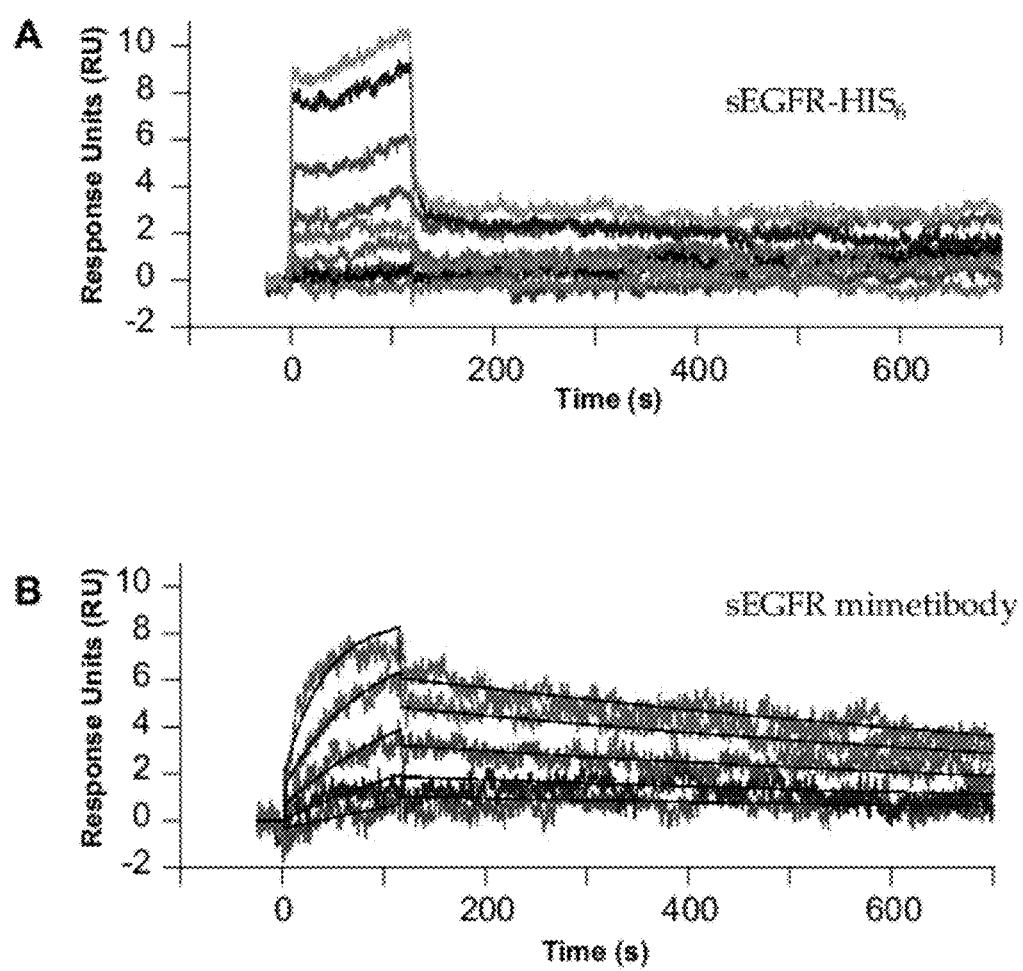
FIGS. 4A and B show representative BIAcore sensorgrams obtained for the interaction of TGF-a with sEGFR-His6 (A) and sEGFR mimetibody (B) where the black lines correspond to the fit of the data.

The interaction of recombinant human EGF (hEGF, NCBI Accession No. NP_001954) and TGF-α(NCBI Accession No. NP_003227) with the two forms of EGF receptor, sEGFR-His$_6$ and the sEGFR-MMB, were analyzed using BIAcore (Table 3). EGF or TGF-α ligand was passed over sEGFR-His$_6$ proteins that had been captured on the sensor chip with an anti-His$_6$ antibody. Analysis of equilibrium binding data demonstrated that the receptor was fully active for binding EGF or TGF-α in this format, with a equilibrium dissociation constant ($K_D$) for the interaction between EGF and sEGFR-His$_6$ of ~65 nM (FIG. 2A) and between TGF-α and sEGFR-His$_6$ of ~371 nM (FIG. 2B). These values are consistent with those reported in the literature (Dawson, et al. 2005 Mol Cell Biol. 25:7734-7742). BIAcore experiments also showed that when EGF or sEGFR-His$_6$ was covalently immobilized directly on the sensor chip, the apparent dissociation constants were approximately 25-fold and 7-fold higher, respectively, and only 30% of the immobilized molecule was active for binding (data not shown). BIAcore experiments with the sEGFR-MMB, captured with an anti-human Fc antibody, demonstrated that the interaction of both EGF (FIG. 3B) and TGF-α(FIG. 4B) with the dimeric form is significantly longer-lived than with the monomeric reagent, sEGFR-his6 (FIGS. 3A and 4A). The response units for EGF (FIG. 3B) and TGFa (FIG. 4B) were normalized to the amount of sEGFR mimetibody captured.

The equilibrium dissociation constant ($K_D$) for the interaction between sEGFR-MMB and EGF was calculated to be 0.177 nM, and between sEGFR-MMB and TGFa to be 3 nM, respectively, using a ratio of the rate constants ($K_D=k_d/k_a$). This analysis demonstrated that the sEGFR-MMB bound EGF with about 360-fold higher affinity than sEGFR-His$_6$ and sEGFR-MMB bound TGF-α with about 124-fold higher affinity than sEGFR-His$_6$ (Table 3).

TABLE 3

BIAcore data for the interaction of EGF and TGF-α
with EGFR in PBS, at 25° C.

| Analyte | Target | $k_a$ (M$^{-1}$ s$^{-1}$) | $k_d$ (s$^{-1}$) | $K_D$ (nM) |
|---|---|---|---|---|
| hEGF | sEGFR-His$_6$ | $>1 \times 10^7$ | >0.01 | 65 ± 21 |
| hEGF | EGFR-MMB | $2.02 \pm 0.01 \times 10^6$ | $3.89 \pm 0.40 \times 10^{-4}$ | 0.177 ± 0.02 |
| hTGFα | sEGFR-His$_6$ | $>1 \times 10^7$ | >0.01 | 371 ± 60 |
| hTGFα | EGFR-MMB | $3.56 \pm 0.02 \times 10^5$ | $1.08 \pm 0.01 \times 10^{-3}$ | 3 ± 0.1 |

Thus, while studies on monomeric EGFR extracellular domain and constructs mutated in domain IV to eliminate the potential for the molecule to assume the tethered configuration have demonstrated a increase in affinity from 175 nM for EGF binding to 50, 32, or even 7.8 nM (Dawson, supra), the sEGFR-MMB construct exceeded the magnitude shift in binding affinity by several fold and assumed an affinity close to what has been measured for a minor population, 2-5%, of EGFR receptors on the cell surface (approximately 0.1 nM).

Example 3

Phage Selections

The phage libraries (Table 1) were panned against the sEGFR-MMB target receptor reagent immobilized on magnetic beads (Dynal). In round 1, 2 µg of receptor was captured on 20 µl of protein G beads by incubation for 1 hr at room temperature, with constant gentle agitation. The beads were rinsed two times with PBS-T (phosphate-buffered saline containing 0.1% Tween-20) and blocked with Starting Block (Pierce) by incubation for 1 hr at room temperature, with constant gentle agitation. The beads were rinsed two times again with PBS-T. 50 µl (about $10^{12}$-$10^{13}$ pfu) of each phage library or of a mixture of EGF-phage, which comprise the extra-cellular domain of human EGF expressed as a pIII or pIX fusion, spiked into M13KE (New England Biolabs) at a 1:10$^9$ ratio was mixed with 50 µl starting block and incubated with the immobilized receptor-bead complexes. A 10-fold molar excess of blank mimetibody scaffold protein (Control-MMB, SEQ ID NO: 3) was added to disfavor the selection of phage binding to the mimetibody scaffold. The phage were allowed to bind to receptor for 1 hr at room temperature. The beads were then washed with PBS-T, the bound receptor-phage complexes were eluted with 0.2 M glycine pH 2.2, and the eluates were neutralized with one-half volume of 1 M Tris pH 8.0. The washing (4 washes of 1 minute each) and elution (10 minutes) procedures were performed under constant agitation in a Kingfisher 96 instrument (Thermo Electron). The eluted phage were amplified in XL-1 Blue host cells, and the phage-containing culture supernatant was used for the second round of selection. Rounds 2 and 3 were performed similarly to round 1, except that (i) the amount of receptor used was decreased to 0.5 µg and the amount of beads and Control-MMB was decreased accordingly; (ii) protein A beads were used for capturing the mimetibody in round 2, and protein G beads in round 3; and (iii) 4% milk in PBS for round 2 or 1% bovine serum albumin in PBS for round 3 was substituted for Starting Block. Phage titers were measured by spotting serial dilutions of phage on a lawn of XL-1 Blue host cells embedded in top agar. The yield of phage from each round was calculated as the ratio of phage titer in the eluate to phage titer in the input sample.

Phage Screening.

Individual phage clones from selections were amplified and screened for EGFR binding by phage ELISA. To amplify pIII phage for screening, phage eluates from round 3 were diluted appropriately and plated with a lawn of XL-1 Blue to yield isolated single plaques. 24 plaques from each pool were picked and inoculated into a culture of XL-1 Blue host cells. The cultures were shaken at 37° C. for 4.5 hr and the cells were removed by centrifugation. To amplify pIX-displaying phagemid clones, phage eluates were infected into XL-1 Blue and plated onto LB-ampicillin plates. Individual colonies were cultured in 1 ml volumes and rescued with VCS-M13 helper phage. Bacterial cells were removed from phage cultures by centrifugation at (2250×g, 7 min) and the phage-containing supernatant was saved.

The phage-containing culture supernatants were assayed for binding activity by phage ELISA. sEGFR-MMB or Control-MMB (MMB scaffold of formula I without a non-immunoglobulin peptide, SEQ ID NO: 3), at 5 µg/ml in PBS, was coated in the wells of a Maxisorp microtiter plate (NUNC) overnight at 4° C. The protein solution was removed and wells were rinsed twice with Tris-Buffered Saline containing 0.05% Tween-20 (TBS-T) using a plate washer (Embla). The wells were blocked with Starting Block in TBS for 1 hr at room temperature and rinsed twice with TBS-T. An equal volume of phage supernatant and Starting Block in TBS were incubated in the wells for 1 hr at room temperature, and the wells were rinsed five times with TBS-T. Anti-M13/horseradish peroxidase conjugate (Amersham), diluted 1:5000 in Starting Block in TBS, was added into the wells and incubated for 1 hour at room temperature, and then the wells were rinsed five times with TBS-T. Finally, chemiluminescent peroxidase substrate (Roche) was added to the wells, and chemiluminescence was measured on a Tecan plate reader.

Confirmatory Phage ELISA.

Phage were amplified in XL-1 Blue host cells and purified by precipitation with 6% polyethylene glycol-8000/0.5 M sodium chloride. The precipitated phage were resuspended in phosphate-buffered saline in a volume that was 1/100th the original culture volume. For competitive ELISA experiments, plates were prepared by coating wells with sEGFR-MMB or the Control-MMB followed by blocking as described above. The competitive agent (EGF or TGF-α, Research Diagnostics; IMC-c225, Imclone Systems) at 10 µg/ml in starting block) was added to the wells and incubated for approximately 5 min before phage (typically 1 µl of the concentrated stock, or ~10$^{10}$ pfu) were added to the wells. The binding reaction was incubated for 1 hr at room temperature, and then bound phage were detected with anti-M13/HRP as above. For ELISAs with biotinylated receptors, streptavidin at 5 µg/ml was coated in the wells overnight at 4° C. The wells were rinsed with TBS-T, and biotinylated receptor (sEGFR-MMB, sEGFR—His6, or strep II-tagged sEGFR purchased from Research Diagnostics) at 5 µg/ml was incubated in the wells for 1 hr at room temperature with shaking. The wells were rinsed with TBS-T and then blocked with Starting Block. Bound phage were washed and detected with anti-M13/HRP as described above.

Results

Figure 5:
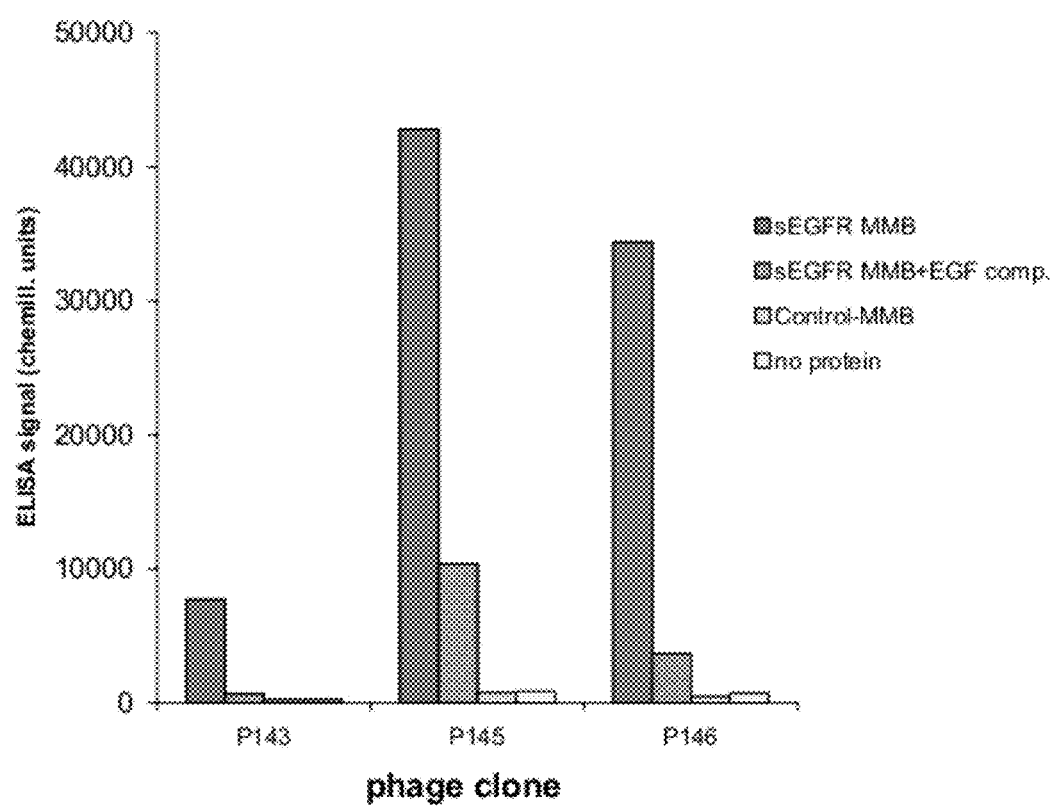
FIG. 5 shows data expressed as column graphs demonstrating that the binding of selected phage clones to sEGFR mimetibody (sEGFR-MMB) is competitive with EGF: a phage ELISA was used to measure binding of individual phage clones to the sEGFR-MMB, in the presence or absence of EGF (10 μg/ml), or Control-MMB alone.

The naïve pIII peptide phage libraries were panned against the sEGFR-MMB and several of the pools showed enrichment as indicated by an increased yield of phage after three rounds of selection. 24 individual clones from each of these pools were analyzed by phage ELISA, and sEGFR-MMB-binding clones were found from the CNL 5 library. These clones bound to sEGFR-MMB in a manner that was competitive with EGF, and did not bind a control protein consisting essentially of human IgG1 heavy chain dimer absent the variable and most of the CH1 domains designated "Control-MMB" (SEQ ID NO: 3) (FIG. 5).

Figure 6:
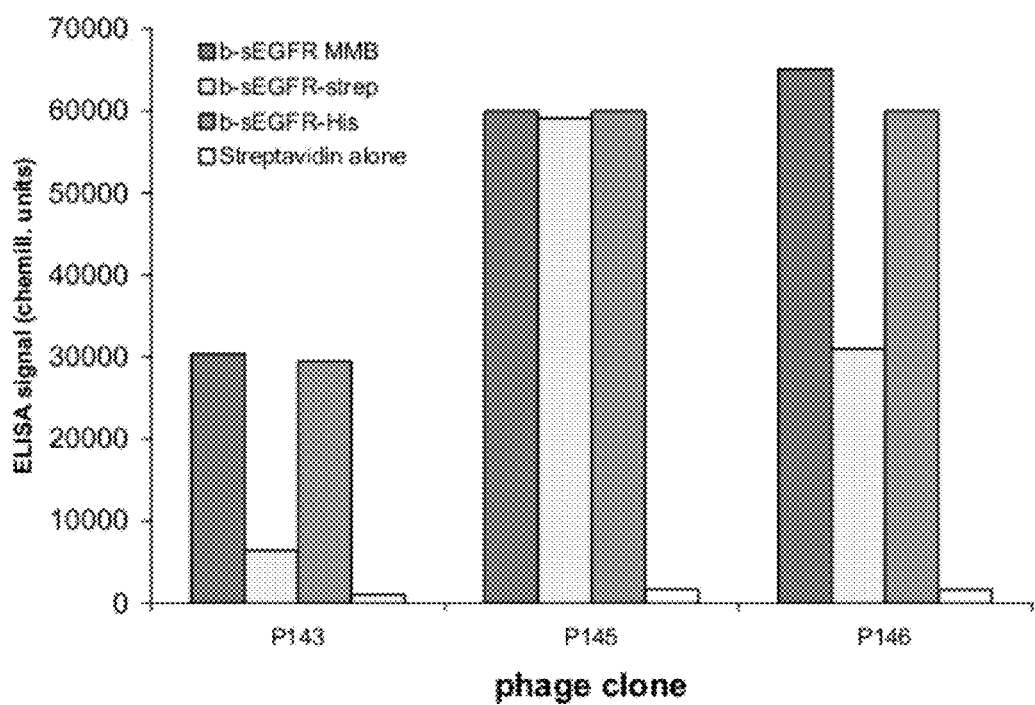
FIG. 6 shows data demonstrating that selected phage clones bind to sEGFR mimetibody and monomeric forms of sEGFR: biotinylated-sEGFR-MMB (b-sEGFR MMB), biotinylated sEGFR-His$_6$ (b-sEGFR-His), or strepII-tagged sEGFR (b-sEGFR-strep) was immobilized by capture on streptavidin-coated wells of a microtiter plate, and phage binding was measured by ELISA.

Sequencing revealed that three unique, but related peptides had been isolated (SEQ ID NO: 6-8). These peptides share a core motif of LCXXΦΦHPLC, where Φ is phenylalanine or tyrosine (SEQ ID NO: 9). Additional phage ELISA analysis demonstrated that these clones can bind to sEGFR-His$_6$, a His$_6$-tagged, monomeric form of sEGFR that had been biotinylated and immobilized on streptavidin (FIG. 6). In addition, the binding of the phage was inhibited by TGFα and by IMC-225, a neutralizing anti-EGFR monoclonal antibody (not shown).

TABLE 4

Sequences of EGFR-Binding Peptides from pIII phage library CNL5.

| Phage | Sequence (including inserts) | SEQ ID NO: |
|---|---|---|
| P143 | VLCSNFYHPLCHS | 6 |
| P145 | VLCHRYYHPICYT | 7 |
| P146 | TLCRSFFHPLCYA | 8 |
| Consensus | LCXXΦΦHPLC | 9 |

To isolate additional EGFR-binding peptides, the pIX phagemid libraries were also panned against sEGFR-MMB. After two or three rounds of panning, individual clones from each pool were screened by phage ELISA as above. Unique sets of hits were isolated from each library. A family of peptides were discovered (Table 5, SEQ ID Nos. 10 to 21) from the S15 library, which displays a random linear 15-mer. All of the selected peptides from this library contain a single cysteine that was not built into the naïve library structure and can be represented by the consensus sequence SLPXLLC (SEQ ID NO: 22). Additional families were identified from the S18 library (Table 6, SEQ ID Nos. 23 to 35) representing consensus sequence DCVXFGXXVYC (SEQ ID NO: 36), the S19 library (Table 7, SEQ ID Nos. 37 to 41) representing consensus sequence CXLXXDXXLIC (SEQ ID NO: 42), and from S20 (Table 8, SEQ ID Nos. 43 to 49) representing consensus sequence CXXTXFDXWXVC (SEQ ID NO: 50). From S16 and S17, two and one unrelated phage clones, respectively, were isolated (Table 9, SEQ ID Nos. 51 to 53).

Tables 5-9 gives phage isolated from S15-S20 by panning Sequences and ELISA signal (background typically <200 units) are given, along with a consensus sequence, if any. Cysteines that are fixed in the library design are underlined.

TABLE 5

S15 Hits

| Phage | SEQUENCE | ELISA | SEQ ID NO: |
|---|---|---|---|
|  | Y R L F V D E S I F F C T R L | 3078 | 10 |
|  | E L G L P T L L C W P T D T L | 9380 | 11 |
|  | V S G I L P I L V C H P A A T | 1107 | 12 |
| P175 | L P D D S L P E L I C K V R G | 6790 | 13 |
|  | H V S L Q S L P E L I C V V S | 1362 | 14 |
|  | N W F S L P T L L C F P L N P | 3669 | 15 |
|  | S T I T S L P T L Q C W P I L | 13332 | 16 |
|  | P I D D E S L P V L Y C V T S | 1785 | 17 |
|  | P I F S S L P V L Y C T S Q L | 1425 | 18 |
|  | G A D T L P D L L C W E S S L | 5722 | 19 |
|  | T V F T L P E L V C V V A G T | 1515 | 20 |
|  | L P D L I C A V D S G T S G A | 1161 | 21 |
| Consensus | S L P X L L C |  | 22 |

TABLE 6

S18 Hits

| Phage | SEQUENCE | ELISA | SEQ ID NO: |
|---|---|---|---|
| | A G C I A F V D V V Y C A R | 6377 | 23 |
| | A K C I A F G N S V Y C L N | 31524 | 24 |
| | R D C I I F D K T V Y C V I | 17060 | 25 |
| | K H C I L F E K T V Y C A K | 9111 | 26 |
| | D S C I Q F A N L L Y C A I | 53162 | 27 |
| | T D C I R F G V L W Y C L V | 4746 | 28 |
| | R A C I T F G K V V Y C E V | 30741 | 29 |
| | A Y C S F V A G D L V C Q V | 19792 | 30 |
| | T D C V I F G L E T Y C L R | 37925 | 31 |
| | S D C V L F G S K L F C S A | 35327 | 32 |
| | T D C V R F G E T I Y C I V | 13291 | 33 |
| | Y D C V S F G A V A Y C P Q | 3205 | 34 |
| | R G C V V F G D N I Y C I V | 21963 | 35 |
| | D C I/V X F G X X L/V Y C | | 36 |

TABLE 7

S19 Hits

| Phage | SEQUENCE | ELISA | SEQ ID NO: |
|---|---|---|---|
| | M I C Y L V D S G N I I C Y K | 8806 | 37 |
| | Y D C M I R A D G S L I C W C | 1286 | 38 |
| | G P C V L I R D Y Y L L C L E | 13951 | 39 |
| | A F C R L D F N Q W L T C L V | 2581 | 40 |
| | C D C R E A V S A S L V C R Y | 3347 | 41 |
| Consensus | C X L X X D X X L/IL/IC | | 42 |

TABLE 8

S20 Hits

| Phage | SEQUENCE | ELISA | SEQ ID NO: |
|---|---|---|---|
| | P T C D S A T R R V L T I C A D | 5420 | 43 |
| | W M C F L E G Y G A S L M C Q C | 4795 | 44 |
| | D S C C S F L T D G T V V C S L | 9544 | 45 |
| | Y I C T P S D I D S W Y I C Y L | 6615 | 46 |
| | S V C V G T A F P G W M V C G P | 4771 | 47 |
| P176 | K T C V S T T F D L W F V C F A | 37440 | 48 |
| | L L C A T T S F R D W F V C F T | 4512 | 49 |
| Consensus | X X C X X X T X F D X W X V C X X | | 50 |

TABLE 9

S16 and S17 hits

| Phage | SEQUENCE | ELISA | SEQ ID NO: |
|---|---|---|---|
| P174 | S G C L D A L W Q C V Y | 34641 | 51 |
| P177 | D A C T M V F L W C S L | 8655 | 52 |
| P178 | R W C Y F W W I T I C E L | 7913 | 53 |

Binding assay results suggest that the various peptides isolated from the pIX libraries have binding profiles distinct from each other (FIGS. 7A-E). Like the CNL5 hits isolated from pIII libraries, the S20 sequence family members such as P176 bound both sEGFR-MMB and sEGFR-His$_6$ in a manner that is competitive with IMC-c225 (cetuximab), EGF, and TGF-α. On the other hand, the cyclic 6-mer peptide SGCLDALWQCVY (P174) (SEQ ID NO:51) bound both sEGFR-MMB and sEGFR-His$_6$, but this binding was not inhibited by the EGFR ligands tested. A third profile was exhibited by the peptides derived from the linear 15-mer family (e.g., P 175), which bound sEGFR-MMB but not sEGFR-His$_6$ and did not compete with EGFR ligands. Finally, the hits isolated from the cyclic 9-mer family (e.g., P179) bound sEGFR-MMB when it was passively immobilized in ELISA wells, but not biotinylated sEGFR-MMB that had been captured on streptavidin, suggesting that these peptides recognize yet another site on the receptor. These results for representative peptides are summarized in Table 8 (at the end of the specification).

Example 4

EGFR-Binding Peptide Characterization

As a first measure of whether the selected peptides may be useful as EGFR overexpressing cell targeting agents, phage binding to cell surface EGFR was measured. In these experiments, the selected phage clones P143 (SEQ ID NO. 6), PHPEP145 (SEQ ID No. 7), P146 (SEQ ID No. 8), P173 (SEQ ID No. 31), P174 (SEQ ID No. 51), P175 (SEQ ID No. 13), PP176 (SEQ ID No. 48), P177 (SEQ ID No. 52), P178 (SEQ ID No. 53), P179 (SEQ ID No. 39) and P180 (SEQ ID No. 37) were tested for their ability to bind to tumor cells.

Flow Cytometry.

To evaluate whether the selected peptides from phage display can bind to tumor cells that overexpress EGFR, A431 cells (epidermoid cancer) or an EGFR negative tumor cells, MCF-7 (breast carcinoma) were tested in a flow cytometry assay using fluorescence detection (FACS). For P145, PP146 and their control phage, 2.5×10$^5$ A431 cells were resuspended in 25 μl of flow staining buffer (dPBS with 1% BSA, 0.09% sodium azide) and incubated with 25 μl of phage clones for 1 hour at 4° C. M13KE (25 μl) and pIII EGF-phage (2 μl) were used as negative and positive controls, respectively. For P174 through 180 and their control phage, 2.5×10$^5$ A431 cells were resuspended in 10 μl of flow staining buffer (dPBS with 1% BSA, 0.09% sodium azide) that contained 10 μl of phage clones for 1.5-2 hours at 4° C. Bbs1.1 (10 μl) and pIX EGF-phage (10 μl) were used as negative and positive controls, respectively. Cells were washed two times with flow staining buffer and then incubated with 0.5 μg of mouse anti M13/fd/Fl filamentous phages monoclonal antibody conjugated to FITC (Fitzgerald Industries International, Inc. Concord, Mass.) for 45 minutes at 4° C. Cells were washed two times with flow staining buffer and acquired by FACSCalibur (BD, Franklin Lakes, N.J.) to detect bound phages on tumor cell surface.

Results.

Among all phage peptide clones, only PHPEP145, P146, P174 and P176 displayed binding to A431 tumor cells, an epidermoid carcinoma line that overexpresses EGFR, when detected by flow cytometry using anti-phage-FITC antibody (FIGS. 8A and 8B). Both PHPEP145 and PHPEP146 bound A431, although the binding was weaker than that exhibited by a positive control phage that displayed EGF on pIII. Binding to A431 by P174 and P176 was comparable to that by a positive control phage that displayed EGF on pIX. The respective negative control phages, M13KE-phage and Bbs1.1-phage, did not bind to A431 cells.

When binding to MCF-7, an EGFR negative tumor cell line, was measured the results showed that P174 binding was greater to A431 than to MCF-7 suggesting specificity to EGFR. P176 bound to a similar extent to both A431 and MCF-7 cells (FIG. 8C). P145, like P174 displayed greater binding to A431 than MCF-7 cells (data not shown).

Example 5

Alternate Method of Selection EGFR Binding Peptide

As the goal of the selection process is to provide a peptide which selectively binds a configuration of EGFR present on actively proliferating tumor cells and primed for internalization, a panning process was devised to promote the dimerization of the binding domains within the sEGFR-MMB reagent. This was achieved by addition of EGF to the reagent prior to contact with the phage library.

Evidence in the literature (Ferguson and others) proposes that the ligand binding domain on EGFR is distinct from the dimerization domain (See FIG. 1A). On the other hand, ligand binding confers and promotes the ability of EGFR to dimerize. Panning and characterization conditions were developed which enabled selection of a peptide with the following properties:
a) binds to dimeric configurations of the extracellular region of EGFR with higher affinity than to monomeric forms,
b) does not compete with natural ligands, EGF or TGFalpha, for binding to EGFR,
c) natural ligands, EGF or TGFalpha, enhance binding to dimeric froms of the extracellular regions of EGFR,
d) binds to human EGFR positive tumor cells in culture and does not bind human tumor derived cells (MCF-7) not expressing EGFR, and
e) internalizes in EGFR positive tumor cells in culture in the presence or absence of EGF.

First to be investigated, was whether the sEGFR-MMB fusion existed as a mixture of conformations, or if it adopted a single conformation that was not biologically relevant. Size-exclusion chromatography of the sEGFR-MMB in the presence and absence of EGF was compared. If the complex retained the same general shape as the sEGFR-MMB, 240 kDa, but simply became larger due to the contribution of an EGF protein (15 kDa), one would expect faster elution from the SEC column. Instead, elution of the complex was delayed from about 37.8 min to about 38.3 min, suggesting that the complex changes shape. The finding that the presence of EGF forced a measurable conformational change in the sEGFR-MMB reagent which is dimeric for the extracellular ligand binding domains of the receptor, became the basis for using the complex to select for binders having a specificity different than that of known antibodies, cetuximab and panatumumab, which bind and compete with natural ligands for EGFR.

The pIX phage library S18 was panned using various methods involving the sEGFR-MMB and solid phase capture for immobilizing the reagent, the sEGFR-MMB construct (SEQ ID NO: 2).

P189 (Table 10) was isolated from the cyclic 8-mer library S18 by first round panning against sEGFR-MMB, second round subtractive panning using MCF7 and selection for CHO EGFR⁻ cell binding, followed by a third round against sEGFR-MMB.

The sEGFR-MMB fusion protein was biotinylated with sulfo-NHS-LC-biotin (Pierce) according to the manufacturer's instructions. After biotinylation, 2 µg of sEGFR-MMB was captured on streptavidin-coated magnetic resin (Dynal) via a 30-minute incubation, and unbound protein was washed away with PBS. Prior to adding phage, the resin was incubated in Superblock (Pierce) for one hour to prevent non-specific binding of phage to the resin, and free binding sites on streptavidin were blocked with excess biotin to prevent the selection of HPQ-containing peptides. After blocking, 0.16 µg of EGF was added to the resin and was captured by the sEGFR-MMB during a 30-minute incubation. At this point the resin was washed twice with PBST, resuspended in Superblock (Pierce), and aliquots of EGF (0.16 µg) and phage library S18 were added. The mixture was allowed to tumble at room temperature for one hour and washed five times with PBST. The phage that remained bound to the resin were eluted with a 10-minute incubation in 0.2M glycine, pH 2.5, after which the solution was neutralized with 1M Tris, pH 8. Eluted phage were used to infect mid-log phase XL-1 Blue cells, and phage were grown for the next round of selection using common microbiological techniques. Three rounds of selections were carried out, and phage in the third round eluate were assayed for binding activity.

A non-cell based approach using either Ig-Fc binding protein A or G or biotin-avidin capture were used. Method A utilizes bacterial proteins A or G which are high affinity binders of the Fc portion of the fusion construct, or Method B using a biotinylated construct as described above bound to a high affinity biotin binding protein, streptavidin or avidin.

Method A: immobilized on Protein G beads in the presence of EGF, followed by sEGFR-MMB immobilized on Protein A beads in the presence of EGF, then again by sEGFR-MMB immobilized on Protein G beads in the presence of EGF. This method was compared to panning the same library successively by method B.

Method B: Strepavidin-captured biotinylated sEGFR-MMB in the presence of EGF, followed by avidin-captured biotinylated sEGFR-MMB in the presence of EGF, and then again strepavidin-captured biotinylated sEGFR-MMB in the presence of EGF.

Peptides selected by these two methods were examined for unique sequences and P190 was shown to represent 2 of 48 peptides isolated by method A and 40 of 48 peptides isolated by method B.

Additional peptides were isolated by panning from the pIII libraries CNL 1-11 (Table 1), using the following method sequence: first round against b-sEGFR-MMB, second and third round against b-sEGFR-MMB with Control-MMB as competitor. These peptides were designated P191-194. The unique sequences do not represent a consensus sequences nor do they show significant homology to P173 despite being isolated from the same pIII phage libraries.

P190 (GG-DPCTWEVWGRECLQ-GG) (SEQ ID NO:55) was discovered and identified by panning peptide libraries against sEGFR-MMB complex with EGF.

Binding Studies on P190

ELISA plates (96-well) were loaded with 100 μL per well of one of the following proteins at 5 μg per mL: sEGFR-His6, sEGFR-MMB or Control-MMB. The plates were held overnight at room temperature, washed twice with TBST (0.5M Tris Base, 9% NaCl, 0.05% tween, pH 7.6), and loaded with 200 μL per well of Starting Block (Pierce). If applicable, recombinant human EGF was added to the plates in greater than two-fold molar excess over sEGFR-MMB. The plates were held at room temperature for 1.5 hours for blocking Plates were then washed twice with TBST and phage were added. The phage solutions were crude phage supernatant from overnight cultures diluted four-fold with Starting Block. After a one-hour incubation, the plates were washed thrice with TBST and 100 μL of a 1:5000 dilution of phage binding antibody conjugate (α-M13-HRP) was added to the wells. EGF was added if applicable. After a one-hour incubation the plates were washed five times with TBST, 100 μL of POD (BM Chemiluminescence ELISA substrate; Roche Applied Science) was added, and chemiluminescene recorded.

Results

The phage displaying P190 exhibit virtually no binding to the sEGFR-His6 (monomerice sEGFR) while Phage displaying EGF did bind to sEGFR-6×His (Table 9). Phage displaying P190 fails to bind to the Control-MMB, binds weakly to the sEGFR-MMB, and binds well to the complex between EGF and sEGFR-MMB (Table 9).

TABLE 9

| Construct | Relative Signal |
|---|---|
| Control-MMB | 6 |
| sEGFR-His6 | 6 |
| Control-MMB | 260 ± 167 |
| SEGFR-MMB | 3937 ± 335 |
| SEGFR-MMB + EGF | 29408 ± 259 |

In addition, the pIX-displayed P190 did not compete with EGF or TGF-alpha for binding to EGFR but was inhibited by cetuximab; moreover, pIX-190 binding to dimeric EGFR was actually increased in the presence of EGF or TGF-a. As the binding of P190 is increased in the presence of the cognate ligands for EGFR, inhibition of binding of P190 by cetuximab, which itself competes with EGF for binding, can be interpreted to mean not that P190 and cetuximab bind the same site but rather that cetuximab prevents EGF from inducing the preferred conformation (dimerized form) of EGFR which promotes P190 binding. These results and the sequences of peptides isolated by the method of panning in the presence of EGF are given in Table 10 (at the end of the specification).

Example 6

Tumor Cell Specificity of Selected Peptide

In order to verify that the selected peptide was specific for EGFR as displayed on the surface of tumor cells, cell binding to EGFR positive (A431) and EGFR negative (MCF7) cells was examined.

A431 cells (epidermoid cancer) which overexpress EGFR and EGFR-negative tumor cells, MCF-7 (breast carcinoma) were tested in a flow cytometry assay. Tumor cells (A431 and MCF-7) were harvested with 0.25% tyrpsin-EDTA and washed twice with FACS staining buffer (dPBS with 1% BSA, 0.09% sodium azide). $2.5 \times 10^5$ cells were resuspended in 25 μL of flow staining buffer and incubated with 25 μL of 190-phage (pIII display) or 190-phagemid (pIX display) for 1 hour at 4° C. After binding at 4° C., cells were washed twice with FACS staining buffer to remove unbound phage and then incubated with 0.5 μg of mouse anti-M13 monoclonal antibody conjugated to FITC (Fitzgerald Industries International, Inc. Concord, Mass.) for 1 hour at 4° C. Mouse anti-M13-FITC incubated with cells without phage was used as background binding. Cells were washed twice with FACS staining buffer to remove unbound detection antibody. Finally cells were acquired by FACSCalibur (BD, Franklin Lakes, N.J.) and analyzed by Cell Quest software to detect bound phages on the cell surface.

Results

Figure 9:
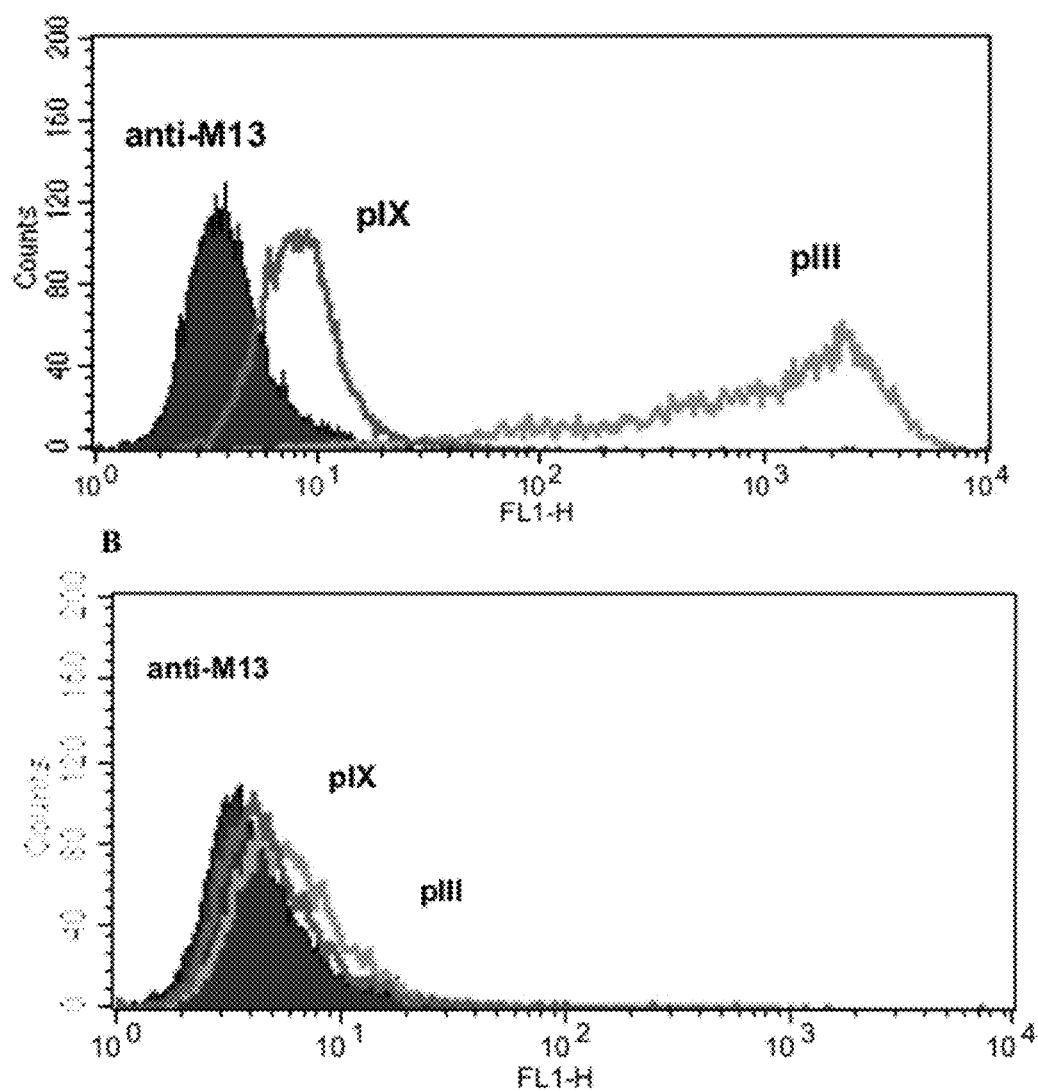
FIG. 9 shows the FACS results for binding of M13 phage displaying P190 as a fusion protein to either the pIII or pIX coat protein: EGFR+ A431 cells (A) and EGFR− MCF7 (B).

P190 bound more effectively to A431 cells (FIG. 9A) which express 1 to 2 million EGFR per cell (Yang, X D et al. 2001 Apr. Crit. Rev Oncol-Hematol. 38(1):17-23) compared to MCF-7 cells. Although MCF-7 have been reported to express less than 70,000 EGFR (Davidson, et al. 1987 Mol Endocrinol 1: 216-223), in our hands the anti-EGFR antibody staining was undetectable by FACS (FIG. 9B) The difference in apparent binding between pIX display and pIII results from the fact that pIX displays an average of one peptide per phage particle, while pIII display an average of five peptides per phage particle. Thus, the off-rate for the multi-displayed peptide phage will be effectively slowed.

Cell-based studies showed that pIX-190 and pIII-190 bind to A431 but not to MCF-7, suggesting the peptide binds specifically to EGFR+ tumor cells. In the presence of EGF, 190 phage peptide binding to A431 cells increased suggesting preferential binding to a dimeric (high-affinity) EGFR. In the presence of EGF and cetuximab, 190 phage binding to A431 cells decreases which may be explained by the fact that cetuximab in known to force EGFR into the low-affinity conformation and competes with EGF for binding.

Example 7

Tumor Cell Internalization of Peptide 190

P190 was labeled with a single biotin at the C-terminus to enable detection with a biotin-specific fluorescently labeled antibody on the surface and internal to tumor cells.

Synthesis of Biotinylated P190

Biotinylated-PEGylated P190 (bP190) was prepared on an ABI 431 Peptide synthesizer using 0.1 mM scale Fmoc chemistry. Synthesis was performed on Biotin-PEG NovaTag resin from Nova Biochem which allows addition of the PEG-linked biotin at the C-terminus of the peptide. The peptide was cleaved from the resin with stirring in a scintillation vial using a mixture of 10 mL TFA, 0.75 g Phenol, 0.5 mL water, 0.5 mL thioanisole, 0.5 mL TIS over 2 hours at ambient temperature. The resin was filtered off, the peptide precipitated with 400 mL ethyl ether, filtered, washed with ethyl ether, and dried. The peptide was redissolved in water and oxidized with stirring in 10% DMSO overnight. The peptide solution was acidified with TFA to 0.1% and loaded onto two Vydac C-18 columns (10 um, 2.5×25 cm) for purification in 0.1% TFA solutions using a gradient of acetonitrile. Fractions were collected and analyzed by HPLC. Pure fractions were pooled and lyophilized. Final product was characterized by HPLC and MALDI.

FACS Analysis of Biotinlyated 190 Peptide

A431 and MCF-7 were prepared as previously described. $2.5 \times 10^5$ cells were resuspended in 25 µL of FACS staining buffer with or without 2 µg human recombinant EGF (hrEGF). After 15 minutes, biotinylated P190bio-P190)) was added at 200, 400, and 800 nM) and the cells were incubated for an additional hour at 4° C. in FACS staining buffer containing sodium azide. Cells were then washed twice with FACS staining buffer, followed by incubation with mouse anti-biotin-Cy5 at 1:200 dilution (Jackson ImmunoResearch, Willow Grove, Pa.). Mouse anti-biotin-Cy5 incubated with cells without biotinylated P190 was used as a control. Cells were washed twice with flow staining buffer to remove unbound detection antibody. Finally, cells were acquired by FACSCalibur (BD, Franklin Lakes, N.J.) and analyzed by Cell Quest software.

Internalization Analysis of 190-Biotin by FACS and Confocal Microscopy

Biotinylated P190 or biotinylated EGF was pre-mixed with mouse anti-biotin-cy5 mAb for 1 hr at room temperature. The complexes were added to A431 cells that had been pre-incubated in PBS with or without EGF for 15 minutes and then incubated for an additional hour. Cells were washed to remove unbound complexes and split into two separate tubes, one of which stayed at 4° C. and one of which was incubated for 2 hours at 37° C. to promote internalization. Again, cells were washed and further split into 2 groups with one tube from each temperature undergoing acid wash treatment to remove surface-bound biotinylated peptide. Cells were washed again in FACS staining buffer and peptide binding and internalization were acquired by FACSCalibur (BD, Franklin Lakes, N.J.) and analyzed by Cell Quest software. The remaining cells from both 4° C. and 37° C. without acid wash after FACS analysis were centrifuged and resuspended with 50 µL mounting medium containing DAPI (Vector Laboratory Inc. Burlingame, Calif.). Ten µL of cells in mounting medium were transferred to a glass slide, covered with thin glass slips and examined by confocal microscopy.

Results

The FACS analysis confirmed that acid washing removed most of the surface associated peptide as the median fluorescence intensity of the cells was altered only negligibly from untreated cells (not shown) The result off staining A431 with concentrations up to 800 nM of bio-P190 was that staining intensity continued to increase with concentration on cells preincubated with EGF (FIG. 10B) but not those stained in the absence of exogenous EGF (FIG. 10A). When A431 cells were preincubated with 2 ug EGF and then stained with 2 uM bio-P190: avidin complex and held at 4° C., maximum staining was achieved (approximately 20-fold over background) which was removed by acid washing. When the stained in the same manner but incubated at 37° C., cell staining appeared several fold weaker, and this staining was not removed by acid washing.

Confocal microscopy confirmed that biotinylated-P190 was internalized as staining in samples held at 4° C. labeling was clearly at the circumference of the cells, while samples incubated at 37° C. showed bright pockets which were inside the cell. These observations are consistent with the reported internalization mechanism for EGFR that involves invagination of membrane pockets. EGFR⁻ cells demonstrated no internalization by FACS or microscopy. Therefore, P190 is internalized into EGFR⁺ cells.

Example 8

Structural and Conformation Studies of Peptide 190

Alanine Scan of 190

The vector (pPEP9-Bbs1.1) was engineered to insert fusions into the N-terminus of M13 phage coat protein pIX. The vector was digested with BbsI and gel purified. Cassettes were designed for P190 with the necessary changes and overhanging ends compatible with the vector and synthesized at Integrated DNA Technologies, Inc. Cassette oligos were annealed with cooling from 95° C. to 4° C. over 15 minutes in a PCR machine and subsequently ligated into the vector using a rapid DNA ligation kit (Roche). The ligation reaction was transformed into XL-10 Gold Ultracompetent cells (Stratagene) and selected on 2xYT plates with 100 µg/mL ampicillin. Colonies with inserts were identified by PCR and subsequently confirmed with sequencing at Genewiz, Inc. Phage displaying P190 or variants were added to mid-log *E. coli*, amplified for 4 hours, and precipitated using PEG/NaCl.

Solution Molecular Weight Determinations

The solution molecular weights of sEGFR-6×His and EGF (PeproTech, *E. coli*-derived) were determined by static light scattering as follows: A 50 µL aliquot of 0.32 mg/mL (5.3 µM) sEGFR-6×His sample was injected onto a Superose-6 column pre-equilibrated with DPBS (Invitrogen Corporation). The protein was eluted with DPBS at a flow rate of 0.35 mL/min. The eluting peaks were monitored using a Dawn-EOS Static Light Scattering detector (Wyatt Technology Corporation) that was pre-calibrated with toluene; a UV detector at 280 nm (Agilent Corporation); and an Optilab rEX Differential Refractometer (Wyatt Technology Corporation) pre-calibrated by the manufacturers.

Similar to the above-described method, 40 µL of 1.0 mg/mL (5.3 µM) EGFR-MMB was injected onto Superose-6 in DPBS with UV, RI and SLS monitoring for light scattering analysis as described previously.

Molecular Weight of the EGF-sEGFR-MMB Complex

The molecular weight of a mixture containing 5.3 µM (1 mg/mL) sEGFR-MMB and 53 µM (0.31 mg/mL) EGF was determined by static light scattering by injecting 40 µL of the mixture unto Superose-6 in DPBS then monitoring UV, RI and SLS signals as described above.

Solution MW analysis of P190 and P190-PEG-Biotin

The solution molecular weights of P190 and 190-PEG-Biotin were determined by static light scattering as follows: Ten and 40 µL injections of a 5.0 mg/mL (2 mM) solution of 190-PEG-Biotin in PBS was injected onto a Superdex Peptide column (GE Healthcare) pre-equilibrated with DPBS (Invitrogen Corporation). The peptide peaks were eluted with DPBS at a flow rate of 0.35 mL/min. The eluting peaks were monitored using a Dawn-EOS Static Light Scattering detector (Wyatt Technology Corporation) that was pre-calibrated with toluene; a UV detector at 280 nm (Agilent Corporation); and an Optilab rEX Differential Refractometer (Wyatt Technology Corporation) pre-calibrated by the manufacturers.

Similarly, P190 was assessed by injecting 31 µL of a 6.5 mg/mL solution in DPBS onto a Superdex Peptide column in DPBS while UV, RI and SLS signals were monitored.

Results

Figure 11:
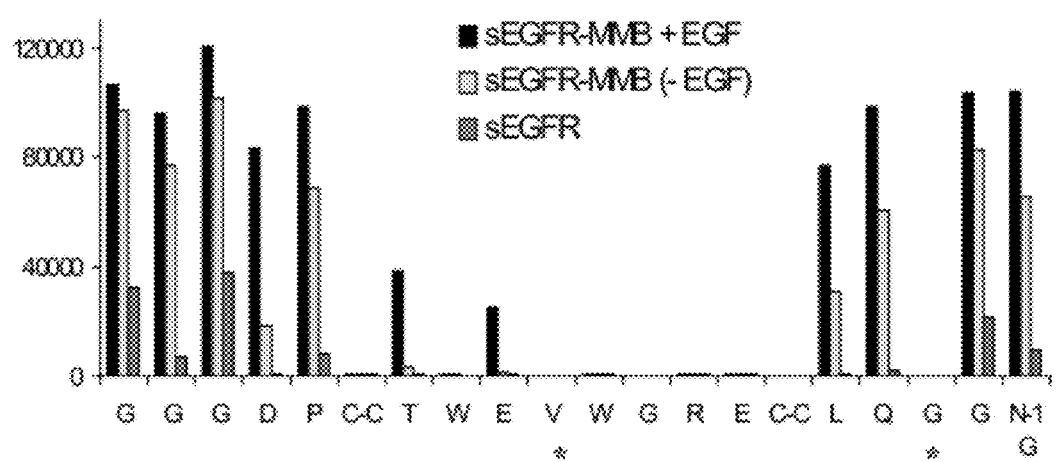
FIG. 11 is a column chart displaying the binding affinity of various P190 alanine-substituted mutations for different forms of sEGFR as a monomer and as the dimeric construct (sEGFR-MMB) with and without added EGF.

The alanine scanning of P190 whereby the indicated positions were mutated to alanine and the resulting binding activity measured by ELISA assay (as described in Example 2) for the peptides displayed from the phage coat protein pIX are shown in FIG. 11 where the asterisks indicated positions not tested. Each mutated peptide was assayed for binding to sEGFR, sEGFR-Fc, and sEGFR-Fc in a complex with EGF. The data indicates that the disulfide bond and each of the amino acids between the cysteines are essential for binding to the dimeric EGFR reagent (sEGFR-MMB).

Size exclusion chromatography and dynamic light scattering analysis of P190 showed that both the peptide itself and the biotinylated, PEGylated variant exist in solution as monomers.

Example 9

Preparation of P190-Conjugates and Conjugated STEALTH® Liposomes

Preparation of the EGFR-Binding Peptide-Lipid Conjugates

The P190 peptide contains no internal lysines so coupling through amines results in specific modification of the N-terminus. Targeted liposomes were prepared in a two-step process: the peptide was first conjugated to an activated PEGylated-diglyceride which will preferentially attack the N-terminal free alpha amine. Subsequently, the PEGylated-lipidated peptide was inserted into preformed STEALTH™ liposomes carrying a fluorescent dye (Alexa) or doxorubicin (DOXIL®).

The amine reactive reagent succinimidyl propionate polyethylene glycol (3400)-distearoylphosphatidylethanolamine (SPA-PEG3400-DSPE, Nektar (Shearwater)) was used to conjugate the peptide. Conjugation of P190 peptide to NHS-PEG-DSPE was performed using SPA-PEG3400-DSPE to P190 concentrations of 5.29 mg/ml and 0.88 mg/ml, respectively giving a molar ratio of 3:1, pH 7 at 25° C. for 10 hours. By varying pH between 6.8 and 7.8 and the ratio of SPA reagent to peptide from 2:1 to 6:1 it was determined that the conjugation efficiency of both P190 and biotinylated-P190 was approximately 100% at neutral pH and a ratio of reagent to peptide of 3:1 or greater. The material was characterized using a Zorbax 300SB-C8 (Agilent Technologies) 5 μm, 2.1 mm×7.5 cm and mobile phase gradient over 16 min from 95% A/5% B to 10% A/90B: mobile phase A 0.1% TFA in H2O; B 0.1% TFA in MeOH at a flow rate of 1.0 mL/min with the column temp maintained at 35° C. The injection volume was 20 μL and monitoring was by fluorescence using EX 280/EM 340 nm.

Preparation of P190-Conjugated STEALTH® Liposomes

The Doxil® liposome formulation is composed of HSPC (fully hydrogenated soy phosphatidylcholine), cholesterol and mPEG-DSPE was used. Doxorubicin was encapsulated inside of liposomes by remote loading technology (U.S. Pat. Nos. 5,013,556; 5,316,771) and fluorescence marker (dextran, Alexa 488 MW 10,000) was encapsulated by passively loading method (U.S. Pat. No. 5,945,122).

Preparation of EGFR-targeted liposomes used the pre-loaded liposomal structures. P190-PEG-DSPE conjugates were incorporated to the surface of pre-formed liposomes by the insertion method previously described (Therapeutic Liposome Composition and Method of Preparation, U.S. Pat. No. 6,056,973). P190-lipid conjugates form micelles in aqueous solution at room temp. The insertion process was carried out by incubation at 60° C. for one hour of an amount of P190-PEG-DSPE conjugate representing a ratio of 40-240 peptide per liposome resulting in insertion of between 40 and 200 P190-conjugates per liposome (Alexa-encapsulated SL or DOXIL®). Unbound conjugate were removed by passing the mixture over a Sepharose 4B SEC column with 20 mM HEPES-0.9% sodium chloride as elution buffer. The peptide-containing liposome fractions were detected using O.D. at 280 nm, combined, and concentrated using a Vivaspin concentrator. The insertion efficiency was analyzed by analytical HPLC using a TSK-GEL G2500PW Size Exclusion Column of 7.8 mm (ID)×30 cm with a mobile phase: 0.1% SDS in 0.1M $NaH_2PO_4$ at a flow rate of 0.5 mL/min. The injection volume was 15 μL and fluorescence detection at EX 280 nm/EM 340 nm. The insertion efficiency varied with ratio of peptide conjugate per liposome, e.g. 40:1 v 80:1, but was generally 65-80%.

These data demonstrate the several advantages of using a EGFR-binding peptide as targeting moiety for liposome conjugation compared to using larger proteins such as the EGF protein itself or anti-EGFR antibody fragments. As P190 contains 14 amino acids it can be produced synthetically instead of recombinantly which can be a more economical process. Importantly, having demonstrated that the conjugation efficiency of P190 an amine reactive reagent, SPA-PEG-DSPE, is almost 100% indicates a huge advantage as compared to the conjugation efficiency for larger proteins. Further, since there is only one reactive free α-amino group in P190 peptide the product conjugate is a homogenous chemical structure. In contrast, the conjugation of larger proteins, such as EGF protein (MW 6000) or antibodies (MW 150K) or their fragments, such as, Fab' (MW 55K) cannot be controlled due to their multiple reaction sites producing multiply conjugated products which will have heterogeneous biophysical properties and make liposomal incorporation likewise unpredictable. Moreover, reaction of essential free amines or other side groups in the proteins or oxidation of disulfides can destabilize or destroy the secondary and tertiary protein structures and affect protein-protein interactions all of which can alter function or diminish binding.

Example 10

In Vitro Binding and Internalization by EGFR-Targeted Liposomes

The EGFR expressing human cell lines including: epidermoid carcinoma cell line, A431, the human breast carcinoma cell lines MDA-MB-468 and MDA-MB-231, the human colon tumor cell line, HCT 116; and the EGFR-negative human carcinoma cell line MCF-7 were used to investigate targeted delivery potential of the peptide-targeted liposome.

For the binding and internalization studies, cells were harvested from adherent cultures using trypsin, resuspended as individualized cells, and rejuvenated for 1 hour at 37° C. prior to use. About one million cells in suspension were treated with Stealth® liposomes with Alexa 488-dextran (MW 10,000) targeted with P190 (P190-SL) or SL without P190 at a concentration of 240 mmole/ml of total lipid concentration in serum free media. For cell binding studies, the cells were treated for 30 min at 4° C. with mild shaking (rotary mixer at 140 rpm). Then, the cells were washed and spun down twice at 2000 rpm at 4° C. for 5 minutes. For the cell internalization study, the cells were incubated at 37° C. for 15 or 30 minutes with P190-conjugate targeted or naked SL containing Alexa 488-dextran. Following the incubation, the cells were washed, resuspended in cell culture medium containing 10% serum, and incubated at 37° C. for another 2 hours. At the end of the incubations, 1 ml of cold serum free medium was added, the cells were pelleted at 4° C., resuspended in cold serum free medium and vigorously shaken (440 rpm) for 10 min at 4° C. Thereafter the cells were pelleted and all but 100 ul of media removed. An aliquot, 6 ul, was dropped on a glass slide for confocal fluorescence microscopy using a Nikon ECLIPSE E600W.

Results

Due to the fluorescence of the Alexa, specific binding P190-SL could be observed around the cell surface of both A431 and MDA-MB-468 cells using the confocal microscope. No fluorescence could be detected inside of the cells, consistent with the internalization of the target liposomes proceeding by endocytosis which, being an energy requiring biological process, is inhibited at 4° C. Moreover, no fluorescence was observed from the cells that were treated with untargeted liposomes. For the 37° C. incubated samples, Alexa 488 fluorescence was evident inside the cells treated with P190-targeted SL, whereas there was no fluorescence that was shown in the cells treated with SL without P190 conjugation. The EFGR-negative cell line, human breast tumor cell line MCF-7, showed no binding and internalization when treated with P190-SL in the same manner as above. While the HCT116 and MCA-MB-231 have been reported to be EGFR positive, no fluorescence was detected on these cells using the P190-targeted liposomes.

Example 11

In Vitro Activity of EGFR-Targeted Liposomes

EGFR-targeted doxorubicin containing liposomes prepared as described in Example 9 were used to show that in EGFR-targeting of liposomal doxorubicin enhanced the cell killing of this form of encapsulated doxorubicin.

For the cytotoxicity assay, EGFR expressing human tumor cells, A431, MDA-MB-468 and MDA-MB-231 were used. The cells were harvested from adherent cultures using trypsin, resuspended as individualized cells, and rejuvenated for 1 hour at 37° C. prior to use. Cells ($1 \times 10^{\wedge}6$ per ml per test tube) were incubated at 37° C. for 2 hours in cell culture medium with FBS and were shaken mildly. The cells were spun down at 2000 rpm for 5 minutes, and supernatant was discarded. The treatment solution of DOXIL (STEALTH® liposomes containing doxorubicin) or P190-DOXIL was diluted with cell culture medium without FBS to provide various concentrations in 0.1 ml for each test tube. Cell culture medium without FBS was added to the cells as a control. The cells were incubated with mild shaking at 37° C. for 1 or 4 hours. The treatment was stopped by adding 1 ml of cell culture medium without FBS. The cells were spun down and were washed with 1 ml of cell culture medium without FBS. The cells were shaken vigorously at 37° C. for 10 minutes and washing was repeated. Cells were re-suspended with 1 ml of cell culture medium with FBS. The cells were counted, and seeded 2,000 to 4,000 cells per well of 96-well plate in triplet for each treatment point. The cells were incubated at 37° C. for 4-6 days, and the viable cells determined using the Promega CellTiter 96® Aqueous One Solution Cell Proliferation Assay (a tetrazolium based colorimetric method for determining the number of viable cells in proliferation) at 490 nm with a microplate reader. Cell viability was calculated as % of untreated control using the formula:

% Viability=$(A-A_0)/(A_{100}-A_0) \times 100\%$

Where A is the measured absorbance, $A_0$ is the absorbance of the blanks, and $A_{100}$ is the absorbance of the wells with untreated cells. Percent cell viability was plotted as a function of drug concentration and $IC_{50}$ (concentration resulting in 50% cell growth inhibition) was determined by interpolation.

Results

Figure 12:
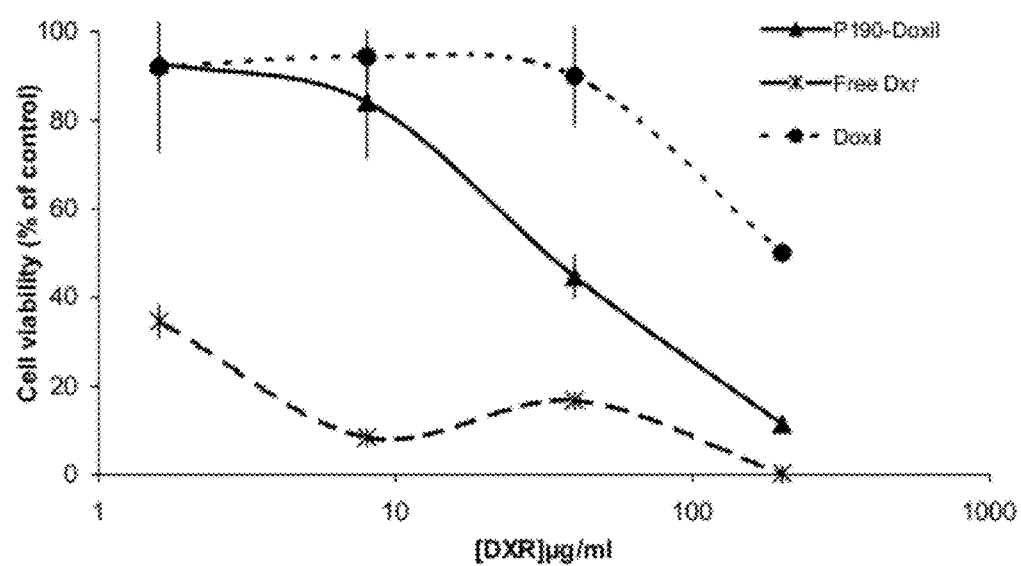
FIG. 12 is a plot of cell viability vs doxorubicin (free Dxr) concentration for liposomal and free doxorubicin where liposomal doxorubicin is DOXIL either as naked liposomes or DOXIL targeted to EGFR by the insertion of PEG-lipid conjugated P190 on the liposomal surface (P190-DOXIL).

FIG. 12 shows the results of the cytotoxicity experiment wherein, DOXIL liposomes which are untargeted are compared to DOXIL liposomes with P190-PEG-Lipid inserted on the surface (P190-DOXIL) and to the molar equivalent of free doxorubicin (Dxr) on A431 cells after treatment for 4 h and then incubation for 6 D. While free doxorubicin can penetrate cell membranes due to its inherent lipophilicity and cause cell killing, liposomally formulated doxorubicin as DOXIL impedes free penetration of drug to cell membranes. However, as P190-targeted DOXIL displays and EC50 much lower than naked DOXIL, it can be inferred that the drug is being internalized due to EGFR binding and endocytosis stimulated by P190 binding to the receptor. In contrast, there was no cell growth inhibition for EGFR-negative expressing cells (MCF7) treated with P190-SL-dox in the same condition as above (the data is not shown).

Similarly, treatment of MCB-MB-468 for 1 h and then incubation for 4 or 6 days resulted in cell killing by free doxorubicin, less killing by untargeted DOXIL liposomes, and an intermediate level of activity by the P190-target DOXIL liposomes as shown in the table below.

| Treatment | IC50 D4 (ug/ml) | IC50 D6 (ug/ml) |
|---|---|---|
| DOXIL | >200 | 200 |
| Doxorubicin | 2.5 | <1.6 |
| P190-DOXIL | 120 | 35 |

Consistent with the cell binding results of Example 10, the MCB-MB-231 cells did not exhibit enhanced cell killing by P190-DOXIL relative to the untargeted liposome.

Example 12

P190-MIMETIBODY Construct

A peptide-Fc fusion protein described herein as a MIMETIBODY and based on formula I below were engineered with various modifications in the flexible linker region, FLEX of formula I using P190 (SEQ ID NO: 55) as the Pep fragment in monomeric format, V1 is replaced by the gly-gly of the phage fusion and o equals 1, m equals 0, and the Hinge, CH2 and CH3 are derived from an human IgG4 sequence wherein two leucine residues in the lower hinge/CH2 are mutated to alanine residues. The complete sequence of the polypeptide monomer is given in SEQ ID NO: 60 where residues 26-28 represent the Flex segment which is elongaed in the different construct variations as shown in Table 11.

$$V1_o\text{-}Pep_a\text{-}Flex_n\text{-}V2_m\text{-}Hinge\text{-}CH2\text{-}CH3 \qquad (I)$$

TABLE 11

| Construct | Pep | Flex | n | SEQ ID NO: |
|---|---|---|---|---|
| 4314 | DPCTWEVWGRECLQ | GGGS | 1 | SEQ ID NO: 79 |
| 4315 | DPCTWEVWGRECLQ | GGGGS | 2 | SEQ ID NO: 80 |
| 4316 | DPCTWEVWGRECLQ | GGGGS | 4 | SEQ ID NO: 81 |

Results

Figure 13:
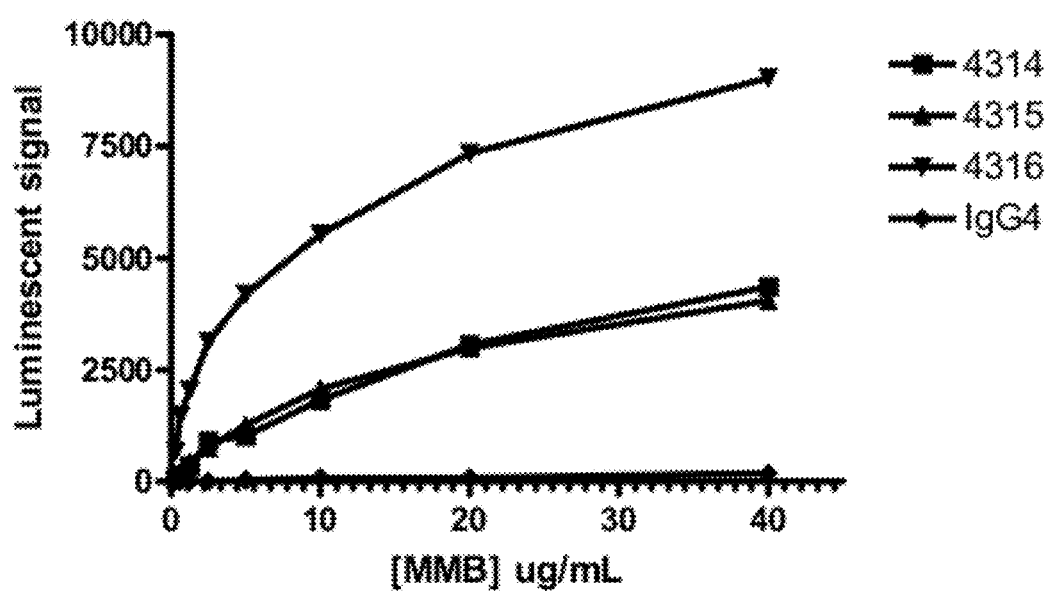
FIG. 13 is a plot signal generated from immobilized sEGFR-MMB (ELISA format) by variants of a P190-MMB made with different lengths of flexible linker between the peptide and the hinge domain.
Figure 14:
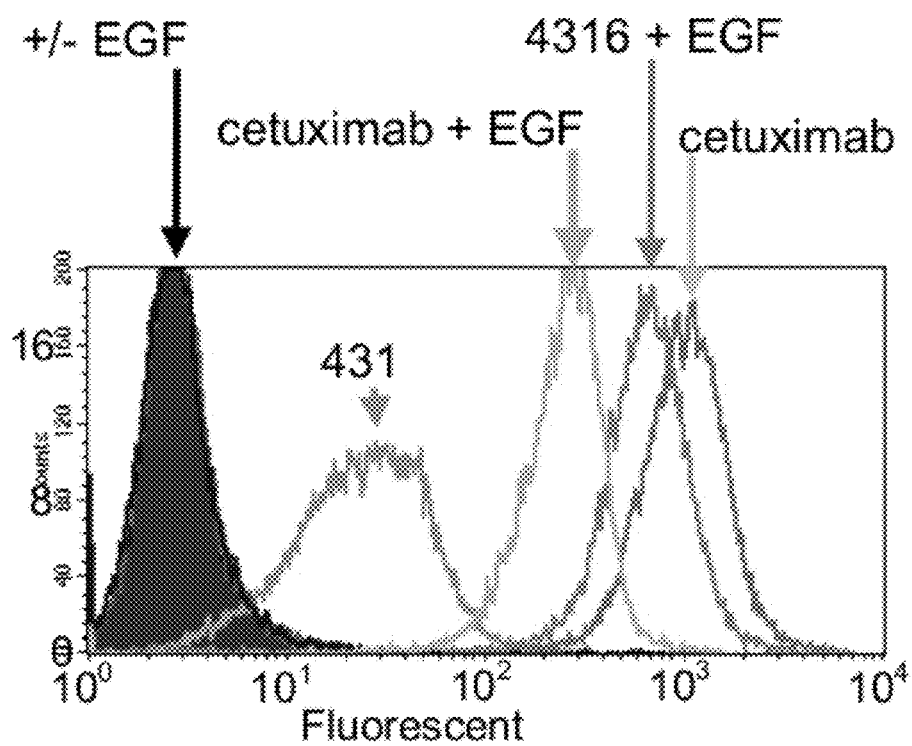
FIG. 14 shows FACS generated histograms overlaid to show the shift in intensity of binding to A431 cells for P190-MMB constructs or cetuximab in the presence or absence of EGF.

The construct with the longest linker (4316) was shown to be the best binder using both solid phase assays, BIAcore and ELISA, and the cell-based FACS performed as described previously. While the BiaCore data could not provide a dissocation constant, 4316 showed much more pronounced on-rate than the other constructs. The binding data against immobilized sEGFR-MMB are shown in FIG. 13. FACS analysis with MCF7 and A431 cells, demonstrated no non-specific binding to MCF7, little binding of 4313 and 4315 to A431, but about a 10-fold increase in signal for 4316 alone. In addition, recombinant human EGF (rhEGF) enhanced binding of the P190-4316 construct to EGFR (A431) while the presence of EGF reduced binding of cetuximab (FIG. 14). FIG. 14 shows the secondary labeled Ab (1996) in the presence of EGF does not cause cell staining (no background binding). Cetuximab, binds EGFR+A431 but an excess of EGF reduces cetuximab bind to the cells. In contrast, 190-MMB as the 4316 construct, binds EGFR and the presence of excess EGF promotes its binding. These findings are consistent with the behavior of free P190 and demonstrate that the MMB format did not alter the binding specificities of the peptide.

In addition, FACE™ (Fast Activated Cell-based ELISA), a cell-based method to monitor proteins activated by phosphorylation, was used to show P190-MMB-4316 did not induce EGFR phosphorylation (receptor activation) in the absence of EGF nor interfere with EGF activation of EGFR. These results indicated P190 is a non-agonist EGFR targeting peptide.

TABLE 8

Summary of ELISA profiles for EGFR-MMB selected phage

| Phage-Peptide | SEQ ID | Amino Acid Sequence | Peptide Library | Binds sEGFR-MMB | Binds b-sEGFR-MMB | Binds b-sEGFR-His | Compete with EGF | Compete with TGF | Compete with Cetuximab |
|---|---|---|---|---|---|---|---|---|---|
| P173 | 31 | TDCVIFGLETYCLR | 8-mer cyclic pIX | + | + | − | − | − | − |
| P174 | 51 | SGCLDALWQCVY | 6-mer cyclic pIX | + | + | + | − | − | − |
| P175 | 13 | LPDDSLPELICKVRG | 15-mer linear pIX | + | + | − | − | − | − |
| P176 | 48 | KTCVSTTFDLWFVCFA | 10-mer cyclic pIX | + | + | + | + | + | + |
| P179 | 39 | GPCVLIRDYYLLCLE | 9-mer cyclic pIX | + | − | − | − | − | − |
| P145 | 7 | VLCHRYYHPICYT | 7-mer cyclic pIII | + | + | + | + | + | + |
| EGF-pIX | NA | TDCVIFGLETYCLR | | + | + | + | + | + | + |

"b-" = biotinylated protein

TABLE 10

| Phage-Peptide | SEQ ID NO: | Amino Acid Sequence | Binds sEGFR-MMB | Binds EGF + sEGFR-MMB Complex | Binds sEGFR-His6 | Competes with EGF | Competes with TGFa | Competes with cetuximab |
|---|---|---|---|---|---|---|---|---|
| P189 | 54 | MFCFRWYAGWSCVS | ++ | − | ++ | ++ | ++ | +++ |
| P190 | 55 | DPCTWEVWGRECLQ | + | ++++ | − | − | − | + |
| P191 | 56 | HFYPTKTPGY | − | + | − | − | − | − |
| P192 | 57 | AASRALWAFNSD | − | + | − | − | + | − |
| P193 | 58 | SYYWGYTVDIRR | + | ++ | − | − | − | ++ |
| P194 | 59 | SECFPLAPDWLSCIL | ++++ | − | +++ | ++++ | +++ | ++++ |
| EGF-pIII | | | ++++ | − | ++++ | ++ | + | ++++ |
| P173 | 31 | TDCVIFGLETYCLR | +++ | ++++ | − | + | + | ++ |

What is to be claimed:

1. A composition comprising a fusion protein according to the formula:

$$V1_o\text{-Pep}_a\text{-Flex}_n\text{-}V2_m\text{-Hinge-CH2-CH3} \quad (I)$$

and wherein Pep represents domains I to III of human EGFR capable of binding EGF with an affinity of less than 1 nM when measured by BIAcore, V1 is the sequence QIQ, Flex is a flexible linker peptide, V2 represents a sequence derived from an immunoglobulin J gene domain and is TLVTVSS (SEQ ID No:61), the hinge, CH2 and CH3 are domains from a human $IgG_1$ and each of a, m, n and o is equal to 1, wherein the fusion protein comprises SEQ ID NO:2.

2. A dimeric polypeptide comprising two polypeptides of sequence SEQ ID NO:2.

* * * * *

SEQUENCE LISTING

<160> NUMBER OF SEQ ID NOS: 81

<210> SEQ ID NO 1
<211> LENGTH: 627
<212> TYPE: PRT
<213> ORGANISM: Artificial Sequence
<220> FEATURE:
<223> OTHER INFORMATION: Human EGFR extracellular domain, His-tagged
<220> FEATURE:
<221> NAME/KEY: DOMAIN
<222> LOCATION: (1)..(164)
<223> OTHER INFORMATION: Leucine-rich domain I
<220> FEATURE:
<221> NAME/KEY: DOMAIN
<222> LOCATION: (165)..(309)
<223> OTHER INFORMATION: Cysteine-rich domain II
<220> FEATURE:
<221> NAME/KEY: DOMAIN
<222> LOCATION: (310)..(479)
<223> OTHER INFORMATION: Leucine-rich domain III
<220> FEATURE:
<221> NAME/KEY: DOMAIN
<222> LOCATION: (480)..(621)
<223> OTHER INFORMATION: Cysteine-rich domain IV
<220> FEATURE:
<221> NAME/KEY: METAL
<222> LOCATION: (622)..(627)
<223> OTHER INFORMATION: Binds to zinc or other metals for purification

<400> SEQUENCE: 1

```
Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
```

```
                    245                 250                 255
Pro Glu Gly Lys Tyr Ser Phe Gly Ala Thr Cys Val Lys Lys Cys Pro
                260                 265                 270

Arg Asn Tyr Val Val Thr Asp His Gly Ser Cys Val Arg Ala Cys Gly
            275                 280                 285

Ala Asp Ser Tyr Glu Met Glu Glu Asp Gly Val Arg Lys Cys Lys Lys
        290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser His His His
    610                 615                 620

His His His
625

<210> SEQ ID NO 2
<211> LENGTH: 870
<212> TYPE: PRT
<213> ORGANISM: Artificial Sequence
<220> FEATURE:
```

```
<223> OTHER INFORMATION: Human extracellular EGFR fused to human Ig
      constant domains
<220> FEATURE:
<221> NAME/KEY: DOMAIN
<222> LOCATION: (1)..(3)
<223> OTHER INFORMATION: Human IgG N-terminus
<220> FEATURE:
<221> NAME/KEY: DOMAIN
<222> LOCATION: (4)..(624)
<223> OTHER INFORMATION: Human EGFR extracellular domain
<220> FEATURE:
<221> NAME/KEY: DOMAIN
<222> LOCATION: (625)..(630)
<223> OTHER INFORMATION: Linker
<220> FEATURE:
<221> NAME/KEY: DOMAIN
<222> LOCATION: (631)..(638)
<223> OTHER INFORMATION: Ig "J" domain
<220> FEATURE:
<221> NAME/KEY: DOMAIN
<222> LOCATION: (639)..(653)
<223> OTHER INFORMATION: Ig hinge
<220> FEATURE:
<221> NAME/KEY: DOMAIN
<222> LOCATION: (654)..(870)
<223> OTHER INFORMATION: Ig CH2 and CH3

<400> SEQUENCE: 2

Gln Ile Gln Leu Glu Glu Lys Val Cys Gln Gly Thr Ser Asn Lys
 1               5                  10                  15

Leu Thr Gln Leu Gly Thr Phe Glu Asp His Phe Leu Ser Leu Gln Arg
             20                  25                  30

Met Phe Asn Asn Cys Glu Val Val Leu Gly Asn Leu Glu Ile Thr Tyr
         35                  40                  45

Val Gln Arg Asn Tyr Asp Leu Ser Phe Leu Lys Thr Ile Gln Glu Val
50                  55                  60

Ala Gly Tyr Val Leu Ile Ala Leu Asn Thr Val Glu Arg Ile Pro Leu
65                  70                  75                  80

Glu Asn Leu Gln Ile Ile Arg Gly Asn Met Tyr Tyr Glu Asn Ser Tyr
                 85                  90                  95

Ala Leu Ala Val Leu Ser Asn Tyr Asp Ala Asn Lys Thr Gly Leu Lys
            100                 105                 110

Glu Leu Pro Met Arg Asn Leu Gln Glu Ile Leu His Gly Ala Val Arg
        115                 120                 125

Phe Ser Asn Asn Pro Ala Leu Cys Asn Val Glu Ser Ile Gln Trp Arg
130                 135                 140

Asp Ile Val Ser Ser Asp Phe Leu Ser Asn Met Ser Met Asp Phe Gln
145                 150                 155                 160

Asn His Leu Gly Ser Cys Gln Lys Cys Asp Pro Ser Cys Pro Asn Gly
                165                 170                 175

Ser Cys Trp Gly Ala Gly Glu Glu Asn Cys Gln Lys Leu Thr Lys Ile
            180                 185                 190

Ile Cys Ala Gln Gln Cys Ser Gly Arg Cys Arg Gly Lys Ser Pro Ser
        195                 200                 205

Asp Cys Cys His Asn Gln Cys Ala Ala Gly Cys Thr Gly Pro Arg Glu
210                 215                 220

Ser Asp Cys Leu Val Cys Arg Lys Phe Arg Asp Glu Ala Thr Cys Lys
225                 230                 235                 240

Asp Thr Cys Pro Pro Leu Met Leu Tyr Asn Pro Thr Thr Tyr Gln Met
                245                 250                 255

Asp Val Asn Pro Glu Gly Lys Tyr Ser Phe Gly Ala Thr Cys Val Lys
            260                 265                 270
```

-continued

```
Lys Cys Pro Arg Asn Tyr Val Thr Asp His Gly Ser Cys Val Arg
        275                 280                 285
Ala Cys Gly Ala Asp Ser Tyr Glu Met Glu Glu Asp Gly Val Arg Lys
    290                 295                 300
Cys Lys Cys Glu Gly Pro Cys Arg Lys Val Cys Asn Gly Ile Gly
305                 310                 315                 320
Ile Gly Glu Phe Lys Asp Ser Leu Ser Ile Asn Ala Thr Asn Ile Lys
                325                 330                 335
His Phe Lys Asn Cys Thr Ser Ile Ser Gly Asp Leu His Ile Leu Pro
                340                 345                 350
Val Ala Phe Arg Gly Asp Ser Phe Thr His Thr Pro Pro Leu Asp Pro
            355                 360                 365
Gln Glu Leu Asp Ile Leu Lys Thr Val Lys Glu Ile Thr Gly Phe Leu
    370                 375                 380
Leu Ile Gln Ala Trp Pro Glu Asn Arg Thr Asp Leu His Ala Phe Glu
385                 390                 395                 400
Asn Leu Glu Ile Ile Arg Gly Arg Thr Lys Gln His Gly Gln Phe Ser
                405                 410                 415
Leu Ala Val Val Ser Leu Asn Ile Thr Ser Leu Gly Leu Arg Ser Leu
            420                 425                 430
Lys Glu Ile Ser Asp Gly Asp Val Ile Ile Ser Gly Asn Lys Asn Leu
    435                 440                 445
Cys Tyr Ala Asn Thr Ile Asn Trp Lys Lys Leu Phe Gly Thr Ser Gly
450                 455                 460
Gln Lys Thr Lys Ile Ile Ser Asn Arg Gly Glu Asn Ser Cys Lys Ala
465                 470                 475                 480
Thr Gly Gln Val Cys His Ala Leu Cys Ser Pro Glu Gly Cys Trp Gly
                485                 490                 495
Pro Glu Pro Arg Asp Cys Val Ser Cys Arg Asn Val Ser Arg Gly Arg
                500                 505                 510
Glu Cys Val Asp Lys Cys Asn Leu Leu Glu Gly Glu Pro Arg Glu Phe
    515                 520                 525
Val Glu Asn Ser Glu Cys Ile Gln Cys His Pro Glu Cys Leu Pro Gln
    530                 535                 540
Ala Met Asn Ile Thr Cys Thr Gly Arg Gly Pro Asp Asn Cys Ile Gln
545                 550                 555                 560
Cys Ala His Tyr Ile Asp Gly Pro His Cys Val Lys Thr Cys Pro Ala
                565                 570                 575
Gly Val Met Gly Glu Asn Asn Thr Leu Val Trp Lys Tyr Ala Asp Ala
            580                 585                 590
Gly His Val Cys His Leu Cys His Pro Asn Cys Thr Tyr Gly Cys Thr
        595                 600                 605
Gly Pro Gly Leu Glu Gly Cys Pro Thr Asn Gly Pro Lys Ile Pro Ser
    610                 615                 620
Arg Ser Gly Gly Gly Ser Gly Thr Leu Val Thr Val Ser Ser Glu Pro
625                 630                 635                 640
Lys Ser Cys Asp Lys Thr His Thr Cys Pro Pro Cys Pro Ala Pro Glu
                645                 650                 655
Leu Leu Gly Gly Pro Ser Val Phe Leu Phe Pro Pro Lys Pro Lys Asp
            660                 665                 670
Thr Leu Met Ile Ser Arg Thr Pro Glu Val Thr Cys Val Val Val Asp
        675                 680                 685
Val Ser His Glu Asp Pro Glu Val Lys Phe Asn Trp Tyr Val Asp Gly
    690                 695                 700
```

```
Val Glu Val His Asn Ala Lys Thr Lys Pro Arg Glu Glu Gln Tyr Asn
705                 710                 715                 720

Ser Thr Tyr Arg Val Val Ser Val Leu Thr Val Leu His Gln Asp Trp
            725                 730                 735

Leu Asn Gly Lys Glu Tyr Lys Cys Lys Val Ser Asn Lys Ala Leu Pro
        740                 745                 750

Ala Pro Ile Glu Lys Thr Ile Ser Lys Ala Lys Gly Gln Pro Arg Glu
            755                 760                 765

Pro Gln Val Tyr Thr Leu Pro Pro Ser Arg Asp Glu Leu Thr Lys Asn
770                 775                 780

Gln Val Ser Leu Thr Cys Leu Val Lys Gly Phe Tyr Pro Ser Asp Ile
785                 790                 795                 800

Ala Val Glu Trp Glu Ser Asn Gly Gln Pro Glu Asn Asn Tyr Lys Thr
            805                 810                 815

Thr Pro Pro Val Leu Asp Ser Asp Gly Ser Phe Phe Leu Tyr Ser Lys
            820                 825                 830

Leu Thr Val Asp Lys Ser Arg Trp Gln Gln Gly Asn Val Phe Ser Cys
            835                 840                 845

Ser Val Met His Glu Ala Leu His Asn His Tyr Thr Gln Lys Ser Leu
850                 855                 860

Ser Leu Ser Pro Gly Lys
865                 870

<210> SEQ ID NO 3
<211> LENGTH: 245
<212> TYPE: PRT
<213> ORGANISM: Artificial Sequence
<220> FEATURE:
<223> OTHER INFORMATION: Variable domain truncated human IgG1 antibody
<220> FEATURE:
<221> NAME/KEY: MISC_FEATURE
<222> LOCATION: (1)..(3)
<223> OTHER INFORMATION: Human IgG1 Variable N-terminal residues
<220> FEATURE:
<221> NAME/KEY: MISC_FEATURE
<222> LOCATION: (4)..(13)
<223> OTHER INFORMATION: Human IgG variable J-derived sequences
<220> FEATURE:
<221> NAME/KEY: MISC_FEATURE
<222> LOCATION: (14)..(28)
<223> OTHER INFORMATION: Human IgG hinge region
<220> FEATURE:
<221> NAME/KEY: MISC_FEATURE
<222> LOCATION: (29)..(202)
<223> OTHER INFORMATION: Human IgG1 constant regions (C2 and C3)

<400> SEQUENCE: 3

Gln Ile Gln Gly Thr Leu Val Thr Val Ser Ser Ala Ala Glu Pro Lys
1               5                   10                  15

Ser Cys Asp Lys Thr His Thr Cys Pro Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110
```

```
Asn Gly Lys Glu Tyr Lys Cys Lys Val Ser Asn Lys Ala Leu Pro Ala
            115                 120                 125
Pro Ile Glu Lys Thr Ile Ser Lys Ala Lys Gly Gln Pro Arg Glu Pro
    130                 135                 140
Gln Val Tyr Thr Leu Pro Pro Ser Arg Asp Glu Leu Thr Lys Asn Gln
145                 150                 155                 160
Val Ser Leu Thr Cys Leu Val Lys Gly Phe Tyr Pro Ser Asp Ile Ala
                165                 170                 175
Val Glu Trp Glu Ser Asn Gly Gln Pro Glu Asn Asn Tyr Lys Thr Thr
            180                 185                 190
Pro Pro Val Leu Asp Ser Asp Gly Ser Phe Phe Leu Tyr Ser Lys Leu
        195                 200                 205
Thr Val Asp Lys Ser Arg Trp Gln Gln Gly Asn Val Phe Ser Cys Ser
    210                 215                 220
Val Met His Glu Ala Leu His Asn His Tyr Thr Gln Lys Ser Leu Ser
225                 230                 235                 240
Leu Ser Pro Gly Lys
                245

<210> SEQ ID NO 4
<211> LENGTH: 43
<212> TYPE: DNA
<213> ORGANISM: Homo sapiens

<400> SEQUENCE: 4
aagtatacag gcccagatcc agctggagga aagaaagtt tgc                       43

<210> SEQ ID NO 5
<211> LENGTH: 27
<212> TYPE: DNA
<213> ORGANISM: Homo sapiens

<400> SEQUENCE: 5
aaagatctgg acgggatctt aggccca                                        27

<210> SEQ ID NO 6
<211> LENGTH: 13
<212> TYPE: PRT
<213> ORGANISM: Artificial Sequence
<220> FEATURE:
<223> OTHER INFORMATION: Random peptide

<400> SEQUENCE: 6

Val Leu Cys Ser Asn Phe Tyr His Pro Leu Cys His Ser
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Random Peptide

<400> SEQUENCE: 7

Val Leu Cys His Arg Tyr Tyr His Pro Ile Cys Tyr Thr
1               5                   10

<210> SEQ ID NO 8
<211> LENGTH: 13
<212> TYPE: PRT
<213> ORGANISM: Artificial Sequence
<220> FEATURE:
```

-continued

<223> OTHER INFORMATION: Random peptide

<400> SEQUENCE: 8

Thr Leu Cys Arg Ser Phe Phe His Pro Leu Cys Tyr Ala
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Random peptide
<220> FEATURE:
<221> NAME/KEY: Mutagen
<222> LOCATION: (3)..(4)
<223> OTHER INFORMATION: may be any naturally occurring amino acid
<220> FEATURE:
<221> NAME/KEY: Mutagen
<222> LOCATION: (5)..(6)
<223> OTHER INFORMATION: aa are independently, F or Y

<400> SEQUENCE: 9

Leu Cys Xaa Xaa Xaa Xaa His Pro Leu Cys
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Random peptide

<400> SEQUENCE: 10

Tyr Arg Leu Phe Val Asp Glu Ser Ile Phe Phe Cys Thr Arg Leu
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Random peptide

<400> SEQUENCE: 11

Glu Leu Gly Leu Pro Thr Leu Leu Cys Trp Pro Thr Asp Thr Leu
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Random peptide

<400> SEQUENCE: 12

Val Ser Gly Ile Leu Pro Ile Leu Val Cys His Pro Ala Ala Thr
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Random peptide

<400> SEQUENCE: 13

Leu Pro Asp Asp Ser Leu Pro Glu Leu Ile Cys Lys Val Arg Gly
1               5                   10                  15

```
<210> SEQ ID NO 14
<211> LENGTH: 15
<212> TYPE: PRT
<213> ORGANISM: Artificial Sequence
<220> FEATURE:
<223> OTHER INFORMATION: Random peptide

<400> SEQUENCE: 14

His Val Ser Leu Gln Ser Leu Pro Glu Leu Ile Cys Val Val Ser
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Random peptide

<400> SEQUENCE: 15

Asn Trp Phe Ser Leu Pro Thr Leu Leu Cys Phe Pro Leu Asn Pro
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Random peptide

<400> SEQUENCE: 16

Ser Thr Ile Thr Ser Leu Pro Thr Leu Gln Cys Trp Pro Ile Leu
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Random peptide

<400> SEQUENCE: 17

Pro Ile Asp Asp Glu Ser Leu Pro Val Leu Tyr Cys Val Thr Ser
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Random peptide

<400> SEQUENCE: 18

Pro Ile Phe Ser Ser Leu Pro Val Leu Tyr Cys Thr Ser Gln Leu
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Random peptide

<400> SEQUENCE: 19

Gly Ala Asp Thr Leu Pro Asp Leu Leu Cys Trp Glu Ser Ser Leu
1               5                   10                  15

<210> SEQ ID NO 20
```

```
<211> LENGTH: 15
<212> TYPE: PRT
<213> ORGANISM: Artificial Sequence
<220> FEATURE:
<223> OTHER INFORMATION: Random peptide

<400> SEQUENCE: 20

Thr Val Phe Thr Leu Pro Glu Leu Val Cys Val Val Ala Gly Thr
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Random peptide

<400> SEQUENCE: 21

Leu Pro Asp Leu Ile Cys Ala Val Asp Ser Gly Thr Ser Gly Ala
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: Random peptide
<220> FEATURE:
<221> NAME/KEY: MUTAGEN
<222> LOCATION: (4)..(4)
<223> OTHER INFORMATION: may be any natural aa

<400> SEQUENCE: 22

Ser Leu Pro Xaa Leu Leu Cys
1               5

<210> SEQ ID NO 23
<211> LENGTH: 14
<212> TYPE: PRT
<213> ORGANISM: Artificial Sequence
<220> FEATURE:
<223> OTHER INFORMATION: Random peptide

<400> SEQUENCE: 23

Ala Gly Cys Ile Ala Phe Val Asp Val Val Tyr Cys Ala Arg
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Random peptide

<400> SEQUENCE: 24

Ala Lys Cys Ile Ala Phe Gly Asn Ser Val Tyr Cys Leu Asn
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Random peptide

<400> SEQUENCE: 25

Arg Asp Cys Ile Ile Phe Asp Lys Thr Val Tyr Cys Val Ile
1               5                   10
```

```
<210> SEQ ID NO 26
<211> LENGTH: 14
<212> TYPE: PRT
<213> ORGANISM: Artificial Sequence
<220> FEATURE:
<223> OTHER INFORMATION: Random peptide

<400> SEQUENCE: 26

Lys His Cys Ile Leu Phe Glu Lys Thr Val Tyr Cys Ala Lys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Random peptide

<400> SEQUENCE: 27

Asp Ser Cys Ile Gln Phe Ala Asn Leu Leu Tyr Cys Ala Ile
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Random peptide

<400> SEQUENCE: 28

Thr Asp Cys Ile Arg Phe Gly Val Leu Trp Tyr Cys Leu Val
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Random peptide

<400> SEQUENCE: 29

Arg Ala Cys Ile Thr Phe Gly Lys Val Val Tyr Cys Glu Val
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Random peptide

<400> SEQUENCE: 30

Ala Tyr Cys Ser Phe Val Ala Gly Asp Leu Val Cys Gln Val
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Random peptide

<400> SEQUENCE: 31

Thr Asp Cys Val Ile Phe Gly Leu Glu Thr Tyr Cys Leu Arg
1               5                   10

<210> SEQ ID NO 32
```

```
<211> LENGTH: 14
<212> TYPE: PRT
<213> ORGANISM: Artificial Sequence
<220> FEATURE:
<223> OTHER INFORMATION: Random peptide

<400> SEQUENCE: 32

Ser Asp Cys Val Leu Phe Gly Ser Lys Leu Phe Cys Ser Ala
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Random peptide

<400> SEQUENCE: 33

Thr Asp Cys Val Arg Phe Gly Glu Thr Ile Tyr Cys Ile Val
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Random peptide

<400> SEQUENCE: 34

Tyr Asp Cys Val Ser Phe Gly Ala Val Ala Tyr Cys Pro Gln
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Random peptide

<400> SEQUENCE: 35

Arg Gly Cys Val Val Phe Gly Asp Asn Ile Tyr Cys Ile Val
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Consensus of several selected peptides
<220> FEATURE:
<221> NAME/KEY: Mutagen
<222> LOCATION: (3)..(3)
<223> OTHER INFORMATION: X may be any natural amino acid
<220> FEATURE:
<221> NAME/KEY: Mutagen
<222> LOCATION: (4)..(4)
<223> OTHER INFORMATION: X may be any natural amino acid
<220> FEATURE:
<221> NAME/KEY: Mutagen
<222> LOCATION: (7)..(7)
<223> OTHER INFORMATION: X may be any natural amino acid
<220> FEATURE:
<221> NAME/KEY: Mutagen
<222> LOCATION: (8)..(8)
<223> OTHER INFORMATION: X may be any natural amino acid
<220> FEATURE:
<221> NAME/KEY: Mutagen
<222> LOCATION: (9)..(9)
<223> OTHER INFORMATION: X may be any natural amino acid

<400> SEQUENCE: 36
```

```
Asp Cys Xaa Xaa Phe Gly Xaa Xaa Xaa Tyr Cys
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Random peptide

<400> SEQUENCE: 37

Met Ile Cys Tyr Leu Val Asp Ser Gly Asn Ile Ile Cys Tyr Lys
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Random peptide

<400> SEQUENCE: 38

Tyr Asp Cys Met Ile Arg Ala Asp Gly Ser Leu Ile Cys Trp Cys
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Random peptide

<400> SEQUENCE: 39

Gly Pro Cys Val Leu Ile Arg Asp Tyr Tyr Leu Leu Cys Leu Glu
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Random peptide

<400> SEQUENCE: 40

Ala Phe Cys Arg Leu Asp Phe Asn Gln Trp Leu Thr Cys Leu Val
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Random peptide

<400> SEQUENCE: 41

Cys Asp Cys Arg Glu Ala Val Ser Ala Ser Leu Val Cys Arg Tyr
1               5                   10                  15

<210> SEQ ID NO 42
<211> LENGTH: 11
<212> TYPE: PRT
<213> ORGANISM: Artificial Sequence
<220> FEATURE:
<223> OTHER INFORMATION: Consensus of several selected peptides
<220> FEATURE:
<221> NAME/KEY: Mutagen
<222> LOCATION: (2)..(2)
<223> OTHER INFORMATION: X may be any natural amino acid
<220> FEATURE:
```

```
<221> NAME/KEY: Mutagen
<222> LOCATION: (4)..(4)
<223> OTHER INFORMATION: X may be any natural amino acid
<220> FEATURE:
<221> NAME/KEY: Mutagen
<222> LOCATION: (5)..(5)
<223> OTHER INFORMATION: X may be any natural amino acid
<220> FEATURE:
<221> NAME/KEY: Mutagen
<222> LOCATION: (7)..(7)
<223> OTHER INFORMATION: X may be any natural amino acid
<220> FEATURE:
<221> NAME/KEY: Mutagen
<222> LOCATION: (8)..(8)
<223> OTHER INFORMATION: X may be any natural amino acid
<220> FEATURE:
<221> NAME/KEY: Mutagen
<222> LOCATION: (9)..(9)
<223> OTHER INFORMATION: X may be any natural amino acid
<220> FEATURE:
<221> NAME/KEY: Mutagen
<222> LOCATION: (10)..(10)
<223> OTHER INFORMATION: X may be any natural amino acid

<400> SEQUENCE: 42

Cys Xaa Leu Xaa Xaa Asp Xaa Xaa Xaa Xaa Cys
1               5                  10

<210> SEQ ID NO 43
<211> LENGTH: 16
<212> TYPE: PRT
<213> ORGANISM: Artificial Sequence
<220> FEATURE:
<223> OTHER INFORMATION: Random peptide

<400> SEQUENCE: 43

Pro Thr Cys Asp Ser Ala Thr Arg Arg Val Leu Thr Ile Cys Ala Asp
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Random peptide

<400> SEQUENCE: 44

Trp Met Cys Phe Leu Glu Gly Tyr Gly Ala Ser Leu Met Cys Gln Cys
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Random peptide

<400> SEQUENCE: 45

Asp Ser Cys Cys Ser Phe Leu Thr Asp Gly Thr Val Val Cys Ser Leu
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Random peptide

<400> SEQUENCE: 46

Tyr Ile Cys Thr Pro Ser Asp Ile Asp Ser Trp Tyr Ile Cys Tyr Leu
1               5                   10                  15
```

<210> SEQ ID NO 47
<211> LENGTH: 16
<212> TYPE: PRT
<213> ORGANISM: Artificial Sequence
<220> FEATURE:
<223> OTHER INFORMATION: Random peptide

<400> SEQUENCE: 47

Ser Val Cys Val Gly Thr Ala Phe Pro Gly Trp Met Val Cys Gly Pro
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Random peptide

<400> SEQUENCE: 48

Lys Thr Cys Val Ser Thr Thr Phe Asp Leu Trp Phe Val Cys Phe Ala
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Random peptide

<400> SEQUENCE: 49

Leu Leu Cys Ala Thr Thr Ser Phe Arg Asp Trp Phe Val Cys Phe Thr
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Consensus of several selected peptides
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid

<400> SEQUENCE: 50

Xaa Xaa Cys Xaa Xaa Thr Xaa Phe Asp Xaa Trp Xaa Val Cys Xaa Xaa
1               5                   10                  15

<210> SEQ ID NO 51
<211> LENGTH: 12

```
<212> TYPE: PRT
<213> ORGANISM: Artificial Sequence
<220> FEATURE:
<223> OTHER INFORMATION: Random peptide

<400> SEQUENCE: 51

Ser Gly Cys Leu Asp Ala Leu Trp Gln Cys Val Tyr
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Random peptide

<400> SEQUENCE: 52

Asp Ala Cys Thr Met Val Phe Leu Trp Cys Ser Leu
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Random peptide

<400> SEQUENCE: 53

Arg Trp Cys Tyr Phe Trp Trp Ile Thr Ile Cys Glu Leu
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Random peptide

<400> SEQUENCE: 54

Met Phe Cys Phe Arg Trp Tyr Ala Gly Trp Ser Cys Val Ser
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Random peptide

<400> SEQUENCE: 55

Asp Pro Cys Thr Trp Glu Val Trp Gly Arg Glu Cys Leu Gln
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Random peptide

<400> SEQUENCE: 56

His Phe Tyr Pro Thr Lys Thr Pro Gly Tyr
1               5                   10

<210> SEQ ID NO 57
<211> LENGTH: 12
<212> TYPE: PRT
<213> ORGANISM: Artificial Sequence
```

```
<220> FEATURE:
<223> OTHER INFORMATION: Random peptide

<400> SEQUENCE: 57

Ala Ala Ser Arg Ala Leu Trp Ala Phe Asn Ser Asp
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Random peptide

<400> SEQUENCE: 58

Ser Tyr Tyr Trp Gly Tyr Thr Val Asp Ile Arg Arg
1               5                   10

<210> SEQ ID NO 59
<211> LENGTH: 15
<212> TYPE: PRT
<213> ORGANISM: Artificial Sequence
<220> FEATURE:
<223> OTHER INFORMATION: Random peptide

<400> SEQUENCE: 59

Ser Glu Cys Phe Pro Leu Ala Pro Asp Trp Leu Ser Cys Ile Leu
1               5                   10                  15

<210> SEQ ID NO 60
<211> LENGTH: 242
<212> TYPE: PRT
<213> ORGANISM: Artificial Sequence
<220> FEATURE:
<223> OTHER INFORMATION: Synthetic peptide fused to human IgG4 derived
      constant domains.
<220> FEATURE:
<221> NAME/KEY: DOMAIN
<222> LOCATION: (1)..(2)
<223> OTHER INFORMATION: Phage display remnant
<220> FEATURE:
<221> NAME/KEY: PEPTIDE
<222> LOCATION: (3)..(16)
<223> OTHER INFORMATION: P190, identified EGFR-binding peptide
<220> FEATURE:
<221> NAME/KEY: FLEX
<222> LOCATION: (17)..(20)
<223> OTHER INFORMATION: Flexible linker basic unit which repeated 1, 2
      or 4 times in constructs exemplified
<220> FEATURE:
<221> NAME/KEY: FLEX
<222> LOCATION: (17)..(20)
<223> OTHER INFORMATION: Flexible linker basic unit which is lengthened
      in constructs exemplified
<220> FEATURE:
<221> NAME/KEY: DOMAIN
<222> LOCATION: (21)..(242)
<223> OTHER INFORMATION: hIgG4 derived Fc domain

<400> SEQUENCE: 60

Gly Gly Asp Pro Cys Thr Trp Glu Val Trp Gly Arg Glu Cys Leu Gln
1               5                   10                  15

Gly Gly Gly Ser Cys Pro Pro Cys Pro Ala Pro Glu Ala Ala Gly Gly
                20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser Gln Glu
        50                  55                  60

Asp Pro Glu Val Gln Phe Asn Trp Tyr Val Asp Gly Val Glu Val His
```

```
                65                  70                  75                  80
Asn Ala Lys Thr Lys Pro Arg Glu Glu Gln Phe Asn Ser Thr Tyr Arg
                    85                  90                  95
Val Val Ser Val Leu Thr Val Leu His Gln Asp Trp Leu Asn Gly Lys
                    100                 105                 110
Glu Tyr Lys Cys Lys Val Ser Asn Lys Gly Leu Pro Ser Ser Ile Glu
                    115                 120                 125
Lys Thr Ile Ser Lys Ala Lys Gly Gln Pro Arg Glu Pro Gln Val Tyr
            130                 135                 140
Thr Leu Pro Pro Ser Gln Glu Glu Met Thr Lys Asn Gln Val Ser Leu
145                 150                 155                 160
Thr Cys Leu Val Lys Gly Phe Tyr Pro Ser Asp Ile Ala Val Glu Trp
                    165                 170                 175
Glu Ser Asn Gly Gln Pro Glu Asn Asn Tyr Lys Thr Thr Pro Pro Val
                    180                 185                 190
Leu Asp Ser Asp Gly Ser Phe Phe Leu Tyr Ser Arg Leu Thr Val Asp
                    195                 200                 205
Lys Ser Arg Trp Gln Glu Gly Asn Val Phe Ser Cys Ser Val Met His
            210                 215                 220
Glu Ala Leu His Asn His Tyr Thr Gln Lys Ser Leu Ser Leu Ser Leu
225                 230                 235                 240
Gly Lys

<210> SEQ ID NO 61
<211> LENGTH: 7
<212> TYPE: PRT
<213> ORGANISM: Artificial Sequence
<220> FEATURE:
<223> OTHER INFORMATION: Derived from an immunoglobulin J gene domain

<400> SEQUENCE: 61

Thr Leu Val Thr Val Ser Ser
1               5

<210> SEQ ID NO 62
<211> LENGTH: 22
<212> TYPE: PRT
<213> ORGANISM: Artificial Sequence
<220> FEATURE:
<223> OTHER INFORMATION: A Phage peptide library constructed to promote
      the display of disulfide-constrained cyclic peptides.
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 62

Ser His Ser Ala Gly Xaa Xaa Cys Xaa Xaa Xaa Xaa Cys Xaa Xaa Gly
1               5                   10                  15

Gly Thr Val Glu Ser Cys
            20

<210> SEQ ID NO 63
<211> LENGTH: 20
<212> TYPE: PRT
```

```
<213> ORGANISM: Artificial Sequence
<220> FEATURE:
<223> OTHER INFORMATION: A Phage peptide library constructed to promote
      the display of disulfide-constrained cyclic peptides.
<220> FEATURE:
<221> NAME/KEY: misc_feature
<222> LOCATION: (6)..(13)
<223> OTHER INFORMATION: Xaa can be any naturally occurring amino acid

<400> SEQUENCE: 63

Ser His Ser Ala Gly Xaa Xaa Xaa Xaa Xaa Xaa Xaa Xaa Gly Gly Thr
1               5                   10                  15

Val Glu Ser Cys
            20

<210> SEQ ID NO 64
<211> LENGTH: 26
<212> TYPE: PRT
<213> ORGANISM: Artificial Sequence
<220> FEATURE:
<223> OTHER INFORMATION: A Phage peptide library constructed to promote
      the display of disulfide-constrained cyclic peptides.
<220> FEATURE:
<221> NAME/KEY: misc_feature
<222> LOCATION: (6)..(19)
<223> OTHER INFORMATION: Xaa can be any naturally occurring amino acid

<400> SEQUENCE: 64

Ser His Ser Ala Gly Xaa Xaa Xaa Xaa Xaa Xaa Xaa Xaa Xaa Xaa Xaa
1               5                   10                  15

Xaa Xaa Xaa Gly Gly Thr Val Glu Ser Cys
            20                  25

<210> SEQ ID NO 65
<211> LENGTH: 24
<212> TYPE: PRT
<213> ORGANISM: Artificial Sequence
<220> FEATURE:
<223> OTHER INFORMATION: A Phage peptide library constructed to promote
      the display of disulfide-constrained cyclic peptides.
<220> FEATURE:
<221> NAME/KEY: misc_feature
<222> LOCATION: (6)..(17)
<223> OTHER INFORMATION: Xaa can be any naturally occurring amino acid

<400> SEQUENCE: 65

Ser His Ser Ala Gly Xaa Xaa Xaa Xaa Xaa Xaa Xaa Xaa Xaa Xaa Xaa
1               5                   10                  15

Xaa Gly Gly Thr Val Glu Ser Cys
            20

<210> SEQ ID NO 66
<211> LENGTH: 25
<212> TYPE: PRT
<213> ORGANISM: Artificial Sequence
<220> FEATURE:
<223> OTHER INFORMATION: A Phage peptide library constructed to promote
      the display of disulfide-constrained cyclic peptides.
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
```

-continued

```
<400> SEQUENCE: 66

Ser His Ser Ala Gly Xaa Xaa Cys Xaa Xaa Xaa Xaa Xaa Xaa Xaa Cys
1               5                   10                  15

Xaa Xaa Gly Gly Thr Val Glu Ser Cys
            20                  25

<210> SEQ ID NO 67
<211> LENGTH: 26
<212> TYPE: PRT
<213> ORGANISM: Artificial Sequence
<220> FEATURE:
<223> OTHER INFORMATION: A Phage peptide library constructed to promote
      the display of disulfide-constrained cyclic peptides.
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid

<400> SEQUENCE: 67

Ser His Ser Ala Gly Xaa Xaa Cys Xaa Xaa Xaa Xaa Xaa Xaa Xaa Xaa
1               5                   10                  15

Cys Xaa Xaa Gly Gly Thr Val Glu Ser Cys
                20                  25

<210> SEQ ID NO 68
<211> LENGTH: 27
<212> TYPE: PRT
<213> ORGANISM: Artificial Sequence
<220> FEATURE:
<223> OTHER INFORMATION: A Phage peptide library constructed to promote
      the display of disulfide-constrained cyclic peptides.
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid

<400> SEQUENCE: 68

Ser His Ser Ala Gly Xaa Xaa Cys Xaa Xaa Xaa Xaa Xaa Xaa Xaa Xaa
1               5                   10                  15

Xaa Cys Xaa Xaa Gly Gly Thr Val Glu Ser Cys
                20                  25

<210> SEQ ID NO 69
<211> LENGTH: 28
<212> TYPE: PRT
<213> ORGANISM: Artificial Sequence
<220> FEATURE:
<223> OTHER INFORMATION: A Phage peptide library constructed to promote
      the display of disulfide-constrained cyclic peptides.
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
```

```
<222> LOCATION: (9)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid

<400> SEQUENCE: 69

Ser His Ser Ala Gly Xaa Xaa Cys Xaa Xaa Xaa Xaa Xaa Xaa Xaa
1               5                   10                  15

Xaa Xaa Cys Xaa Xaa Gly Gly Thr Val Glu Ser Cys
            20                  25

<210> SEQ ID NO 70
<211> LENGTH: 22
<212> TYPE: PRT
<213> ORGANISM: Artificial Sequence
<220> FEATURE:
<223> OTHER INFORMATION: A Phage peptide library constructed to promote
      the display of disulfide-constrained cyclic peptides.
<220> FEATURE:
<221> NAME/KEY: misc_feature
<222> LOCATION: (6)..(15)
<223> OTHER INFORMATION: Xaa can be any naturally occurring amino acid

<400> SEQUENCE: 70

Ser His Ser Ala Gly Xaa Xaa Xaa Xaa Xaa Xaa Xaa Xaa Xaa Xaa Gly
1               5                   10                  15

Gly Thr Val Glu Ser Cys
            20

<210> SEQ ID NO 71
<211> LENGTH: 24
<212> TYPE: PRT
<213> ORGANISM: Artificial Sequence
<220> FEATURE:
<223> OTHER INFORMATION: A Phage peptide library constructed to promote
      the display of disulfide-constrained cyclic peptides.
<220> FEATURE:
<221> NAME/KEY: misc_feature
<222> LOCATION: (6)..(17)
<223> OTHER INFORMATION: Xaa can be any naturally occurring amino acid

<400> SEQUENCE: 71

Ser His Ser Ala Gly Xaa Xaa Xaa Xaa Xaa Xaa Xaa Xaa Xaa Xaa Xaa
1               5                   10                  15

Xaa Gly Gly Thr Val Glu Ser Cys
            20

<210> SEQ ID NO 72
<211> LENGTH: 26
<212> TYPE: PRT
<213> ORGANISM: Artificial Sequence
<220> FEATURE:
<223> OTHER INFORMATION: A Phage peptide library constructed to promote
      the display of disulfide-constrained cyclic peptides.
<220> FEATURE:
<221> NAME/KEY: misc_feature
<222> LOCATION: (6)..(19)
<223> OTHER INFORMATION: Xaa can be any naturally occurring amino acid

<400> SEQUENCE: 72

Ser His Ser Ala Gly Xaa Xaa Xaa Xaa Xaa Xaa Xaa Xaa Xaa Xaa Xaa
1               5                   10                  15

Xaa Xaa Xaa Gly Gly Thr Val Glu Ser Cys
            20                  25

<210> SEQ ID NO 73
```

```
<211> LENGTH: 34
<212> TYPE: PRT
<213> ORGANISM: Artificial Sequence
<220> FEATURE:
<223> OTHER INFORMATION: Pectate lyase (pel) B signal peptide
<220> FEATURE:
<221> NAME/KEY: misc_feature
<222> LOCATION: (7)..(21)
<223> OTHER INFORMATION: Xaa can be any naturally occurring amino acid

<400> SEQUENCE: 73

Ala Met Ala Gly Gly Gly Xaa Xaa Xaa Xaa Xaa Xaa Xaa Xaa Xaa Xaa
1               5                   10                  15

Xaa Xaa Xaa Xaa Xaa Gly Gly Gly Ser Gly Gly Ser Gly Gly Met Ser
            20                  25                  30

Val Leu

<210> SEQ ID NO 74
<211> LENGTH: 31
<212> TYPE: PRT
<213> ORGANISM: Artificial Sequence
<220> FEATURE:
<223> OTHER INFORMATION: Pectate lyase (pel B) signal peptide
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid

<400> SEQUENCE: 74

Ala Met Ala Gly Gly Gly Xaa Xaa Cys Xaa Xaa Xaa Xaa Xaa Xaa Cys
1               5                   10                  15

Xaa Xaa Gly Gly Gly Ser Gly Gly Ser Gly Gly Met Ser Val Leu
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Pectate lyase (pel) B signal peptide
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid

<400> SEQUENCE: 75

Ala Met Ala Gly Gly Gly Xaa Xaa Cys Xaa Xaa Xaa Xaa Xaa Xaa Xaa
1               5                   10                  15

Cys Xaa Xaa Gly Gly Gly Ser Gly Gly Ser Gly Gly Met Ser Val Leu
            20                  25                  30

<210> SEQ ID NO 76
<211> LENGTH: 33
<212> TYPE: PRT
```

```
<213> ORGANISM: Artificial Sequence
<220> FEATURE:
<223> OTHER INFORMATION: Pectate lyase (pel) B signal peptide
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid

<400> SEQUENCE: 76

Ala Met Ala Gly Gly Gly Xaa Xaa Cys Xaa Xaa Xaa Xaa Xaa Xaa Xaa
1               5                   10                  15

Xaa Cys Xaa Xaa Gly Gly Gly Ser Gly Gly Ser Gly Gly Met Ser Val
            20                  25                  30

Leu

<210> SEQ ID NO 77
<211> LENGTH: 34
<212> TYPE: PRT
<213> ORGANISM: Artificial Sequence
<220> FEATURE:
<223> OTHER INFORMATION: Pectate lyase (pel) B signal peptide
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid

<400> SEQUENCE: 77

Ala Met Ala Gly Gly Gly Xaa Xaa Cys Xaa Xaa Xaa Xaa Xaa Xaa Xaa
1               5                   10                  15

Xaa Xaa Cys Xaa Xaa Gly Gly Gly Ser Gly Gly Ser Gly Gly Met Ser
            20                  25                  30

Val Leu

<210> SEQ ID NO 78
<211> LENGTH: 35
<212> TYPE: PRT
<213> ORGANISM: Artificial Sequence
<220> FEATURE:
<223> OTHER INFORMATION: Pectate lyase (pel) B signal peptide
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid

<400> SEQUENCE: 78

Ala Met Ala Gly Gly Gly Xaa Xaa Cys Xaa Xaa Xaa Xaa Xaa Xaa Xaa
1               5                   10                  15
```

-continued

```
Xaa Xaa Xaa Cys Xaa Xaa Gly Gly Gly Ser Gly Gly Ser Gly Gly Met
            20                  25                  30

Ser Val Leu
        35

<210> SEQ ID NO 79
<211> LENGTH: 18
<212> TYPE: PRT
<213> ORGANISM: Artificial Sequence
<220> FEATURE:
<223> OTHER INFORMATION: Residues of Flex segment

<400> SEQUENCE: 79

Asp Pro Cys Thr Trp Glu Val Trp Gly Arg Glu Cys Leu Gln Gly Gly
1               5                   10                  15

Gly Ser

<210> SEQ ID NO 80
<211> LENGTH: 19
<212> TYPE: PRT
<213> ORGANISM: Artificial Sequence
<220> FEATURE:
<223> OTHER INFORMATION: Residues of flex segment

<400> SEQUENCE: 80

Asp Pro Cys Thr Trp Glu Val Trp Gly Arg Glu Cys Leu Gln Gly Gly
1               5                   10                  15

Gly Gly Ser

<210> SEQ ID NO 81
<211> LENGTH: 19
<212> TYPE: PRT
<213> ORGANISM: Artificial Sequence
<220> FEATURE:
<223> OTHER INFORMATION: Residues of Flex segment

<400> SEQUENCE: 81

Asp Pro Cys Thr Trp Glu Val Trp Gly Arg Glu Cys Leu Gln Gly Gly
1               5                   10                  15

Gly Gly Ser
```